US012064218B2

(12) United States Patent
Freeman et al.

(10) Patent No.: US 12,064,218 B2
(45) Date of Patent: *Aug. 20, 2024

(54) WRIST-WORN DEVICE FOR COORDINATING PATIENT CARE

(71) Applicant: ZOLL Medical Corporation, Chelmsford, MA (US)

(72) Inventors: Gary A. Freeman, Waltham, MA (US); Michael Buonadonna, Arlington, MA (US); Guy R. Johnson, Wilton, NH (US); Justin R. Carroll, Brighton, CO (US); Annemarie Silver, Bedford, MA (US); Frederick J. Geheb, Lenexa, KS (US); John C. Amann, Worcester, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/515,972

(22) Filed: Nov. 1, 2021

(65) Prior Publication Data

US 2022/0125320 A1    Apr. 28, 2022

Related U.S. Application Data

(63) Continuation of application No. 15/230,591, filed on Aug. 8, 2016, now Pat. No. 11,202,579.

(51) Int. Cl.
*A61B 5/021* (2006.01)
*A61B 5/00* (2006.01)
(Continued)

(52) U.S. Cl.
CPC .......... *A61B 5/021* (2013.01); *A61B 5/14542* (2013.01); *A61B 5/6824* (2013.01);
(Continued)

(58) Field of Classification Search
CPC .. G09B 23/28; G09B 23/288; A61M 2230/63; A61M 2205/582;
(Continued)

(56) References Cited

U.S. PATENT DOCUMENTS 443,204 A   12/1890   Davis
651,962 A    6/1900   Boghean
(Continued)

FOREIGN PATENT DOCUMENTS

CN    1458852 A    11/2003
CN    1723057 A     1/2006
(Continued)

OTHER PUBLICATIONS

Jeffcott et al., "Measuring team performance in healthcare: Review research and implications for patient safety", Journal of Critical Care, 2008, pp. 188-196, vol. 23.

*Primary Examiner* — Malina D. Blaise
(74) *Attorney, Agent, or Firm* — The Webb Law Firm

(57) ABSTRACT

A feedback device for an acute care provider includes: at least one motion sensor; a haptic output component for providing feedback having a varying haptic pattern to the acute care provider regarding performance of a resuscitation activity; and a controller. The controller can be configured to receive and process a signal representative of performance of the resuscitation activity from the at least one motion sensor, compare the acute care provider's performance of the resuscitation activity to a target performance of the resuscitation activity, and cause the haptic output component to provide haptic feedback to the acute care provider by changing the haptic pattern based, at least in part, on the signal from the at least one motion sensor and the comparison of the acute care provider's performance to the target
(Continued)

performance of the resuscitation activity. The device can be adapted to be wrist-worn by the acute care provider.

21 Claims, 15 Drawing Sheets

(51) Int. Cl.
| | |
|---|---|
| *A61B 5/145* | (2006.01) |
| *A61H 31/00* | (2006.01) |
| *A61H 31/02* | (2006.01) |
| *A61M 16/00* | (2006.01) |
| *G09B 23/28* | (2006.01) |
| *A61B 5/024* | (2006.01) |
| *A61B 5/026* | (2006.01) |
| *A61B 5/11* | (2006.01) |
| *A61B 5/318* | (2021.01) |

(52) U.S. Cl.
CPC .......... *A61B 5/7405* (2013.01); *A61B 5/742* (2013.01); *A61H 31/00* (2013.01); *A61H 31/02* (2013.01); *A61M 16/0078* (2013.01); *A61M 16/0084* (2014.02); *G09B 23/288* (2013.01); *A61B 5/024* (2013.01); *A61B 5/026* (2013.01); *A61B 5/1118* (2013.01); *A61B 5/318* (2021.01); *A61B 5/441* (2013.01); *A61B 5/681* (2013.01); *A61B 5/7455* (2013.01); *A61B 2505/01* (2013.01); *A61B 2562/0219* (2013.01); *A61H 2201/5046* (2013.01); *A61H 2230/045* (2013.01); *A61H 2230/205* (2013.01); *A61H 2230/405* (2013.01); *A61H 2230/505* (2013.01); *A61M 2016/003* (2013.01); *A61M 2205/3306* (2013.01); *A61M 2205/332* (2013.01); *A61M 2205/3375* (2013.01); *A61M 2205/505* (2013.01); *A61M 2205/581* (2013.01); *A61M 2205/582* (2013.01); *A61M 2205/584* (2013.01); *A61M 2205/80* (2013.01); *A61M 2205/8206* (2013.01); *A61M 2230/06* (2013.01); *A61M 2230/205* (2013.01); *A61M 2230/30* (2013.01); *A61M 2230/432* (2013.01); *A61M 2230/50* (2013.01); *A61M 2230/62* (2013.01); *A61M 2230/63* (2013.01)

(58) Field of Classification Search
CPC .......... A61M 16/0084; A61M 16/0078; A61B 5/021; A61B 5/14542; A61B 5/6824; A61B 5/7405; A61B 5/742; A61H 31/00; A61H 31/02
See application file for complete search history.

(56) References Cited

U.S. PATENT DOCUMENTS

| | | | |
|---|---|---|---|
| 2,071,215 A | 2/1937 | Petersen | |
| 2,486,667 A | 11/1949 | Meister | |
| RE26,511 E | 12/1968 | Hewson | |
| 4,424,806 A | 1/1984 | Newman et al. | |
| 4,554,910 A | 11/1985 | Lally | |
| 4,676,232 A | 6/1987 | Olsson et al. | |
| 4,770,164 A | 9/1988 | Lach et al. | |
| 4,928,674 A | 5/1990 | Halperin et al. | |
| 4,932,879 A | 6/1990 | Ingenito et al. | |
| 4,987,783 A | 1/1991 | D'Antonio et al. | |
| 4,989,611 A | 2/1991 | Zanetti et al. | |
| 5,453,081 A | 9/1995 | Hansen | |
| 5,490,820 A | 2/1996 | Schock et al. | |
| 5,496,257 A | 3/1996 | Kelly | |
| 5,533,181 A | 7/1996 | Bergsneider | |
| 5,738,637 A | 4/1998 | Kelly et al. | |
| 5,743,864 A | 4/1998 | Baldwin, II | |
| 5,831,164 A | 11/1998 | Reddi et al. | |
| 5,844,482 A | 12/1998 | Guthrie et al. | |
| 6,013,041 A | 1/2000 | Leathers | |
| 6,027,452 A | 2/2000 | Flaherty et al. | |
| 6,174,295 B1 | 1/2001 | Cantrell et al. | |
| 6,301,964 B1 | 10/2001 | Fyfe et al. | |
| 6,406,427 B1 | 6/2002 | Williams et al. | |
| 7,074,199 B2 | 7/2006 | Halperin et al. | |
| 7,108,665 B2 | 9/2006 | Halperin et al. | |
| 7,429,250 B2 | 9/2008 | Halperin et al. | |
| 7,650,181 B2 | 1/2010 | Freeman et al. | |
| 7,805,114 B1 | 9/2010 | Quintana et al. | |
| 8,827,721 B2 | 9/2014 | Totman | |
| 8,880,166 B2 | 11/2014 | Tan et al. | |
| 9,125,793 B2 | 9/2015 | Palazzolo et al. | |
| 9,522,096 B2 | 12/2016 | Jensen et al. | |
| 9,586,015 B1* | 3/2017 | Lindner | A61M 16/0078 |
| 10,130,429 B1 | 11/2018 | Weir | |
| 2001/0011159 A1 | 8/2001 | Cantrell et al. | |
| 2002/0133197 A1 | 9/2002 | Snyder et al. | |
| 2004/0015191 A1 | 1/2004 | Otman et al. | |
| 2004/0082888 A1* | 4/2004 | Palazzolo | A61B 5/7242 601/41 |
| 2004/0162585 A1 | 8/2004 | Elghazzawi et al. | |
| 2004/0267325 A1 | 12/2004 | Geheb et al. | |
| 2006/0056655 A1 | 3/2006 | Wen et al. | |
| 2006/0116724 A1 | 6/2006 | Snyder | |
| 2006/0173501 A1 | 8/2006 | Stickney et al. | |
| 2006/0241415 A1 | 10/2006 | Boese et al. | |
| 2008/0171311 A1 | 7/2008 | Centen et al. | |
| 2008/0258901 A1* | 10/2008 | Rubey | G16H 40/63 340/502 |
| 2009/0240295 A1 | 9/2009 | Kellum | |
| 2009/0270931 A1 | 10/2009 | Liden | |
| 2010/0211127 A1 | 8/2010 | Eerden | |
| 2010/0248679 A1 | 9/2010 | Oei et al. | |
| 2011/0117529 A1 | 5/2011 | Barash et al. | |
| 2011/0117878 A1 | 5/2011 | Barash et al. | |
| 2011/0172550 A1 | 7/2011 | Martin et al. | |
| 2012/0075464 A1 | 3/2012 | Derenne et al. | |
| 2012/0112903 A1 | 5/2012 | Kaib et al. | |
| 2012/0123224 A1 | 5/2012 | Packer et al. | |
| 2012/0195473 A1 | 8/2012 | De Haan et al. | |
| 2013/0138168 A1 | 5/2013 | Quan et al. | |
| 2013/0281897 A1* | 10/2013 | Hoffmann | A61H 23/00 601/107 |
| 2013/0296719 A1 | 11/2013 | Packer et al. | |
| 2013/0310718 A1 | 11/2013 | Jensen et al. | |
| 2014/0052032 A1 | 2/2014 | Freeman et al. | |
| 2014/0085082 A1* | 3/2014 | Lyon | G16H 40/63 340/539.12 |
| 2014/0107718 A1* | 4/2014 | Foote | A61N 1/3968 607/142 |
| 2014/0201627 A1 | 7/2014 | Freeman et al. | |
| 2014/0236055 A1* | 8/2014 | Woerlee | A61H 31/00 601/41 |
| 2014/0342331 A1 | 11/2014 | Freeman | |
| 2014/0365175 A1 | 12/2014 | Packer et al. | |
| 2015/0044653 A1* | 2/2015 | Levine | G09B 23/288 434/262 |
| 2015/0045697 A1* | 2/2015 | Richard | A61B 5/11 600/587 |
| 2015/0087919 A1 | 3/2015 | Johnson et al. | |
| 2015/0088016 A1 | 3/2015 | Fleischacker et al. | |
| 2015/0325148 A1* | 11/2015 | Kim | G09B 23/288 434/265 |
| 2016/0128626 A1 | 5/2016 | Johnson et al. | |
| 2017/0273864 A1 | 9/2017 | Kaufman et al. | |
| 2018/0021533 A1 | 1/2018 | Gausche-Hill et al. | |
| 2018/0092803 A1 | 4/2018 | Freeman et al. | |
| 2018/0250086 A1 | 9/2018 | Grubbs | |
| 2018/0311452 A1 | 11/2018 | Walker | |

(56) References Cited

U.S. PATENT DOCUMENTS

FOREIGN PATENT DOCUMENTS

| CN | 1750857 A | 3/2006 |
|---|---|---|
| CN | 101001668 A | 7/2007 |
| KR | 20160111712 A | 9/2016 |

* cited by examiner

Los Angeles Prehospital Stroke Screen

| Screening Criteria | Yes | No |
|---|---|---|
| 1. Age over 45 years | | |
| 2. No prior history of seizure disorder | | |
| 3. New onset of neurological symptoms in just 24 hours | | |
| 4. Patient was ambulatory at baseline (prior to event) | | |
| 5. Blood glucose between 60 and 400 | | |

Exam: Look for obvious

| | Normal | Right | Left |
|---|---|---|---|
| Facial smile/grimace | ___ | ___ Droop | ___ Droop |
| Grip | ___ | ___ Weak grip <br> ___ No grip | ___ Weak grip <br> ___ No grip |
| Arm Weakness | ___ | ___ Drifts down <br> ___ Falls rapidly | ___ Drifts down <br> ___ Falls rapidly |

FIG. 1B

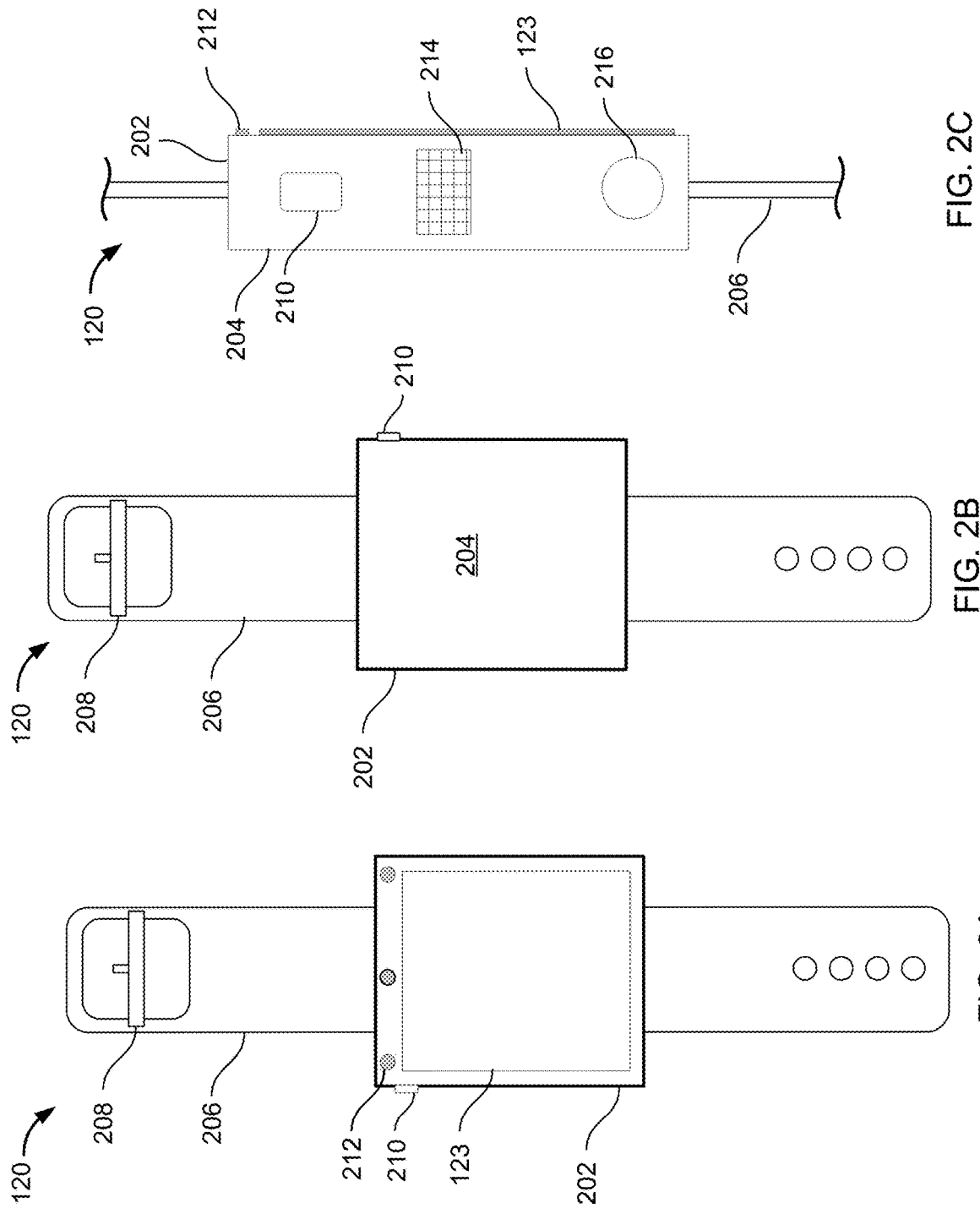

WRIST-WORN DEVICE FOR COORDINATING PATIENT CARE

CROSS REFERENCE TO RELATED APPLICATION

The present application is a continuation of U.S. patent application Ser. No. 15/230,591, filed on Aug. 8, 2016, entitled "Wrist-Worn Device for Coordinating Patient Care", the disclosure of which is hereby incorporated by reference in its entirety.

BACKGROUND

Technological Field

The present disclosure is related to electronic devices for coordinating medical care for patients and, in some examples, to wearable electronic devices having circuitry configured for coordinating such medical care.

Description of Related Art

Acute care is delivered to patients in emergency situations in the pre-hospital and hospital settings for patients experiencing a variety of acute medical conditions involving the timely diagnosis and treatment of disease states that, left alone, will likely degenerate into a life-threatening condition and, potentially, death within a period of 72 hours or less. Stroke, dyspnea (difficulty breathing), traumatic arrest, myocardial infarction and cardiac arrest are a few examples of disease states for which acute care is delivered to patients in an emergency setting. Acute care comprises different treatment and/or diagnosis, depending upon the disease state.

One example of acute care is cardio-pulmonary resuscitation (CPR), which is a process by which one or more acute care providers may attempt to resuscitate a patient who may have suffered a cardiac arrest or other acute adverse cardiac event by taking one or more actions, for example, providing chest compressions and ventilation to the patient. The first five to eight minutes of CPR, including chest compressions, are critically important, largely because chest compressions help maintain blood circulation through the body and in the heart itself. Ventilation is also key part of CPR because ventilations help to provide much needed gas exchange (e.g., oxygen supply and carbon dioxide deposit) for the circulating blood.

CPR may be performed by a team of one or more acute care providers, for example, an emergency medical services (EMS) team made up of emergency medical technicians (EMTs), a hospital team including medical caregivers (e.g., doctors, nurses, etc.), and/or bystanders responding to an emergency event. In some instances, one acute care provider can provide chest compressions to the patient while another can provide ventilations to the patient, where the chest compressions and ventilations may be time and/or coordinated according to an appropriate CPR protocol. When professionals such as EMTs provide care, ventilation may be provided via a ventilation bag that an acute care provider squeezes, for example, rather than by mouth-to-mouth. CPR can be performed in conjunction with electrical shocks to the patient provided by an external defibrillator, such as an automatic external defibrillator (AED). Such AEDs often provide instructions (e.g., in the form of audible feedback) to acute care providers, such as "Push Harder" (when the acute care provider is not performing chest compressions according to the desired depth), "Stop CPR," "Stand Back" (because a shock is about to be delivered), and so on. In order to determine the quality of chest compressions being performed, certain defibrillators may obtain information from one or more accelerometers (such as those which are provided with e CPR D PADZ®, CPR STAT PADZ®, and ONE STEP™ pads made by ZOLL MEDICAL of Chelmsford, Mass.) that can be used to provide data to determine information such as depth of chest compressions (e.g., to determine that the compressions are too shallow or too deep and to thus cause an appropriate cue to be provided by the defibrillator).

SUMMARY

Examples of the present invention will now be described in the following numbered clauses:

Clause 1: A feedback device for an acute care provider, the device comprising: at least one motion sensor; a haptic output component for providing feedback having a varying haptic pattern to the acute care provider regarding performance of a resuscitation activity by the acute care provider; and a controller configured to receive and process a signal representative of performance of the resuscitation activity from the at least one motion sensor, compare the acute care provider's performance of the resuscitation activity to a target performance of the resuscitation activity, and cause the haptic output component to provide haptic feedback to the acute care provider by changing the haptic pattern based, at least in part, on the signal from the at least one motion sensor and the comparison of the acute care provider's performance to the target performance of the resuscitation activity.

Clause 2: The feedback device of clause 1, wherein causing the haptic output component to provide feedback by changing the haptic pattern comprises providing a first haptic pattern to encourage the acute care provider in performance of the resuscitation activity and a second haptic pattern to instruct the acute care provider to adjust or modify performance of the resuscitation activity.

Clause 3: The feedback device of clause 2, wherein encouraging the acute care provider in performance of the resuscitation activity comprises encouraging the acute care provider to continue performing the resuscitation activity in a substantially similar manner.

Clause 4: The feedback device of clause 2 or clause 3, wherein comparing the acute care provider's performance of the resuscitation activity to a target performance of the resuscitation activity comprises comparing measured values for resuscitation activity parameters to target parameter values for the resuscitation activity.

Clause 5: The feedback device of clause 4, wherein feedback with the first haptic pattern is provided when the measured values are within a range of the target parameter values, and feedback with the second haptic pattern is provided when the measured values are not within the target range.

Clause 6: The feedback device of any of clauses 2 to 4, wherein the first haptic pattern and/or the second haptic pattern comprise one or more of a low intensity vibration, a high intensity vibration, a vibration having an intensity that varies in a saw tooth pattern, a pulse vibration at predetermined intervals, and/or a vibration including groups of haptic pulses of predetermined intensity and duration followed by intervals without haptic pulses.

Clause 7: The feedback device of any of clauses 1 to 6, wherein causing the haptic output component to provide feedback by changing the haptic pattern comprises providing feedback with a first haptic pattern during a chest compression downstroke until a target chest compression depth is reached, followed by providing feedback with a second haptic pattern to encourage the acute care provider to release the chest compression.

Clause 8: The feedback device of any of clauses 1 to 7, wherein causing the haptic output component to provide feedback by changing the haptic pattern comprises providing feedback with a first haptic pattern during compression of a manual ventilation bag until a target ventilation volume is reached, followed by feedback with a second haptic pattern to encourage the acute care provider to release the manual ventilation bag.

Clause 9: The feedback device of any of clauses 1 to 8, further comprising an audio output component for providing audio feedback for performance of the resuscitation activity by the acute care provider.

Clause 10: The feedback device of clause 9, wherein the controller is configured to cause the audio output component to emit a sound substantially simultaneous with the haptic feedback provided by the haptic output component.

Clause 11: The feedback device of clause 9, wherein the controller is configured to cause the audio output component to provide feedback to encourage the acute care provider to perform a first aspect of the resuscitation activity, and wherein the controller is configured to cause the haptic output component to provide feedback to encourage the acute care provider to perform a second aspect of the resuscitation activity.

Clause 12: The feedback device of any of clauses 9 to 11, wherein the controller is configured to cause the audio output component to emit multiple tones forming a major chord to encourage the acute care provider in performance of the resuscitation activity, and to emit multiple tones forming a minor or descending chord to instruct the acute care provider to modify performance of the resuscitation activity.

Clause 13: The feedback device of any of clauses 1 to 12, further comprising a visual display, wherein the controller is configured to cause a visual indicator to appear on the visual display to provide feedback for performance of the resuscitation activity by the acute care provider.

Clause 14: The feedback device of clause 13, wherein the visual indicator comprises a performance indicator (PI).

Clause 15: The feedback device of any of clauses 1 to 15, wherein the at least one motion sensor comprises at least one of a single-axis accelerometer, a multi-axis accelerometer, and a gyroscope.

Clause 16: The feedback device of any of clauses 1 to 15, wherein the target performance of the resuscitation activity comprises performing chest compressions at a compression depth of between about 2.0 inches and 2.4 inches.

Clause 17: The feedback device of any of clauses 1 to 16, wherein the target performance of the resuscitation activity comprises performing chest compressions at a compression rate of between about 100 and 120 compressions per minute.

Clause 18: The feedback device of any of clauses 1 to 17, wherein the target performance of the resuscitation activity comprises performing ventilations at a ventilation rate of about 10 ventilations per minute for an adult or about 20 ventilations per minute for an infant.

Clause 19: The feedback device of any of clauses 1 to 18, wherein a patient condition treated by the acute care provider comprises at least one of stroke, dyspnea, traumatic arrest, myocardial infarction and cardiac arrest.

Clause 20: A feedback device for providing feedback to an acute care provider for manual ventilation of a patient, the device comprising: a housing configured to be connected to a portion of a manual ventilation bag; a haptic output component for providing feedback to the acute care provider about performance of manual ventilation to a patient with the manual ventilation bag; and a controller configured to cause the haptic output component to provide feedback to the acute care provider, the feedback comprising providing a first haptic pattern of feedback to encourage the acute care provider in performance of an action related to manual ventilation of the patient.

Clause 21: The feedback device of clause 20, further comprising a flow sensor for measuring information representative of one or more of a rate of compression of the ventilation bag and flow rate of air expelled from the manual ventilation bag.

Clause 22: The feedback device of clause 21, wherein the controller is further configured to compare the measured compression rate and/or flow rate to target parameter values, and wherein the feedback is based, at least in part, on the comparison of the measured values and the target parameter values.

Clause 23: The feedback device of clause 21 or clause 22, wherein causing the haptic output component to provide feedback comprises providing the first haptic pattern of feedback to encourage the acute care provider to continue performance of manual ventilation of the patient and a second haptic pattern of feedback to instruct the acute care provider to adjust or modify performance of manual ventilations based, at least in part, on the comparison of the measured values and the target parameter values.

Clause 24: The feedback device of any of clauses 20 to 23, wherein a patient condition treated by the acute care provider comprises at least one of stroke, dyspnea, traumatic arrest, myocardial infarction and cardiac arrest:

Clause 25: A non-transitory computer-readable medium for providing feedback to an acute care provider for performing a resuscitation activity to a patient, comprising program instructions that, when executed by at least one processor, cause the at least one processor to: receive and process a signal representative of performance of the resuscitation activity from at least one motion sensor of a feedback device worn by the acute care provider; compare the acute care provider's performance of the resuscitation activity to a target performance of the resuscitation activity; cause a haptic output component to provide haptic feedback, based at least in part on the comparison of the acute care provider's performance of the resuscitation activity to the target performance of the resuscitation activity, to the acute care provider to encourage the acute care provider to perform a first aspect of the resuscitation activity; and cause another feedback output component to provide feedback, based at least in part on the comparison of the acute care provider's performance of the resuscitation activity to the target performance of the resuscitation activity, to encourage the acute care provider to perform a second aspect of the resuscitation activity.

Clause 26: The non-transitory computer-readable medium of clause 25, wherein causing a haptic output component to provide haptic feedback to the acute care provider to encourage the acute care provider to perform the first aspect of the resuscitation activity comprises changing a haptic pattern output from the haptic output component based, at least in part, on the signal from the at least one motion sensor and the comparison of the acute care provider's performance to the target performance of the resuscitation activity.

Clause 27: A device adapted to be wrist-worn by a user during a rescue event, comprising: an user interface adapted to assist the user in executing one or more resuscitation related activities; an input component configured for the user wearing the device to input a marker for providing a time-stamped record of a resuscitation related activity during the rescue event; and a communications component for establishing communication with an external device and uploading the marker to the external device for producing a summary record of the rescue event.

Clause 28: The device of clause 27, wherein the input component comprises at least one of a microphone; a touch screen, a response button, and a motion sensor.

Clause 29: The device of clause 28, wherein the input component is configured to record speech by the user with the microphone and to select the marker from a plurality of preset markers based on the recorded speech.

Clause 30: The device of any of clauses 27 to 29, wherein the rescue event comprises at least one of performing chest compressions; performing ventilations; and administering a medicinal agent to the patient.

Clause 31: The device of any of clauses 27 to 30, wherein the communications component comprises a wireless transmitter or a wireless transceiver.

Clause 32: The device of any of clauses 27 to 31, wherein the user interface is configured to determine a treatment protocol for a patient based on the input marker, and to assist the user in performing aspects of the treatment protocol.

Clause 33: The device of clause 32, wherein the treatment protocol corresponds to treatment of a patient condition comprising at least one of stroke, dyspnea, traumatic arrest, myocardial infarction and cardiac arrest.

Clause 34: The device of clause 33, wherein assisting the user to perform aspects of the treatment protocol comprises instructing the user to perform the resuscitation activity again after a predetermined period of time.

Clause 35: The device of any of clauses 32 to 34, wherein the user interface comprises an output component configured to provide notifications to the user to perform resuscitation activities, and wherein the user interface is configured to cause the output component to provide the notifications for performing the resuscitation activities to the user according to the treatment protocol.

Clause 36: The device of clause 35, wherein the output component comprises at least one of a visual display, touch screen, speaker, and haptic feedback device.

Clause 37: The device of clause 35 or clause 36, wherein the notifications comprise at least one of an audible prompt, a recorded message, haptic feedback, and a visual prompt.

Clause 38: The device of any of clauses 35 to 37, wherein the notifications to the user to perform the resuscitation activities comprise a list of resuscitation activities to be performed for the patient provided with the output component.

Clause 39: A device adapted to be wrist-worn by a user during a rescue event, comprising: a user interface adapted to assist the user in executing one or more resuscitation related activities; a processor configured to receive a signal for alerting the user of at least one resuscitation activity related to the rescue event; and a haptic output component in communication with the processor and configured to provide the user wearing the device with an alert notification of the at least one resuscitation activity related to the rescue event.

Clause 40: The device of clause 39, wherein the haptic output component is configured to provide the user wearing the device with a first type of alert notification to inform the user to perform a first resuscitation activity and a second alert notification to inform the user to perform a second resuscitation activity.

Clause 41: The device of clause 39 or clause 40, wherein the signal for alerting the user is received by the device from at least one of a portable computing device in wireless communication with the wrist-worn device, a rescue management apparatus, a therapeutic medical device, another wrist-worn device, and a remote computer network.

Clause 42: The device of any of clauses 39 to 41, wherein the alert notification is provided to instruct the user to perform one or more of: checking or observing activities performed by other acute care providers during the rescue event, changing a position or role for the rescue event, checking patient vital signs, and/or standing back so that a deliberation shock can be provided to the patient.

Clause 43: The device of any of clauses 39 to 42, wherein the alert notification comprises vibrations according to at least a first haptic pattern to instruct the user to begin performing the resuscitation activity and vibrations according to a second haptic pattern to instruct the acute care provider to cease performing the resuscitation activity.

Clause 44: The device of clause 43, wherein the first haptic pattern and/or the second haptic pattern comprise one or more of a low intensity vibration, a high intensity vibration, a vibration having an intensity that varies in a saw tooth pattern, a pulse vibration at predetermined intervals, and/or a vibration including groups of haptic pulses of predetermined intensity and duration followed by intervals without haptic pulses.

Clause 45: The device of any of clauses 39 to 44, further comprising an audio output component configured to provide the alert notification with the haptic output component.

Clause 46: The device of clause 45, wherein the processor is configured to cause the audio output component to emit a sound substantially simultaneous with the alert notification emitted by the haptic output component.

Clause 47: The feedback device of clause 45, wherein the processor is configured to cause the audio output component to provide audio feedback for a first type of alert notification and to cause the haptic output component to provide haptic feedback for a second type of alert notification.

Clause 48: A device for assisting resuscitation, comprising: a processor for processing a motion-based signal produced from a victim to provide an indication of victim downtime; and an output component configured to output the indication of the victim downtime to an acute care provider for providing resuscitation treatment to the victim.

Clause 49: The device of clause 48, further comprising at least one motion sensor coupled to the processor, the motion sensor being configured to provide the motion-based signal produced from the victim to the processor.

Clause 50: The device of clause 49, wherein the at least one motion sensor comprises one or more of: a single axis accelerometer, a multi-axis accelerometer, and a gyroscope.

Clause 51: The device of any of clauses 48 to 50, further comprising at least one physiological sensor for measuring physiological information of the victim, the physiological sensor comprising one or more of a heart rate sensor, a pulse oximetry sensor, and a blood pressure sensor.

Clause 52: The device of clause 51, wherein the output component is configured to output the physiological information along with the indication of patient downtime.

Clause 53: The device of clause 51 or clause 52, wherein the processor is configured to identify occurrence of a physiological event based on analysis of the physiological information and motion-based signals.

Clause 54: The device of any of clauses 48 to 53, wherein the output component comprises a wireless transceiver configured to transmit the indication of the victim downtime to one or more of a wrist-worn device worn by an acute care provider, a therapeutic medical device, a rescue management apparatus, and/or a portable computing device.

Clause 55: The device of any of clauses 48 to 54, further comprising computer readable memory operatively connected to the processor, the memory comprising identifying information and/or medical history information for the victim.

Clause 56: The device of clause 55, wherein the output component is configured to output the identifying information and/or medical history information along with the indication of the victim downtime to the acute care provider.

Clause 57: The device of any of clauses 48 to 56, wherein the output component is further configured to transmit an alert to an emergency response system based on the determined patient downtime.

Clause 58: The device of any of clauses 48 to 57, wherein the output component comprises an audio output component for providing an audible alert capable of being heard by bystanders based on the determined patient downtime.

Clause 59: A device adapted to be wrist-worn, comprising: at least one sensor for sensing at least one physiological or motion-based signal for a person wearing the device; a wireless transceiver; and a controller configured to: receive the at least one physiological or motion-based signal from the at least one sensor; estimate a time period in which the person wearing the device has been incapacitated based on analysis of the at least one physiological or motion-related signal; and transmit, with the wireless transceiver, information about the estimated time period in which the person wearing the device has been incapacitated to an external computing device.

Clause 60: The device of clause 59, wherein the controller is configured to receive victim medical history information from at least one of (a) computer readable memory operatively connected to the controller and (b) the wireless transceiver, the transceiver being configured to download the victim medical history information from an external database.

Clause 61: The device of clause 60, wherein the controller is configured to transmit the victim medical history information to the external computing device by the wireless transceiver.

Clause 62: The device of any of clauses 59 to 61, wherein the at least one sensor comprises at least one of: an accelerometer, a gyroscope, a heart rate sensor, a pulse oximetry sensor, and a blood pressure sensor.

Clause 63: The device of any of clauses 59 to 62, wherein the controller is configured to continuously or substantially continuously monitor the condition of the victim based on the at least one physiological signal received from the at least one sensor.

Clause 64: The device of any of clauses 59 to 64, wherein the controller is configured to identify occurrence of a physiological event based on analysis of the physiological or motion-based signals received from the at least one sensor.

Clause 65: The device of clause 64, further comprising an output component, wherein the output component is configured to output an alert when the physiological event is identified.

Clause 66: The device of clause 65, wherein the alert comprises an audible alert.

Clause 67: A non-transitory computer-readable medium for providing information about a victim to an acute care provider comprising program instructions that, when executed by at least one processor, cause the at least one processor to: receive and process a motion-based signal produced from the victim; receive and process a signal produced from at least one physiological sensor for measuring physiological information of the victim; estimate an indication of victim downtime based on analysis of the signal produced from the at least one physiological sensor and the motion-related signal; output the indication of the victim downtime and physiological information for the victim to an acute care provider for providing resuscitation treatment to the victim.

Clause 68: A device configured to be wrist-worn, comprising: a wireless transceiver; and a controller having an output component, the device being configured to: establish a wireless connection with an external computing device associated with a victim; wirelessly communicate with the external computing device at least one of personal identification information of the victim, estimated location of the victim, recent motion-related activities of the victim, estimated time period in which the victim has been incapacitated, medical history information of the victim, and physiological event information of the victim; and provide through the output component, as a notification to an acute care provider wearing the device, at least one of the personal identification information of the victim, estimated location of the victim, recent motion-related activities of the victim, estimated time period in which the victim has been incapacitated, medical history information of the victim, physiological event information of the victim, and associated treatment protocol.

Clause 69: The device of clause 68, wherein the controller is further configured to determine a treatment protocol for treating the victim based, at least in part, on at least one of the personal identification information of the victim, recent motion-related activities of the victim, estimated time period in which the victim has been incapacitated, medical history information of the victim, and physiological event information.

Clause 70: The device of clause 69, wherein the external computing device comprises a device adapted to be worn by the victim.

Clause 71: The device of clause 70, wherein the device adapted to be worn by the victim comprises a multipurpose electronic device comprising computer readable memory comprising the personal identification information and/or medical history information of the victim.

Clause 72: The device of clause 70, wherein the device adapted to be worn by the victim comprises a wearable therapeutic medical device.

Clause 73: The device of any of clauses 69 to 72, wherein the external computing device comprises a database of electronic medical records.

Clause 74: The device of any of clauses 69 to 73, wherein the controller is configured to provide, by the output component, feedback for performing at least one resuscitation activity to the acute care provider wearing the device in accordance with the treatment protocol.

Clause 75: A rescue management system comprising: at least one device adapted to be wrist-worn by at least one individual at an emergency scene, each device comprising a controller and an output component, the controller being configured to: identify an additional device as being worn by a victim located at the emergency scene; receive from the additional device worn by the victim at least one of personal identification information of the victim, recent motion-related activities of the victim, time period in which the victim wearing the additional device has been incapacitated, medical history information of the victim, and physiological event information of the victim; determine a treatment protocol for treating the victim based, at least in part, on at least one of the personal identification information of the victim, recent motion-related activities of the victim, time period in which the victim wearing the additional device has been incapacitated, medical history information of the victim, and physiological event information of the victim; and provide, by the output component, instructions for performing at least one resuscitation activity to the respective acute care provider wearing the device in accordance with the treatment protocol.

Clause 76: The system of clause 75, further comprising a rescue management apparatus in communication with the at least one device worn by an individual at the emergency scene, the rescue management apparatus comprising a controller configured to: receive the treatment protocol from at least one of the wrist-worn devices; determine a role for each of the respective individuals related to performance of at least one resuscitation activity; and provide information for each device to present to the respective individual to assist the individual in performing the at least one resuscitation activity in accordance with the treatment protocol corresponding to the role of the individual.

Clause 77: A device adapted to be wrist-worn by a user during a rescue event, comprising: at least one sensor for recording gestural motion of the user; and a processor configured to receive and process information provided from the at least one sensor and identify a resuscitation activity for the user based on the recorded gestural motion of the user from the at least one sensor.

Clause 78: The device of clause 77, wherein the at least one sensor comprises one or more of a single axis accelerometer, a multi-axis accelerometer, and a gyroscope.

Clause 79: The device of clause 77 or clause 78, wherein identifying a resuscitation activity for the user based on the recorded gestural motion of the user comprises comparing information from the at least one sensor to expected values for one or more gestures.

Clause 80: The device of any of clauses 77 to 79, wherein the resuscitation activity comprises one or more of chest compressions, ventilations, and administering a therapeutic agent.

Clause 81: The device of any of clauses 77 to 80, wherein the gestural motion that can be identified comprises movement of the acute care providers hand/wrist in one or more of a circular pattern, figure eight pattern, back and forth pattern, and/or outlining a recognizable shape with the hand/wrist.

Clause 82: The device of any of clauses 77 to 81, further comprising a user interface adapted to assist the user in executing the identified resuscitation activity.

Clause 83: A device adapted to be wrist-worn by a user during a rescue event, comprising: an input component for receiving information related to a resuscitation role assigned to the user; an output component for providing information to assist the user during the rescue event according to the assigned resuscitation role; and a processor configured to: receive the information related to the assigned resuscitation role from the input component, determine a treatment protocol corresponding to the assigned resuscitation role, and cause the output component to provide resuscitation information related to the treatment protocol corresponding to the assigned resuscitation role.

Clause 84: The device of clause 83, wherein the assigned resuscitation role comprises at least one of: providing chest compressions to a patient; providing ventilation to the patient; setting up a medical device to treat the patient; and/or administering a therapeutic agent to the patient.

Clause 85: The device of clause 83 or clause 84, wherein the input component comprises at least one motion sensor configured to obtain a motion-based signal representative of performance of the assigned resuscitation role by the user.

Clause 86: The device of any of clauses 83 to 85, wherein the processor is further configured to determine an acute care provider evaluation metric for performance of the assigned role based on the received information.

Clause 87: The device of clause 86, wherein the acute care provider evaluation metric is based, at least in part, on a comparison between measured values for resuscitation activity performed by the acute care provider and target parameters for the resuscitation activity.

Clause 88: The device of clause 86 or clause 87, wherein the acute care provider evaluation metric comprises an overall score for the acute care provider inclusive of each resuscitation activity performed by the acute care provider.

Clause 89: The device of any of clauses 83 to 88, wherein the processor is further configured to assign a new role to the user after a predetermined period of time.

Clause 90: The device of any of clauses 83 to 88, wherein the processor is further configured to identify and/or assign a role to be performed by the acute care provider by one or more of: (a) identifying performance of the activity by the acute care provider and (b) identifying an action by the acute care provider corresponding to the resuscitation activity.

Clause 91: The device of clause 90, wherein the action corresponding to the resuscitation activity comprises: (a) performing a predetermined gesture corresponding to the resuscitation activity; (b) making a selection on a touch screen of the device; (c) speaking the selected resuscitation activity; and (d) positioning the wrist-worn device in proximity with another device configured to assist with performance of the resuscitation activity.

Clause 92: The device of clause 91, wherein the device configured to assist with performance of the resuscitation activity comprises at least one of a chest compression assist device, a mechanical ventilation device, and a manual ventilation bag.

Clause 93: The device of any of clauses 83 to 92, wherein determining the treatment protocol for the resuscitation activity comprises determining a treatment protocol for treatment of a traumatic brain injury.

Clause 94: The device of clause 93, wherein determining the treatment protocol for treatment of a traumatic brain injury is based, at least in part, on at least one of the following physiological parameters of a patient: blood pressure, pulse oximetry ($SpO_2$), exhaled carbon dioxide concentration ($EtCO_2$), and heart rate.

Clause 95: A rescue management system comprising: at least one computerized wrist watch configured to provide information for assisting a user wearing the wrist watch in performing at least one resuscitation activity on a patient according to a resuscitation role of the respective user; a rescue management apparatus in wireless communication with each of the at least one computerized wrist watches, the rescue management apparatus comprising a controller configured to: provide an output that assigns the at least one wrist watch with the respective resuscitation role such that the at least one wrist watch outputs resuscitation information related to a treatment protocol corresponding to the assigned resuscitation role.

Clause 96: The rescue management system of clause 95, wherein providing an output that assigns the at least one wrist watch with the respective resuscitation role comprises determining the role for each user based on information received from the computerized wrist watches.

Clause 97: The rescue management system of clause 96, wherein the information received from the at least one wrist watch comprises motion-based information representative of a gesture or activity being performed by the user.

Clause 98: The rescue management system of clause 96 or clause 97, wherein the information received from the at least one wrist watch comprises identifying information about the user of the watch, the identifying information comprising: one or more of: physical strength of the acute care provider, an acute care provider's experience with particular types of resuscitation activity, acute care provider size, acute care provider height, and acute care provider weight.

Clause 99: The rescue management system of any of clauses 96 to 98, wherein the information received from the at least one wrist watch comprises an indication of a location of the user relative to one or more of: other devices at an emergency scene, other acute care providers at an emergency scene, and/or an emergency victim.

Clause 100: The rescue management system of any of clauses 95 to 99, wherein the controller is configured to provide an output, after a predetermined period of time, that assigns the at least one wrist watch with a new role, such that the at least one wrist watch outputs resuscitation information related to a treatment protocol corresponding to a new resuscitation role to be performed by the user.

Clause 101: The rescue management system of any of clauses 95 to 100, wherein a role comprises at least one of: providing chest compressions to a patient; providing ventilation to the patient; setting up a medical device to treat the patient; and/or administering a therapeutic agent to the patient.

Clause 102: The rescue management system of any of clauses 95 to 101, wherein the controller is configured to determine a number of computerized wrist watches within a predetermined distance from an emergency victim, and to determine the treatment protocol for the victim based, at least in part, on the determined number of computerized wrist watches.

Clause 103: The rescue management system of any of clauses 95 to 102, wherein the at least one resuscitation role performed by a user of one wrist watch is different from the at least one resuscitation role performed by a user of another wrist watch.

Clause 104: A rescue management system, comprising: a transceiver configured to be in wireless communication with a plurality of wearable devices, each wearable device configured to provide information for assisting an acute care provider of the wearable device in performing at least one resuscitation activity on a patient according to a resuscitation role assigned to the respective acute care provider; and at least one processor configured to: associate each of the wearable devices with the respective acute care provider, receive and process information associated with each wearable device to provide a time-stamped record of activity for each acute care provider, and output a summary having information indicative of a quality of care provided by each acute care provider based on the time-stamped record of activity received for each acute care provider.

Clause 105: The rescue management system of clause 104, wherein each wearable device comprises a motion sensor, and wherein the received information associated with each wearable device comprises motion-based information representative of movement of the acute care provider obtained by the motion sensor.

Clause 106: The rescue management system of clause 105, wherein the output summary having information indicative of a quality of care provided by each acute care provider is based, at least in part, on a comparison between information representative of movement of the acute care provider during performance of the resuscitation activity and target parameters for the resuscitation activity.

Clause 107: The rescue management system of any of clauses 104 to 106, wherein the output summary for each acute care provider comprises a score or metric for each resuscitation activity performed on the patient by the acute care provider.

Clause 108: The rescue management system of any of clauses 104 to 107, wherein the output summary for each acute care provider comprises an overall score for each acute care provider inclusive of each resuscitation activity performed by the acute care provider.

Clause 109: The rescue management system of any of clauses 104 to 108, wherein the output summary comprises a score for a resuscitation activity performed on the patient by multiple acute care providers based on information received from the plurality of wearable devices.

Clause 110: The rescue management system of any of clauses 104 to 109, wherein the output a summary comprises a total score representative of quality of care provided to the patient by the acute care providers based on the received information from the plurality of wearable devices.

Clause 111: The rescue management system of any of clauses 104 to 110, wherein the at least one resuscitation activity comprise at least one of performing chest compressions, manual or automatic ventilation, setting up mechanical medical devices, administering medications to the patient, monitoring patient vital signs, coordinating transportation of the patient from the emergency scene to a medical facility, and coordinating exchange of responsibility for treatment of the patient upon arrival at the medical facility.

Clause 112: The rescue management system of any of clauses 104 to 111, wherein a patient condition treated by the acute care provider comprises at least one of stroke, dyspnea, traumatic arrest, myocardial infarction and cardiac arrest.

Clause 113: A device adapted to be wrist worn comprising: a transceiver configured to receive status information from at least one defibrillator device; a processor configured to process the information received from the at least one defibrillator device and generate a summary of status information of the at least one defibrillator device; and an output component for displaying the summary of status information of the at least one defibrillator device to the user wearing the device.

Clause 114: The device of clause 113, wherein the processor is configured to estimate a location of the user based on analysis of a quality and/or intensity of a signal received from the at least one defibrillator device.

Clause 115: The device of clause 114, wherein the summary comprises directions from the user's estimated location to a location of the at least one defibrillator device.

Clause 116: The device of clause 114 or clause 115, wherein the summary displayed by the output component comprises status information for each defibrillator device within a predetermined distance of the user's estimated location.

Clause 117: The device of any of clauses 113 to 116, further comprising location determining circuitry in electronic communication with the processor, wherein the processor is configured to estimate a location of the user based on information received from the location determining circuitry.

Clause 118: The device of clause 117, wherein the location determining circuitry comprises circuitry for a global positioning system (GPS).

Clause 119: The device of any of clauses 113 to 118, wherein the at least one defibrillator device comprises an automated external defibrillator device (AED).

Clause 120: The device of any of clauses 113 to 119, wherein the output component comprises a visual display.

Clause 121: The device of any of clauses 113 to 120, comprising a computerized wrist watch.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the disclosure.

BRIEF DESCRIPTION OF THE DRAWINGS

FIG. 1B is an example of a patient assessment questionnaire to be used by an acute care provider when treating a patient undergoing a stroke;

FIG. 2A is a schematic drawing of a front view of an exemplary wrist-worn device for providing medical assistance to a user in accordance with various embodiments;

FIG. 2B is a schematic drawing of a rear view of the exemplary wrist-worn device of FIG. 2A;

FIG. 2C is a schematic drawing of an enlarged side view of a portion of the exemplary wrist-worn device of FIG. 2A;

DETAILED DESCRIPTION

Figure 1A:
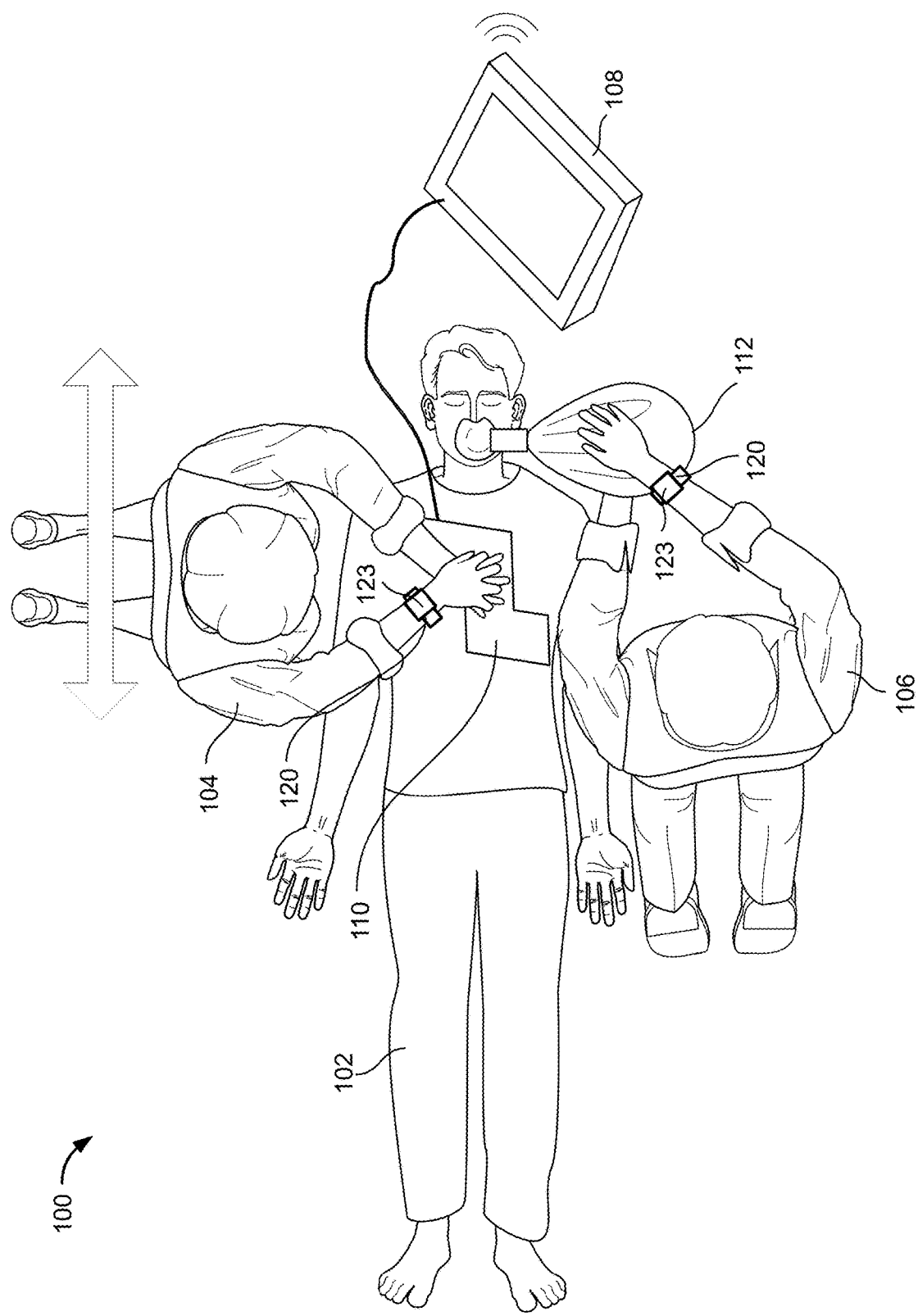
FIG. 1A is an overhead view of acute care providers performing CPR on a patient, in accordance with various embodiments.

As used herein, the singular form of "a", "an", and "the" include plural referents unless the context clearly dictates otherwise.

As used herein, the terms "right", "left", "top", and derivatives thereof shall relate to aspects of the present disclosure as it is oriented in the drawing figures. However, it is to be understood that embodiments of the present disclosure can assume various alternative orientations and, accordingly, such terms are not to be considered as limiting. Also, it is to be understood that embodiments of the present disclosure can assume various alternative variations and stage sequences, except where expressly specified to the contrary. It is also to be understood that the specific devices and processes illustrated in the attached drawings, and described in the following specification, are provided as examples. Hence, specific dimensions and other physical characteristics related to the embodiments disclosed herein are not to be considered as limiting.

According to an aspect of the present disclosure, a wearable device for use at an emergency scene is described herein. In some examples, the wearable device is worn by an emergency victim or patient. For instance, the wearable device may include one or more sensors able to sense physiological and/or motion-related information from the victim or patient. In some cases, the device is configured to process motion-based signals produced from the victim or patient to provide an estimation or indication of victim downtime (e.g., time period in which the person wearing the device has been incapacitated or otherwise immobile). The device can be further configured to provide information about the patient or victim to acute care providers to assist in treatment of the patient. In other examples, the wearable electronic device is configured to be worn by an acute care provider to assist the provider in performance of resuscitation activities, at the emergency scene. Resuscitation activities can comprise, for example, providing chest compressions, manual or automatic ventilation, monitoring and/or directing the progress of resuscitation performed by others, setting up monitoring and/or therapeutic medical devices (e.g., defibrillator, patient monitor, automated chest compressor, automated/manual ventilator, etc.), administering medications to the patient, monitoring patient vital signs, coordinating transportation of the patient from the emergency scene to a medical facility, coordinating exchange of responsibility for treatment of the patient upon arrival at the medical facility, amongst others.

In some examples, the wearable electronic device is designed to be used by a user (e.g., the patient, victim, or acute care provider) in a substantially hands free manner. Preferably, the user is able to review information displayed on a device display, output via audio or haptic output components, or otherwise provided by the device, receive feedback from the device related to performance of resuscitation activities, and control aspects of operation of the device without having to touch the device and without having to divert his/her primary attention away from the patient being treated, or other tasks that require immediate attention.

In certain embodiments, haptic feedback can be particularly effective in providing the acute care provider with information related to the resuscitation effort without detracting or distracting others from the task at hand. For instance, without adversely contributing to an otherwise chaotic or stressful environment, haptic feedback is able to signal the user in a manner that is imperceptible to other users located in close proximity. In contrast, other types of feedback, such as visual or audio prompting, may be more likely to distract and/or confuse other acute care providers with a message not intended for their particular role in the resuscitative process. As further discussed herein, the device may be programmed to exhibit a number of different patterns of haptic feedback. Multiple patterns of haptic feedback may be employed depending on the type of feedback or information intended to be provided to the acute care provider. For example, for an acute care provider performing one or more CPR activities (e.g., chest compressions, ventilation bagging, etc.), different patterns of haptic feedback may be used depending on the resuscitation activity to provide the acute care provider with guidance as to how to more effectively perform CPR, e.g., by varying technique or altering treatment. In some cases, the haptic feedback may be provided based on activity information sensed by a motion sensor integrated into the wearable device. Such haptic feedback may further be based on a comparison of the acute care provider's current performance to a target performance of the resuscitation activity.

The wearable device may further be configured to provide the user (e.g., wearer of the device) with an alert notification of a related resuscitation activity. That is, not only can changing patterns of haptic signals be used to provide resuscitation feedback, haptic signals may also be used to draw the attention of the user away from one task (e.g., the current task the user is performing and/or to which the user is attending), and toward an alert notification, which may be related to a higher priority task.

The wearable device can be a wearable computer having circuitry for monitoring performance of activities by an acute care provider and/or conditions of an emergency scene. The wearable electronic device can also be configured to receive information from external sources, such as patient monitoring devices, therapeutic medical devices, and patient physiological sensors located near the patient, as well as, from external computing devices, remote computer networks, and computer databases. The wearable electronic device can be configured to provide feedback and/or information about a patient or emergency scene to the acute care provider by output components of the wearable device, such as, for example, a visual display screen, audio output component, and haptic output component. In some embodiments, as discussed further below, the wearable electronic device may be configured to generate a diagnostic/therapeutic activity (DTA) Marker that provides a time-stamped record of a rescue event (e.g., drug infusion/administered, ventilations given, amongst others) for post-rescue event review. The device may further be configured to establish communication with an external device (e.g., defibrillator, monitor, tablet, external computer, etc.) for uploading the DTA Marker thereto and for producing an appropriate summary record of the rescue event.

In some examples, the wearable electronic device can be a multifunctional computerized device capable of performing any combination of the functions disclosed herein. In other examples, the wearable electronic device can be in communication with other computerized device(s), and configured to divide or share data processing and data transmission functions with the other device(s). For example, the wearable electronic device can be in communication with a smartphone, computer, or tabletPC by a short-range data transmitter or transceiver, such as a transceiver using the Bluetooth® data transmission protocol. In some embodiments, the wearable electronic device can be in communication with a computing device associated with a victim to receive and/or transmit information regarding the victim, for example, personal identification information of the victim, estimated location of the victim, recent motion-related activities of the victim, estimated time period in which the victim has been incapacitated and/or immobile, medical history information of the victim, physiological event information of the victim, etc. In other embodiments, the wearable electronic device may be configured to receive information from and/or about one or more defibrillators. For example, the wearable device may be able to estimate the location of the defibrillator(s) and/or of the device itself. The wearable device may further be configured to provide a summary of the status of the defibrillator(s). In some examples, data collected by the wearable device can be transmitted from the wearable device to the smartphone or computer. On the smartphone, the received data can be processed and transmitted to an external source by a short-range or long-range transceiver (e.g., a cellular or Wi-Fi transceiver, Bluetooth) integrated with the smartphone.

In some examples, the wearable electronic device can be a wrist-worn wearable electronic device, such as a smart-watch and/or activity tracking device. Smartwatches and activity tracking devices are commercially available from a number of manufacturers, any of which may be configured to operate in accordance with embodiments described herein. In other examples, the wearable electronic device can be worn on other areas of the body including, for example, a user's neck (e.g., a necklace or pendant), other regions of the arm (e.g., forearm, upper arm, shoulder) or attached to a user's shirt or jacket (e.g., a clip, pin, or broach). In other examples, a wearable electronic device can be integrated with or attached to a frame of a pair of glasses or worn about a user's head (e.g., a headband or hat).

As discussed in further detail herein, the wearable electronic device may include a number of sensors (e.g., motion sensors, accelerometers, light sensors, capacitive sensors, proximity sensors, etc.) that may be useable to measure and/or record one or more resuscitation parameters. In some embodiments, the wearable electronic device may be configured to process information (e.g., gestural motion) from the sensor(s) to identify a resuscitation activity performed or to be performed by the acute care provider based on the processed information, and may optionally provide feedback for applying an appropriate treatment protocol for the activity.

According to another aspect of the disclosure, a rescue management system including a plurality of wearable electronic devices, such as wrist-worn electronic devices, for assisting users in performing one or more resuscitation-related activities, is disclosed. The rescue management system may be configured to associate each of the wearable electronic devices with a respective role assigned to the acute care provider to assist the acute care provider in fulfilling a treatment protocol corresponding to the assigned role. In some cases, the system may be configured such that the acute care provider is only provided with resuscitation information associated with the assigned role of the acute care provider, for example, to more effectively perform corresponding treatment. By providing only the relevant information associated with the assigned role, the attention of the acute care provider to needed information may be optimized, and he/she may be spared from the possibility of information overload, alarm fatigue, inattentiveness, fixation/tunnel vision, any and all of which may commonly occur if information related to other acute care provider roles is also provided. In some embodiments, the wearable electronic device may be configured to receive information related to a particular resuscitation role assigned to the user, and may further provide resuscitation information related to the treatment protocol corresponding to the assigned resuscitation role.

The system may also be configured to receive information from the wearable electronic device(s) to provide a time-stamped record of acute care provider activities. In some cases, the system may output a code review summary having information indicative of the quality of care of each of the acute care providers based on such a record. Oftentimes, in a code review summary provided to rescue personnel for the purposes of post-rescue evaluation, there are distinct periods in which the quality of CPR will vary. However, it is difficult to delineate which acute care provider performed which specific activity during these periods. Hence, it is challenging to determine which acute care provider(s) performed high quality CPR, and which acute care provider(s) performed sub-optimal CPR. Accordingly, for various embodiments, the system may associate each of the wearable devices with a respective acute care provider, and provide a time-stamped record of activity for each particular acute care provider. Thus, it may be straightforward to determine from the final code review summary the quality of care that was provided by each acute care provider.

In some examples, the rescue management system includes medical devices and other computerized devices for coordinating activities of acute care providers at an emergency scene. For example, the system can include a rescue management apparatus configured to provide instructions, information, and feedback to wrist-worn electronic devices worn by each acute care provider at an emergency scene. The rescue management apparatus can be a dedicated electronic device, which can be portable and taken to an emergency scene, mounted to an emergency vehicle such as an ambulance, or a remote computer device accessible by wired or wireless communication from the emergency scene. In other examples, the rescue management apparatus can be a portable multipurpose electronic device, such as a laptop computer, tabletPC, smartphone, embedded system and/or other routing device.

Exemplary Emergency Scene

With reference to FIG. 1A, an overhead view of acute care providers 104, 106 performing CPR on a patient 102 at an emergency scene 100 is illustrated. The acute care providers 104, 106 are using an electronic system that instructs them in and/or provides feedback about performance of resuscitation activities. As will be discussed herein, the system can include a wrist-worn electronic device 120 worn by the acute care providers 104, 106. In some examples, a wrist-worn electronic device 120 can also be worn by the patient 102. Each of the wrist-worn electronic devices 120 can be configured to interact with other medical and computerized devices to manage or provide guidance for treatment for the patient 102 and/or to transmit patient data to another electronic device.

The acute care providers 104, 106 are in position and providing care to the patient 102. Acute care provider 104 is providing chest compressions to the torso of the patient 102. Acute care provider 106 is providing ventilation to the patient using ventilation bag 112. The acute care providers 104, 106 may be lay acute care providers who were in the vicinity of the patient 102 when the patient 102 required care, or may be trained medical personnel, such as emergency medical technicians (EMTs). Although two acute care providers are shown here for purposes of explanation, a rescue team can include additional acute care providers, who may also care for the patient 102. Additional acute care providers can perform other tasks, such as setting up medical devices or monitoring the physiological condition of the patient (e.g., checking patient vital signs). For example, one of the acute care providers can be responsible for setting up a patient monitor or defibrillator 108, which can include attaching electrodes, which can be contained in an electrode package 110, to the patient 102.

In FIG. 1A, the electrode assembly 110 is shown on the patient 102 in a normal position. The electrode assembly 110, in this example, is an assembly that combines an electrode positioned high on the right side of the patient's torso, a separate electrode positioned low on the left side of the patient's torso, and a sensor package located over the patient's sternum. The sensor package, which, in this example, is obscured in the figure by the hands of acute care provider 104 may include an accelerometer or similar motion sensor, or light sensor, which can be configured to transmit data to a computer in the defibrillator 108 to monitor performance of the chest compressions.

Once electrodes are connected to the patient, the defibrillator 108 can monitor the status of the patient to determine whether a shockable rhythm is present. The patient monitor or defibrillator 108 can communicate wirelessly with the wrist-worn devices 120 to present information or feedback to the acute care providers 104, 106, such as an indication that a shockable rhythm is present. For example, information or feedback can be visually presented on the display 123 of the wrist-worn device 120. Additionally, vibrators or audible sound generators on the wrist-worn devices 120 can provide information or feedback to the acute care providers 104, 106 concerning patient treatment or status. The defibrillator may take a generally common form, and may be a professional style defibrillator, such as the X SERIES, R SERIES, M SERIES, or E SERIES provided by ZOLL Medical Corporation of Chelmsford, Mass., or an automated external defibrillator (AED), including the AED PLUS, AED PRO or ZOLL AED 3 provided from ZOLL Medical Corporation.

In other examples, control and coordination of resuscitation activities for the patient can be performed by a computer device that is external to the defibrillator 108, such as a tabletPC or smartphone. For instance, the computer device may download and process ECG data from the defibrillator 108 or other device(s), analyze the ECG signals, perform relevant determinations based on the analysis, and control other therapeutic devices. In other examples, the defibrillator 108 can perform all the processing of the ECG, including analyzing the ECG signals, and may transmit only the final determination of the appropriate therapy to a separate device, whereupon the separate device can perform the control actions on the other linked devices.

In other examples, the acute care provided is for the emergency situation of treating a patient undergoing a stroke. In such a situation, in the pre-hospital emergency setting, the acute care provider will make an assessment of the patient using a Stroke Assessment Tool, such as the Cincinnati Prehospital Stroke Scale, the Los Angeles Prehospital Stroke Screen, as is shown in FIG. 1B, or the Miami Emergency Neurological Deficit Scale. DTA markers for each of the questions in the assessment tool (e.g., the Los Angeles Prehospital Stroke Screen shown in FIG. 1B) can be sequenced for input on the wrist-worn device. In another example, the emergency situation may be for dyspnea, where the DTA markers also include interventions like delivery of a diuretic for a diagnosis of heart failure, or a steroidal inhaler for asthma.

Exemplary Wrist-Worn Device

Having generally described devices present and activities performed at an emergency scene, the wrist-worn device 120 will now be described further. As noted above, the wrist-worn devices 120 can be a smartwatch (e.g., a computerized wristwatch with functionality enhanced beyond timekeeping) and/or activity tracking device (e.g., a fitness or exercise tracking device). An activity tracking device may include any activity tracker, such as mobile devices or software applications capable of monitoring and tracking fitness-related metrics such as distance walked or run, calorie consumption, heartbeat, quality of sleep, SpO2, amongst others. In some examples, a smartwatch or activity tracker is effectively a wearable personal data accessory (PDA) or wearable computer. A smartwatch can be in communication with other devices (e.g., medical device, defibrillator, patient monitor, sensors, communications device, smartwatch, wearable device, etc.) connected to or associated with the user to form a personal area network (PAN). A smartwatch or activity tracker can comprise a data processor, memory, input components, and output components. In some examples, a smartwatch or activity tracker can be configured to perform one or more of the following processes: collecting information from sensors located on or associated with the device; providing information to a user by output components of the device; transmitting data obtained from the sensors to an external source for additional processing and/or to be viewed by other individuals; and retrieving data from other electronic devices or computers and displaying the received data to the user, and permitting a user to input data, commands, and responses. A smartwatch or activity tracker can comprise a communications interface configured to support wired and/or wireless technologies, like Bluetooth® and/or Wi-Fi, and to communicate with other devices, such as the defibrillator 108 (shown in FIG. 1A). In some examples, a smartwatch or activity tracker can serve as a front end (e.g., a remote display) for a separate medical device, system, or network. For example, a smartwatch or activity tracker can be configured to display information generated by a medical device, such as a patient monitor or defibrillator 108 to inform the user about the status of the device or defibrillator 108.

Examples of smartwatches that may be employed according to the present disclosure include state of the art watches, or wearable devices having some or all of the functionalities of such watches, such as the APPLE Watch provided by APPLE, Inc., the PEBBLE Smartwatch (e.g., Time, Steel, Time Steel, Time Round) provided by Pebble Technology Corporation, the SAMSUNG Gear (e.g., Galaxy Gear, Gear 2, Gear 2 Neo, Gear Fit, Gear Live, Gear S, Gear S2) provided by Samsung Electronics, the ANDROID Wear provided by Google, Inc., or activity tracking devices (e.g., Fitbit), and/or other devices having similar capabilities. The smartwatch may include one or more sensors capable of or useful for measuring physiological parameters/status of the user, such as pulse, blood oxygen saturation (SpO2), blood glucose, activity, temperature, orientation, gait of the user, muscle pH, blood pressure, ECG, amongst others. Other activity tracking devices may be used such as wearable devices known to those of skill in the art, for example, devices provided by companies such as Fitbit, Garmin, Huawei, Jawbone, Nike, Misfit Wearables, amongst others.

With reference to FIGS. 2A to 2C, an exemplary wrist-worn device 120 is illustrated. The exemplary wrist-worn device 120 comprises electronic circuitry for storing and processing received data. The circuitry is enclosed in a case or housing 202. The housing 202 can be formed from a suitable protective material, such as a hard plastic or metal (e.g., brushed aluminum). The housing 202 can be a suitable shape and size to rest against the wrist of a user. For example, a bottom surface 204 of the housing 202 can be flat or curved to rest against the user's wrist. The device 120 can comprise a wrist strap 206, formed from a flexible material, such as rubberized plastic, elastic, leather, or fabric. In some embodiments, the strap is made of a flameproof material. The strap 206 can comprise a clasp or buckle 208 for holding the device 120 against the user's wrist, or a magnetic clasp or slap bracelet. The strap itself may include one or more sensors for measuring physiological parameters/status of the user, similar to those discussed above with respect to the smartwatch.

The device 120 comprises at least one visual display 123. The display 123 can be a touch screen display, allowing the user to control operation of, enter information, and interact with the device 120 by the display 123. In some examples, the display 123 can be substantially flexible and/or curved so that the housing 202 more easily rests against the wear's wrist. In addition, a curved display has an increased surface area compared to a flat display, meaning that a greater amount of information can be shown on the curved display. For example, the display 123 can be made of Indium gallium zinc oxide (IGZO), a semiconducting material. IGZO thin-film transistors (TFT) can be used in the TFT backplane of flat-panel displays (FPDs).

The touch screen may be able to sense the level of force exerted on the display surface, and respond accordingly. As the touch screen may be sensitive to distinguish between a slight tap (lower than a predetermined pressure threshold) and a more firm press (greater than the predetermined pressure threshold), the particular input command to the device may be based, at least in part, on the amount of force applied. For example, in the resuscitation context, when viewing a series of potential treatments and/or DTA Markers to input into the device, a slight tap might signify a tentative selection (e.g., signal to the device that user may make the particular selection, and may require further information to do so), whereas a firmer press may cause the device to display more information about the selection (e.g., a description of what the selection would entail) without making the actual selection. An even firmer press may cause the device to make the actual selection, for example, to input the given treatment and/or DTA Marker. In various embodiments, the touch screen may employ a series of electrodes, strain gauges and/or other force sensors along the curvature of the screen such that the force sensors are able to determine the overall pressure applied. The APPLE watch is an illustrative example of a device that employs such force sensing capability and which may be used in combination with aspects described herein.

The touch screen may also be configured to provide quick views or summaries of certain user interface displays, as desired. The APPLE watch is an illustrative example of a device that employs "glances," which may allow the user to quickly scan through summaries of commonly accessed information, and which may be incorporated in embodiments of the present disclosure. In certain instances, the acute care provider may provide an appropriate input (e.g., touch swipe, firm force touch, rotatable actuation via dial or rotary encoders, microphone input, etc.) to page through multiple glance summaries, for example, screens showing various physiological parameters (e.g., pulse oximetry, $ETCO_2$, muscle pH, blood pressure, etc.), CPR performance screens (e.g., scores indicative of CPR performance, dashboard for treating traumatic brain injury, perfusion performance indicator (PPI), amongst others), available or suggested interventional therapies/protocols, DTA Markers, amongst others. In some embodiments, only certain summary information views may be available, depending on the role assigned or otherwise associated with the device/Acute Care Provider.

The device 120 can comprise at least one input mechanism, such as physical buttons 210, for allowing additional interaction activities with the device 120. Other types of input mechanisms that can be integrated with a wrist-worn device 120 can comprise rotatable dials, keyboards, number pads, and the like. In some examples, the button 210 can be a "Home Screen" or "Main Menu" button that when pressed returns the visual display 123 to a home screen, from which various features of the device can be actuated or controlled. Other buttons 210 can comprise an acknowledgement button or "OK" button for acknowledging or confirming notifications displayed on the device 120. Other buttons 210 can be used to toggle or otherwise navigate through various user interface screens or notifications provided by the device 120. The device 120 may further provide a component that allows for the user provide input via a rotatable motion. Such a component may be provided as a rotatable dial as discussed above, or may employ rotary encoders that sense movement (e.g., circular/rotational motion, fingertip encircling the encoders) around the component, for example, to scroll through a series of options for viewing and/or selection (e.g., treatments, DTA Marker inputs, visual displays, physiological parameters, etc.). An example of an input component that senses rotary motion, as known to those skilled in the art, includes the digital crown feature provided with the APPLE Watch.

The device 120 can comprise at least one visual indicator 212 located on the device housing 202 for conveying different types of information, alerts, or notifications to the user or other personnel. For example, the visual indicators 212 can be colored lights (e.g., LEDs) that flash to signal that the device 120 has received an alert or notification.

The device 120 can comprise audio output components, such as speakers 214, for emitting audible alerts, and audio input components, such as a microphone port 216, for recording speech and/or environment noise. The device 120 can comprise at least one other port or opening that provides access to other types of sensors. For example, motion, optical, and physiological sensors can be enclosed within the housing 202. Such additional sensors will be discussed herein in connection with the schematic representation of electronic components of the device 120, as shown in FIG. 3A.

Figure 3A:
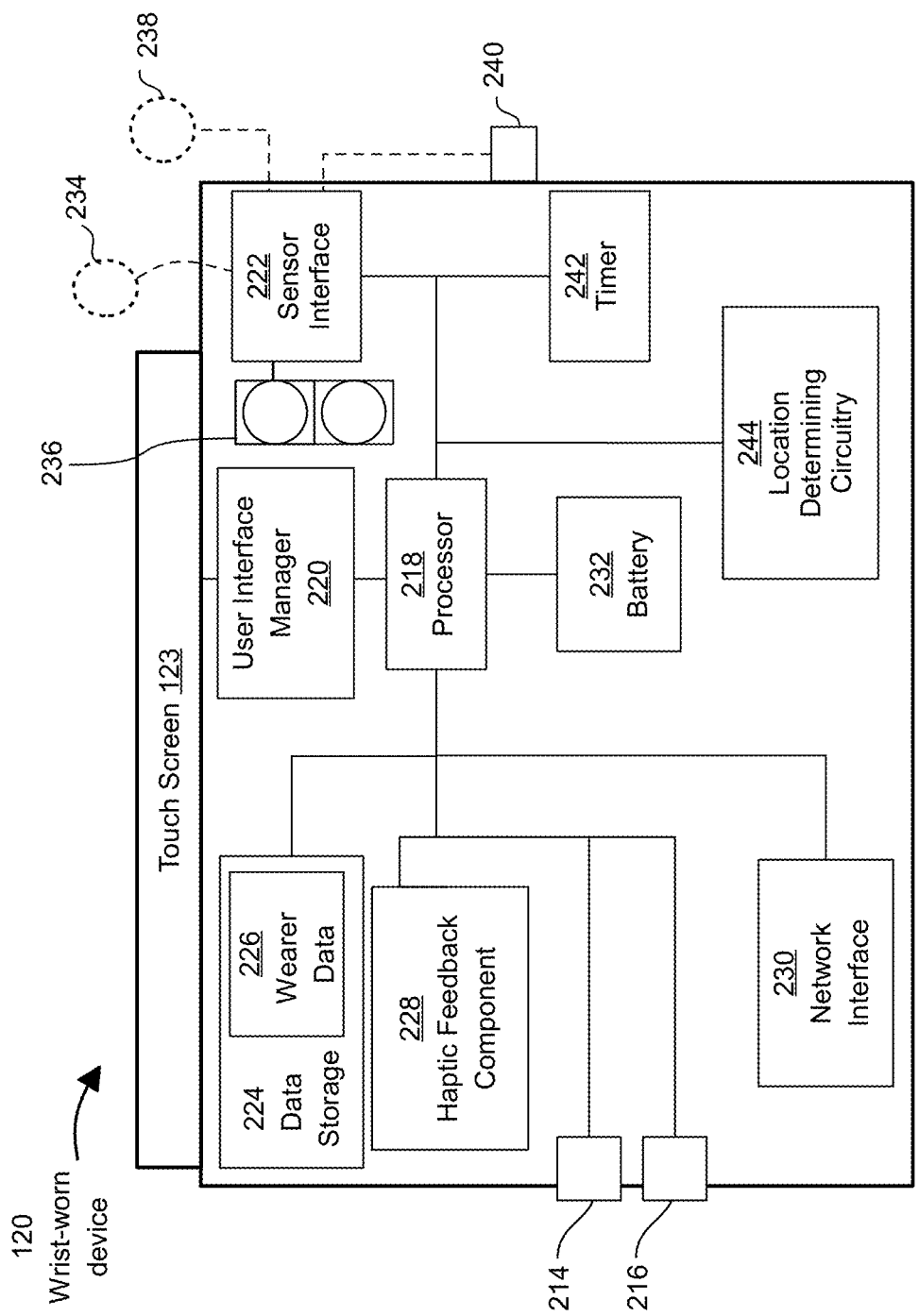
FIG. 3A is a schematic drawing of electronic components of the exemplary wrist-worn device of FIG. 2A.

With reference to FIG. 3A, the device 120 can comprise at least one of the following components: at least one processor 218; a user interface manager 220 for controlling and/or providing content to the visual display 123; a sensor interface 222 for receiving and processing information received from sensors located on or associated with the device 120; data storage 224 (which may include user (e.g., acute care provider or patient data) storage 226); a network interface 230; and a battery 232. The device 120 can comprise input components, such as the visual or touch screen display 123 and the microphone port 216. The device 120 can comprise output components such as a touch screen display (e.g., visual display 123), the speakers 214, and a haptic feedback component 228, such as a mechanical vibrating mechanism.

Sensor Interface and Sensors

The sensor interface 222 can be coupled to a variety of sensors configured to monitor a condition or activity of the user and/or to collect information about events occurring near the device 120. For example, the device 120 can comprise at least one physiological sensor 234, such as a heart rate monitor, pulse oximeter or skin temperature sensor, motion sensor 236, a pressure sensor 234 for measuring force or contact with the device 120, and a proximity sensor 238 for measuring relative position of the device 120 in space. The device 120 can comprise an optical sensor 240, such as a light sensor or digital camera for capturing static or video images of the device 120 surroundings. Although designs differ from different vendors, a digital camera usually consists of a charge-coupled device (CCD) or complementary metal-oxide-semiconductor (CMOS) imaging sensor, a lens, a multifunctional video control chip, and a set of discrete components (e.g., capacitor, resistors, and connectors). An image is recorded by the imaging sensor and can be processed by the video control chip. The processed image can be provided to the device processor 218 for further processing and, in particular, for analysis to identify items in the captured image. The recorded image can be stored on a device memory (e.g., data storage 224) to provide a record of the emergency scene and/or to be available for further processing, if required.

In some examples, the motion sensor 236 can be a single axis or multi-axis accelerometer. Single axis accelerometers can be used to determine chest compression parameters by measuring and/or providing signals that assist in determining acceleration, velocity, and/or displacement of the sensor. For example, acceleration data can be integrated to provide velocity information, and integrated again to provide displacement information. Multi-axis accelerometers, e.g., a three-axis accelerometer, can provide signals that further determine relative orientation of their respective electrode assemblies by measuring parameters indicative of motion along each axis, in addition to determining chest compression parameters. The motion sensor 236 can also include a gyroscope for determining orientation of the sensor by way of tilt or rotation.

In some examples, signals received from the motion sensors 236 can be used to evaluate motion of an acute care provider's wrist while performing chest compressions to the patient. Motion of the acute care provider's wrist can correspond to chest compression rate and/or depth. Chest compression depth and rate measurements during CPR can be made using a single sensor, for example an accelerometer contained in a housing placed on the chest of the patient at an anterior position, typically above the sternum. In such methods, the measured acceleration into the chest is twice integrated to determine chest displacement, which is used to assess depth and rate of compressions. Exemplary methods for calculating chest compression rate and depth based on a signal from a motion sensor is described in U.S. Pat. No. 9,125,793, entitled "System for determining depth of chest compressions during CPR," and U.S. Pat. No. 7,074,199, entitled "CPR chest compression monitor and method of use," each of which is incorporated by reference herein in its entirety. However, such measurements may contain error that cannot be accounted for; for example, error due to movement of a surface under the patient, patient motion and/or movement during patient transport. For example, if the patient is lying on a soft compressible surface, such as a mattress, the measured displacement can include not only the compression into the chest but also the depth of the deformation of the compressible surface. Deformation of the compressible surface can lead to an overestimation of compression depth. As another example, if the patient is in a moving ambulance the outside motion may further affect the compression measurements and contribute to error in estimating compression depth. In another example, the acceleration waveform from the sensor on the patient and the acceleration waveform from the wrist-worn sensor may be compared to determine whether full release is occurring during the CPR decompression stroke.

In order to address error and/or overestimation of depth, in some examples, the wrist-worn device 120 can comprise at least two accelerometers, as shown in FIG. 3A. The at least two accelerometers are arranged orthogonally with respect to each other to determine chest acceleration in multiple orthogonal axes. Generally speaking, while an accelerometer senses acceleration or gravity, motion or displacement of the accelerometer can be determined through a series of calculations (e.g., double integration, etc.) known to those of skill in the art.

In some examples, compression initiation and release can be identified based on signals received from proximity sensors 238 and/or optical sensors 240. For example, the proximity sensor 238 can be used to identify changes in a distance between the device 120 and a stationary object (e.g., a reference point). Similarly, images from optical sensors 240 can be used to track an absolute position of the device 120 over time, by identifying difference in elevation of the device 120 relative to objects identified in recorded images. By determining the distance or change in elevation between the device 120 and identified object, changes in the position of the wrist-worn device 120 can be identified. The identified change in position during performance of chest compressions can be used to determine chest compression rate and/or depth.

In some examples, signals received from the motion sensors 236 of the wrist-worn device 120 can be used to sense other physiological parameters caused by resuscitation activities being performed on the patient, such as ventilation rate. Ventilations (manual or automated) administered to the patient in between and/or synchronized with chest compressions can cause movement of the patient's body, particularly the patient's cardiothoracic region. Such movements arising due to the ventilations can be detectable by the motion sensors 236 on the wrist-worn device 120, provided that the acute care provider's hands are resting against the patient and that the acute care provider is not actively pressing down on the patient's chest. In that case, measurements from the one or more motion sensors 236 can include a waveform (e.g., displacement as a function of time) representative of an undulating back and forth movement of the patient's chest. The frequency of peaks and valleys of the recorded waveform can provide an indication of the rate of ventilations delivered to the patient. Based on the ventilation information from the motion sensors 236, the device 120 can provide an indication and/or feedback (e.g., audio, visual, tactile) as to whether the rate of ventilations should be faster or slower. Ventilation rate information can also be used to assist the user in synchronizing ventilations with chest compressions.

In some examples, the wrist-worn device 120 can be used to assist a user in performing resuscitation activities other than chest compressions. For example, signals received from the motion sensors 236 can be used to identify and evaluate ventilation activities being performed by the acute care provider wearing the device 120. As shown in FIG. 1A, an acute care provider can provide mechanical ventilation to a patient by a ventilation bag 112. Signals received from motion sensors 236 on the wrist-worn device can be used to identify acute care provider motion related to compression and release of the ventilation bag 112. For example, the acute care provider can open his or her hand(s) to grasp the bag 112 and can move or rotate his or her hand(s) to force air from the bag 112. The hands and/or wrists return to an initial position when the bag 112 is released, thereby allowing the bag 112 to re-inflate. The motion sensors 236 on the wrist-worn device can be configured to record and identify such up and down motion. Based on the information from the motion sensors 236, ventilation parameters such as ventilation rate and ventilation volume can be calculated or estimated. As discussed in further detail hereinafter, the information about ventilation activities performed by the acute care provider can be used by the device 120 to provide feedback to the acute care provider and, in some cases, to confirm that ventilation activities are appropriately synchronized with other resuscitation activities being formed by other acute care providers.

In some examples, the sensors, particularly the physiological sensor(s) 234 and motion sensor 236, can be used to monitor the physical condition of the acute care provider. For example, signals received from the physiological sensors 234 can be monitored to determine changes indicating that the user is becoming fatigued. Similarly, signals received from the motion sensors 236 can be monitored to assess quality and/or accuracy of resuscitation activities performed by the acute care provider. If acute care provider fatigue is identified, the device 120 can be configured to instruct the acute care provider to adjust the depth and/or rate of compressions, or to switch places with another acute care provider. If no other acute care providers are available, the device 120 can be configured to modify or adjust treatment being provided to accommodate and/or account for the fatigued acute care provider. Exemplary processes for identifying and reporting acute care provider fatigue are disclosed in United States Patent Publication No. 2015/0087919, entitled "Emergency Medical Services Smart Watch," which is assigned to the assignee of the present application and which is incorporated by reference in its entirety.

In some examples, a wrist-worn device 120 can be worn by the patient. In that case, information collected from the sensors 234, 236, 238, 240 and received by the sensor interface 222 can be used to assess events that occurred prior to arrival of acute care providers to an emergency scene. The information can be provided to the acute care providers once they arrive, to assist in determining appropriate treatment for the patient. In some examples, information from the physiological sensors 234 on the patient's device 120 can be used to determine when a physiological event (e.g., cardiac arrest, stroke, seizure, etc.) occurred and to assess, for example, how much time has elapsed since the patient has had adequate blood perfusion (e.g., determined based on analysis of the patient's heart rate). Similarly, signals received from the motion sensors 236 on the patient's device 120 can be used to identify patient movement related to an occurrence of a physiological event. For example, a heart attack or seizure could cause the patient to stagger or fall down. Signals received from the motion sensors 236 could be used to identify a patient "down time" (e.g., how much time has passed since the patient staggered or fell or otherwise became incapacitated and/or how much time has passed since the last recorded movement by the patient). In a similar manner, images captured by the optical sensors 240 can be used to identify patient position or movement. Images obtained by the optical sensors 240 can also be used to determine information about the emergency environment and to assess, for example, potential dangers at the emergency scene and/or to assist in a determination of what types of medical devices could be required to treat the patient. Examples of uses for cameras in emergency rescue are disclosed, for example, in United States Patent Publication No. 2014/0342331, entitled "Cameras for Emergency Rescue," which is assigned to the assignee of the present application and which is incorporated by reference in its entirety.

In some examples, information from sensors of the patient's wrist-worn device 120 can be used to monitor aspects of patient condition as treatment is being provided. For example, signals received from the physiological sensors 234 can be used to monitor patient heart rate and other cardiac parameters. In some examples, the optical sensor 240 can be positioned to obtain an image of the patient's skin. The recorded images can be processed by the processor 218 to identify a color, tint, saturation level, or other visually identifiable feature of the skin representative of patient physical condition. For example, skin color or saturation level can be representative of blood perfusion, body temperature, oxygen perfusion, $CO_2$ level, blood pressure, and other conditions. Recorded images of the patient's skin can be analyzed by image processing techniques to identify such conditions or levels.

Gesture Recognition Component

With continued reference to FIG. 3A, in some examples, the motion sensors 236 and/or optical sensors 240 of the wrist-worn device 120 can be used to identify gestures performed by the acute care provider, patient, or bystanders for the purpose of controlling operation of the device 120 and/or for inputting information about the resuscitation activities being performed. A gesture can be a predetermined coordinated movement performed by a user of the device 120 and identifiable by sensors (e.g., the motion sensors 236 and/or optical sensor 240) of the device. For example, the acute care provider could perform a gesture to signify what type of resuscitation activity he or she is performing or will perform (e.g., turning palms downward and mimicking a pushing motion can represent a chest compression, turning wrist upward in a manner that signifies compressing a ventilation bag). Other gestures can be used to identify a particular acute care provider or patient, such as shaking of the wrist, moving the watch in a particular gestural pattern (e.g., circular, figure eight, back and forth motion, outlining a recognizable shape pre-input into memory), performing a correlation analysis (e.g., correlating sensor data with resuscitation action(s)), to identify a particular activity or otherwise convey a signal to a computer processor that is associated with a certain action (e.g., switching or adjusting the rescue activity, signaling the device to transmit and/or receive information, etc.). For example, an acute care provider can perform a predetermined gesture to identify himself or herself (e.g., move the watch in a pattern associated with the acute care provider or perform a hand gesture associated with the acute care provider, such as holding fingers in a predetermined manner, that can be identified by the motion sensor or captured by the camera), thereby allowing the device 120 or an external device in communication with the wrist-worn device 120 (such as an acute care provider management apparatus) to associate the device 120 with a particular acute care provider. In other examples, gestures can be used to interact with the user interface of the device 120. For example, certain pre-programmed gestures can be used to scroll through information displayed on the visual display 123 or to toggle through different screens of the user interface. In another example, acute care providers equipped with a wearable device might be required to raise their hand(s) to indicate an all clear has been achieved which then allows for a shock to occur.

User Interface and Visual Display

With continued reference to FIG. 3A, the user interface manager 220 can be integrated with and coupled to output components of the device 120 comprising the visual display 123, haptic feedback mechanism 228, and/or visual indicators 212 (shown in FIGS. 2A and 2C). The user interface manager 220 can be configured to provide user interface screens on the visual display 123, which allow the user to receive information from and/or to control operation of the device 120. For example, text, images, and animations for providing notifications, alerts, and feedback to the user can be provided on the visual display 123. In some examples, the user interface manager 220 is implemented as a software component that is stored at data storage 224 and executed by the processor 218. In other examples, the user interface screens can be received directly from an external computing device, such as a smartphone or another medical device, such as the defibrillator 108 (shown in FIG. 1A). In that case, the user interface manager 220 receives the user interface screens from the external computing device and controls presentation of the received screens on the visual display 123. In some examples, the user interface manager 220 can also control other output components of the device 120, such as the speakers 214, tactile and/or vibration output elements (e.g., haptic feedback component 228), and the visual indicators 212 (shown in FIGS. 2A and 2C). Beneficially, since the device 120 is often positioned on the user's wrist, the display 123 and other output components generally remain within the field-of-view of the user as resuscitation activities are being performed. Accordingly, the user is not required to look away from tasks being performed to view information shown on the display 123.

In some examples, visual feedback on the visual display 123 and controlled by the user interface manager 220 can comprise virtual visual indicators representing how the resuscitation activity is being performed. In a simple example, the display 123 can flash a text instruction, such as displaying the word "Compress" to signal the user to begin a chest compression or displaying "Ventilate" or "Breath" to signal the user to perform a manual ventilation. In some examples, visual feedback can be provided to the user to indicate whether measured values such as compression rate and depth are within a predetermined range. In some examples, the displayed information about chest compressions and ventilations being performed by acute care providers can include a performance indicator (PI). The PI may be provided as a shape (e.g., a diamond) or number displayed on the display 123. An amount of the shape that is colored or shaded (e.g., the fill amount) or number can differ over time to provide feedback about both the rate and depth of the compressions being performed. In some examples, the fill amount can be adjusted to account for a degree of chest compression release, measured ventilation rate and volume, and other resuscitation activities related to perfusion of oxygenated blood for the patient. When CPR is being performed adequately, the entire indicator can be filled to indicate good quality chest compressions. As the rate and/or depth decreases below acceptable limits, the amount of fill lessens. Beneficially, the PI may provide a concise visual indication of the quality of the CPR such that the acute care provider can aim to keep the PI completely filled. An exemplary PI visual indicator that can be displayed on the visual display 123 of the device 120 is described in U.S. Pat. No. 8,880,166, entitled "Defibrillator Display," which is incorporated by reference herein in its entirety. Alternatively or additionally, the PI can be a number, for example, a "5" on a scale of 1 to 10, where 10 is the target for adequate CPR.

The user interface screens shown on the visual display 123 can also include various notifications and alerts for the user. For example, notifications about when a particular aspect of a resuscitation activity or treatment protocol should be performed can be shown on the visual display 123. In addition, information about the patient being treated, the emergency scene, and/or about the location or role of other acute care providers can be accumulated by the user interface manager 220 and shown on the visual display 123.

Audio Feedback Component

The device 120 and/or user interface manager 220 can also provide verbal and/or non-verbal information and feedback by the audio output components, such as the speakers 214. As one example, the device 123 can emit a sound through the speaker 214 in the form of a metronome to guide an acute care provider in proper performance of resuscitation activities, such as a rate of applying chest compressions and/or manual ventilations to a patient. For example, in the case of providing chest compressions to a patient, audio feedback, such as a beep or tick, can be emitted from the speaker 214 when the acute care provider should initiate a chest compression to help the acute care provider to maintain rhythm to provide chest compressions at a desired rate. Sounds emitted from the speakers 214 can also notify the user of device alerts. For example, an audio alert could issue at a predetermined time to instruct the user to switch places with another acute care provider or to perform another type of resuscitation activity. Also, verbal commands can be issued to the acute care provider, such as "Check Pulse", "Breath", or for CPR, "Faster" and/or "Slower".

Haptic Feedback Component

With continued reference to FIG. 3A, information and feedback can also be provided to the user by the tactile or haptic feedback component (e.g., haptic feedback component 228) of the device 120. Providing haptic feedback, rather than displaying text or images on the visual display 123, means that the acute care provider is not required to look away from the patient to receive information and/or feedback from the device 120. Additionally, providing haptic feedback, rather than audio alerts or message, is less likely to distract other acute care providers in the area, who may also be wearing devices that emit audio alerts. Accordingly, haptic feedback can be well-suited for providing information to an acute care provider in an emergency environment. Haptic feedback can refer to mechanical stimulations applied to a user for recreating a sense of touch from forces, vibrations, and/or motion generated by the device 120.

Haptic feedback can include any number of intensities or vibration patterns to convey different types of information to the user. In various embodiments, the device may employ a haptic feedback component similar to the Taptic Engine provided in the APPLE Watch, as known to those of skill in the art, which includes a compact linear actuator that provides the ability to adjust the pattern (e.g., frequency, intensity) of vibration/touch feedback. Such an actuator may include a spring and magnet for manipulating a mass coupled thereto. Any suitable actuator may be used, though, in some cases, linear actuators may be advantageous over rotating mass vibration motors in that they typically consume comparatively less energy and exhibit less latency upon actuation.

Figure 3B:
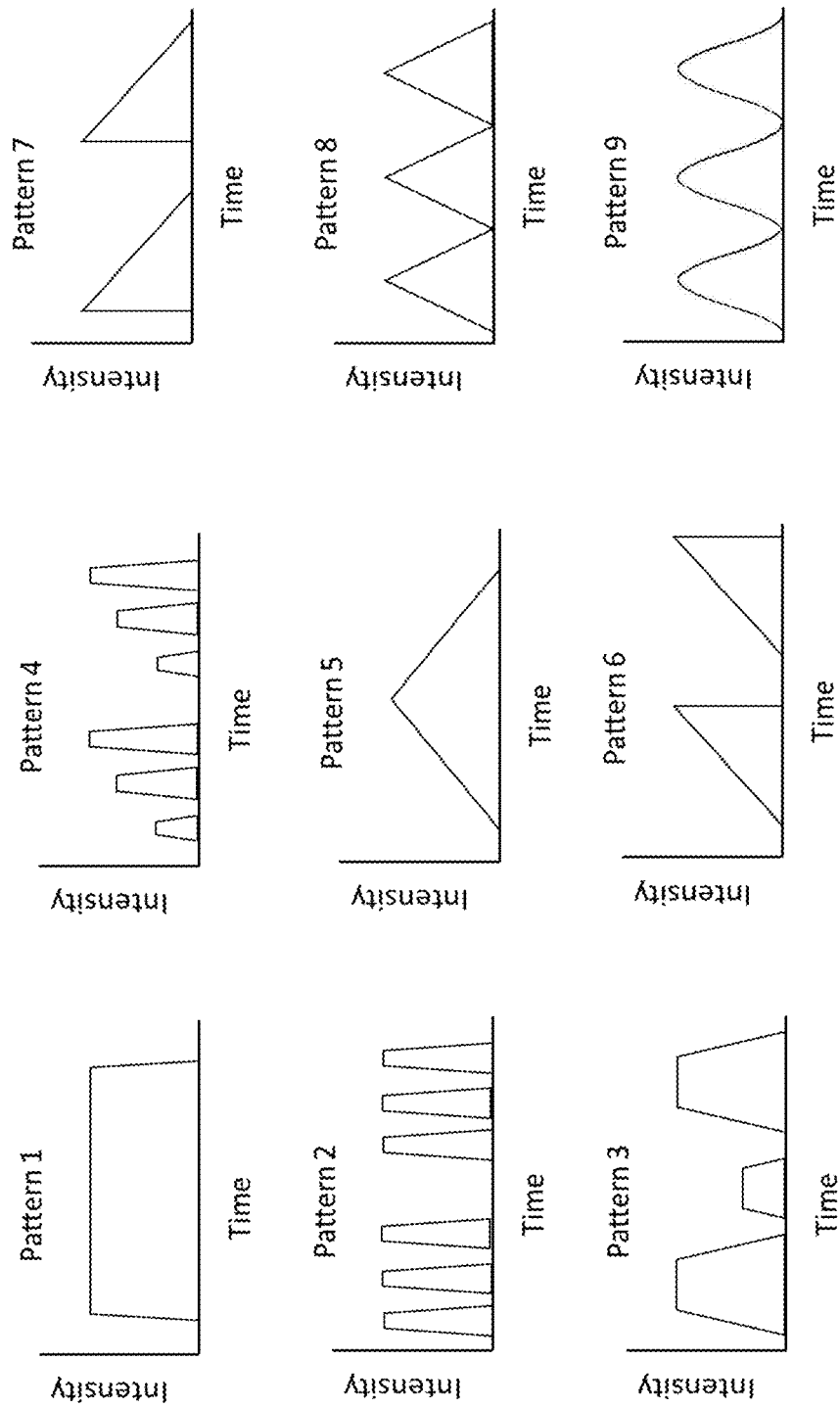
FIG. 3B is a series of graphs illustrating haptic patterns that can be emitted from exemplary wrist-worn devices.

Accordingly, the device 120 may employ any suitable haptic pattern pre-configured and/or programmed therein, which may be adjusted as appropriate. For example, depending on the type of feedback or notification to be provided to the user, the haptic pattern(s) may increase or decrease in intensity, and may exhibit any appropriate regularity or irregularity (may or may not be periodic). FIG. 3B depicts a number of exemplary haptic patterns that may be used by the device for communicating feedback and/or notifications to the user. As shown in FIG. 3B, Pattern 1 is a standard vibration pattern where the device 120 vibrates at a set intensity for an extended period of time. Pattern 2 involves a series of vibrations at the same intensity for different frequencies, in which clusters of three vibrations occurring at high frequency are separated by a comparatively lower frequency vibration. Pattern 3 is a pattern that exhibits alternating intensities of vibration. Pattern 4 involves clusters of three vibrations occurring at high frequency, similar to that shown for Pattern 2, except there are also three distinct intensities of vibration for each cluster, in escalating fashion. Pattern 5 is a triangular haptic pattern of gradually increasing intensity over time to a peak followed by a gradually decreasing intensity. Pattern 6 involves a saw tooth haptic pattern where the intensity of vibration increases up to a certain level and then abruptly ceases. Pattern 7 is also a saw tooth haptic pattern except, in this case, upon commencing, the vibration is most intense, followed by a gradual decrease in intensity. Pattern 8 is a haptic pattern characterized by a repeating triangular waveform. Pattern 9 is a haptic pattern that exhibits a sinusoidal behavior. It can be appreciated that any number of haptic patterns may be used according to embodiments described herein, as this figure is only exemplary in nature. For example, while each of the patterns shown in FIG. 3B are time dependent, for various embodiments, haptic patterns are not functions of time and are able to provide real-time feedback based on user actions, unbounded by time constraints. That is, the haptic pattern of the device may change according to the feedback or notification to be provided to the user.

In some examples, certain patterns may include one or more haptic taps in combination with ascending and/or descending tones from the speaker 214 (shown in FIG. 3A). For instance, one or more taps may be provided with a series of tones output together and/or in sequence from the speaker 214. As an example, a haptic tap in combination with multiple tones forming an ascending major chord may signify encouragement that an activity has successfully been completed. In another example, a haptic tap in combination with descending tones (e.g., a three-note octave providing two high notes and one low note) may indicate that the current activity should be altered or adjusted. A series of multiple, low duration (e.g., less than 0.5 seconds) taps and/or tones may indicate that an activity should be repeated or continued. A haptic tap having a relatively strong force (e.g., greater than the default level tap) may signal a user to begin an activity. A series of multiple haptic taps (e.g., 2-3 haptic taps) of relatively strong force and short duration (e.g., less than approximately 0.5 seconds) may indicate that the user is to discontinue the current activity. However, it can be appreciated that any suitable pattern of haptic output, which may or may not be in combination with other forms of feedback, may be employed for notifying and/or guiding the user through resuscitation. Such haptic feedback may be provided based on information produced from a motion sensor. For example, motion-based information can be used for determining how a user may be notified, signaled, or otherwise guided. Such a system may be in contrast, or advanced in comparison, to systems that are configured to generate periodic vibrations for the purpose of providing a metronome for administering chest compressions to a patient Haptic feedback can be used to assist the user in operating the device 120. For example, haptic feedback can be used in association with the user interface and touch screen display 123 to assist the user in navigating user interface screens and/or toggling through different screens. For example, a vibration pattern emitted by the haptic feedback mechanism 228, such as haptic patterns similar to the patterns shown in Patterns 2 or 4 of FIG. 3B, can indicate that the user has navigated to the bottom (e.g., limit, boundary) of a screen shown on the display 123. Other haptic outputs can indicate that the user has swiped or toggled to the end of a series of screens and/or has reviewed all information presently being displayed by the user interface manager 220.

As noted herein, the haptic feedback may be provided to the user according to any suitable pattern and change from one pattern to another, for providing instructions or guidance for the user in performing a particular resuscitation activity. In some cases as discussed below, the haptic feedback may change from one particular pattern to a different pattern so as to produce an intuitive feel to the user that a depth limit has been reached during chest compressions, and so the user may be more inclined to release. For example, such haptic feedback may be provided in the form of a sudden increase in the intensity of haptic force and/or at a relatively high (or increasing) frequency, intended to be felt by the user as a signal or alarm to stop the compression downstroke motion. In some embodiments, haptic feedback is provided in combination with other forms of feedback, such as audio (e.g., tone, voice, pitch, etc.), visual (e.g., images, text, etc.), amongst others.

In some examples, haptic feedback from the haptic feedback component 228 can be used to guide performance of resuscitation activities by the user and/or to provide information to the user about the quality and/or accuracy of resuscitation activities being performed on the patient. For example, haptic feedback can be provided for performance of chest compressions or manual ventilation to the patient. The feedback can be periodic or aperiodic and provided to instruct an acute care provider in the manner in which compressions or ventilations are given. Similarly, haptic feedback can be provided both when the acute care provider should begin a compression or ventilation and when the acute care provider should release the compression or ventilation. Accordingly, haptic feedback can be a supplement to or replacement for the audible metronome emitted from the speakers 214. Beneficially, since the haptic feedback is felt directly at the acute care provider's hand and/or wrist, the acute care provider may find it easier to respond to (e.g., keep pace with) haptic feedback as compared to visual or audio feedback, which must be seen or heard to be followed. In some examples, haptic feedback can be provided along with other types of feedback (e.g., audio and/or visual) to convey additional information to the user. For example, haptic feedback can be provided to instruct the user when to begin and when to release a compression, and can be provided with increasing intensity depending on the nature of the instruction. For instance, if it is determined that the acute care provider has been idle in giving chest compressions (or other recommended therapy) to the patient for a substantially long period of time and should be doing so, then the haptic feedback mechanism may provide multiple reminders to the user with increasing intensity until compressions (or the other therapy) commence. Audible feedback can be provided to inform the acute care provider that chest compressions being performed are not in accordance with target values. For example, the device 120 can emit an audible instruction for the user to "Press Harder" or "Speed Up" if compression depth or rate is not within the target range.

Haptic feedback can also be used to provide information to acute care providers for coordinating activities performed by different acute care providers. For example, a first type of feedback, such as pulsed visual, audible, or tactile feedback may be provided to guide a user in performing CPR. The pulse feedback can be interrupted and replaced with a different type of feedback, such as constant sound or vibration, to indicate that an acute care provider is to stop performing the particular component of CPR and let another acute care provider takeover. Where there are three or more acute care providers, the third acute care provider may be resting while resuscitation activities are being performed by the first two acute care providers. When an acute care provider change is needed, the device 120 worn by the third acute care provider can vibrate, indicating that he or she should take over chest compressions or ventilation. In some examples, the wrist-worn device 120 can instruct the acute care provider which resuscitation activity to begin performing. In other examples, the wrist-worn devices 120 can be programmed according to the manner in which acute care providers decide to rotate and further account for the resuscitation activity taken by each acute care provider. In some cases, the device 120 can be configured to identify the type of resuscitation activity being performed and to provide appropriate feedback. Similarly, it is recognized that a rotation can change during a rescue (e.g., an acute care provider may initially provide chest compressions as part of a three-person rotation and may then bow out and just provide ventilation while the other two acute care providers rotate on chest compressions).

In some examples, an amount of information that can provided by haptic feedback can be substantially increased by changing the pattern (e.g., intensity and/or frequency) of vibrations emitted from the device 120. Similar to Pattern 2 (shown in FIG. 3B), a pattern of haptic feedback can refer to a recognizable repeated sequence of pulsed vibrations of varying duration. In other cases, a pattern of haptic feedback can refer to a repeated sequence of vibrations of varying intensity, such as that shown in Patterns 3-9. In some examples, similar to Pattern 6, the haptic feedback component 228 can be configured to be a low intensity vibration to encourage the acute care provider to initiate a resuscitation activity and a higher intensity vibration to encourage the acute care provider to cease, adjust, or change the resuscitation activity. However, it can be appreciated that the intensity of haptic feedback may vary depending on user motion, and not necessarily time elapsed. Accordingly, for example, for an acute care provider providing chest compressions to the patient, the haptic feedback mechanism can provide a low level of vibration instructing the acute care provider to initiate a compression by pushing downward on the patient's chest. The low level vibration can continue until a target depth is reached. Once the target depth is obtained, the haptic feedback component 228 can emit a higher intensity vibration signaling to the acute care provider that the compression should be released. The higher intensity vibration can continue until the motion sensor 236 senses or determines that the acute care provider releases the compression. For example, the higher intensity vibration may intuitively feel to the user that a boundary, wall or limit has been reached during the compression, and so be more inclined to release.

In a similar manner, a low intensity vibration can be provided by the haptic feedback component 228 to instruct the acute care provider to compress the ventilation bag 112 (shown in FIG. 1A). The low intensity vibration can continue until a target ventilation volume is expelled from the bag 112. Once the target ventilation volume is expelled, the haptic feedback mechanism 228 can provide a higher intensity vibration to inform the acute care provider to release the bag 112. In some examples, a haptic feedback can be used to prompt an acute care provider to administer medication.

In some examples, haptic feedback can be implemented to provide alert notifications for the user in the resuscitation context. For example, the device 120 can vibrate according to a specific pattern when the user should check on a particular resuscitation activity that is not necessarily germane to the task at hand. For example, the user may be an acute care provider performing chest compressions or another resuscitation activity, and receiving appropriate feedback (e.g., audio, visual, haptic) on his/her performance. Though, amidst this particular resuscitation activity, the user may receive an alert notification requiring the user to divert his/her attention away from the current activity (e.g., chest compressions) and to consider the content of the notification. Such an alert may be of a relatively high importance for the user to pause activity. So as not to interfere with the resuscitation efforts of others, the alert notification may be provided from the device according to a suitable haptic pattern. For example, the alert may involve a score indicating to the user that the quality of chest compressions given is sub-optimal, and may further include a directive for the user to allow someone else to step in and take over the resuscitation activity. As also discussed herein, if the haptic alert is initially insufficient to gather the user's attention, the device may escalate the feedback (e.g., increasing intensity, frequency of haptic force and/or involving other types of feedback, such as audible or visual alerts) so that the user may be more likely to respond.

For a user who is overseeing a number of acute care providers to coordinate rescue efforts, the alert may provide a notification for the user to direct his/her attention toward a specific area of activity. For instance, the supervisor may receive an alert notification that this particular acute care provider is in need of assistance or replacement if one of the acute care providers being supervised is identified as performing below standards (e.g., due to fatigue or lack of skill). Accordingly, the device may provide an alert notification in the form of a haptic feedback pattern so that the user is aware of the situation. In some embodiments, the haptic feedback pattern may be specific to the particular notification to be provided. For example, the haptic pattern may be sufficiently specific that upon receiving the notification, without looking at the device 120 or referring to any other device/component, the supervisor may immediately know which acute care provider or what activity (e.g., chest compressions, ventilations, etc.) to inspect. Such haptic patterns may be pre-configured on the device 120 or programmed (e.g., manually entered) by a user or system to correspond to specific resuscitation related notifications. For instance, a certain pattern of haptic feedback may be provided to signal the user to switch resuscitation activities (e.g., switch between chest compressions and ventilations). Other patterns of haptic feedback may be provided to alert the user to view a screen, listen to an audio prompt, or provide explicit instructions related to performance of one or more resuscitation activities. As noted above, the haptic patterns may be specifically tailored such that the user is immediately aware of the concern.

Communications Circuitry

With reference again to FIG. 3A, the network interface 230 can be a transmitter or transceiver capable of bidirectional communication between the device 120 and external sources, such as a computer, database, remote sensors associated with the patient, and/or with other wrist-worn devices. In some examples, the network interface 230 comprises a short-range data transmitter or transceiver using Bluetooth® or Zigbee protocols. For example, the device 120 can be configured to wirelessly communicate with one or more sensing or monitoring devices associated with the acute care provider or patient to form, in effect, a personal area network (PAN). Sensing and monitoring devices associated the patient can include, for example, a blood pressure sensor, pulse oximetry sensor, skin or internal body temperature sensor, and others having wireless transceivers for actively or passively transmitting data that can be received by the wrist-worn device 120. Similar sensing and monitoring devices can be provided to assess physical status of the acute care provider to determine, for example, acute care provider fatigue.

In some examples, the network interface 230 can be configured to transmit data to an intermediate device having long-range data transmission capabilities. The intermediate device (e.g., a smartphone, tablet, laptop computer, or PDA) can receive and, in some cases, perform additional processing on the received data. The data can then be transmitted to an external electronic device, computer network, or database using the long-range data transmission capabilities of the intermediate device.

In some further examples, the network interface 230 can comprise circuitry for long-range data transmission directly from the device 120 itself. Long-range data transmission can be performed by a long-range data transmitter or transceiver, for example a WiFi transmitter or a cellular transmitter (e.g., 3G or 4G enabled systems). Data collected by the device 120 can be sent to external sources by the long-range data transmitter or transceiver.

Timer and Internal Clock

In some examples, the device 120 can comprise electronic circuitry, such as an electronic clock or timer 242, for tracking passage of time (e.g., during a resuscitation activity) and/or for determining a current time. The timer 242 can be enclosed within the housing 202 and in communication with the processor 218. The timer 242 can be configured to communicate with an external electronic device, such as a smartphone or PDA, or external computer network to determine a current time. The current time can be displayed on the visual display 123 by the user interface manager 220. For example, the display 123 can comprise, numbers, icons, or images resembling the face of a mechanical watch for displaying the current time. In addition, the current time can be automatically associated with data received from the one or more sensors on or associated with the device 120. For example, the sensor interface 220 can be configured to timestamp received data. Timestamps can be used to correlate the received data obtained by the device 120 with data recorded from other devices, such as the defibrillator 108 (shown in FIG. 1A). The time-stamped data can also be correlated with data obtained from other wrist-worn devices 120 to provide a time-stamped record of multiple resuscitation activities being performed for the patient. The timer 242 can also be used to determine a duration of certain events during the rescue. For example, the timer 242 can measure an amount of time from occurrence of a physiological event, such as since the patient experience a heart attack or since the patient's a last identifiable movement. Also timing information from the timer 242 can be used to guide when scheduled treatment events should be provided. For example, a treatment protocol may include administering a particular medication to the patient at specific time intervals, or different medications at specific time intervals. The timer 242 can automatically track a period of time from administration of the medication, and provide a notification when the next dose should be provided. Or, the timer 242 can track the time that has elapsed during which chest compressions are being administered, similarly with ventilations. Accordingly, based at least in part on the time of events, the device 120 may provide the user with an indication of which activity should be performed at any given time.

Location Determining Circuitry

In some examples, the device 120 can also include location determining circuitry 244, such as global positioning system (GPS) circuitry and/or a cellular transceiver. Information from the cellular transceiver can be used to triangulate a device position based on readings from associated stationary access points (e.g., cellular towers). Other communications transceivers, such as a WiFi transceiver, can be used to identify device 120 location based on known positions of WiFi hotspots or access points. The location information can be used, for example, to determine a location of a patient in need of medical assistance or to determine an acute care provider's distance from an emergency scene. Location information can be used to associate particular acute care provider(s) with emergency scenes (e.g., to identify which acute care providers are present and/or which acute care providers performed which tasks). Location information can be used to determine how close an acute care provider or user is to stationary medical equipment such as, for example, a wall-mounted automated defibrillator (AED). In some examples, location information obtained from the location determining circuitry 244 can be stored in device memory (e.g., data storage 224) along with associated timestamps to provide a record of the location of the device 120 over time.

Battery/Power Supply

With continued reference to FIG. 3A, in some examples, the device 120 can be powered by a battery 232, located in the housing 202. The battery 232 can be rechargeable and, in some cases, can be removable from the housing 202 to enable the user to swap a depleted (or near depleted) battery 232 for a charged battery. Alternatively, the battery 232 can be non-removable. In that case, the device 120 can be connected to a power source by a power cable, such as a universal serial bus (USB) cord, to recharge the battery 232. Or, the battery may be charged wirelessly (e.g., inductively), as known to those of skill in the art.

Processes for CPR Feedback and Quality Assessments

Having described the structure and electronic components of the wrist-worn device 120, methods and processing routines for providing feedback to an acute care provider wearing the device 120 will now be further discussed. The feedback can be substantially real-time feedback for guiding an acute care provider in performance of a resuscitation activity. The feedback can be modified or selected based on motion information received from motion sensors associated with the device 120. For example, the feedback can include information about whether resuscitation activities are being performed substantially correctly. In other examples, feedback can comprise a first type of feedback for a first aspect of a resuscitation activity and another type of feedback for a second aspect of the resuscitation activity. In other examples, feedback can be provided in the form of a quality assessment provided after cessation of the resuscitation activity to provide an indicator (e.g., a score or metric) related to an overall quality of the resuscitation activities performed for the patient. In still other examples, feedback can comprise one or more alert notifications to provide information to acute care providers about various aspects of resuscitation events.

Acute Care Provider Feedback

Figure 4:
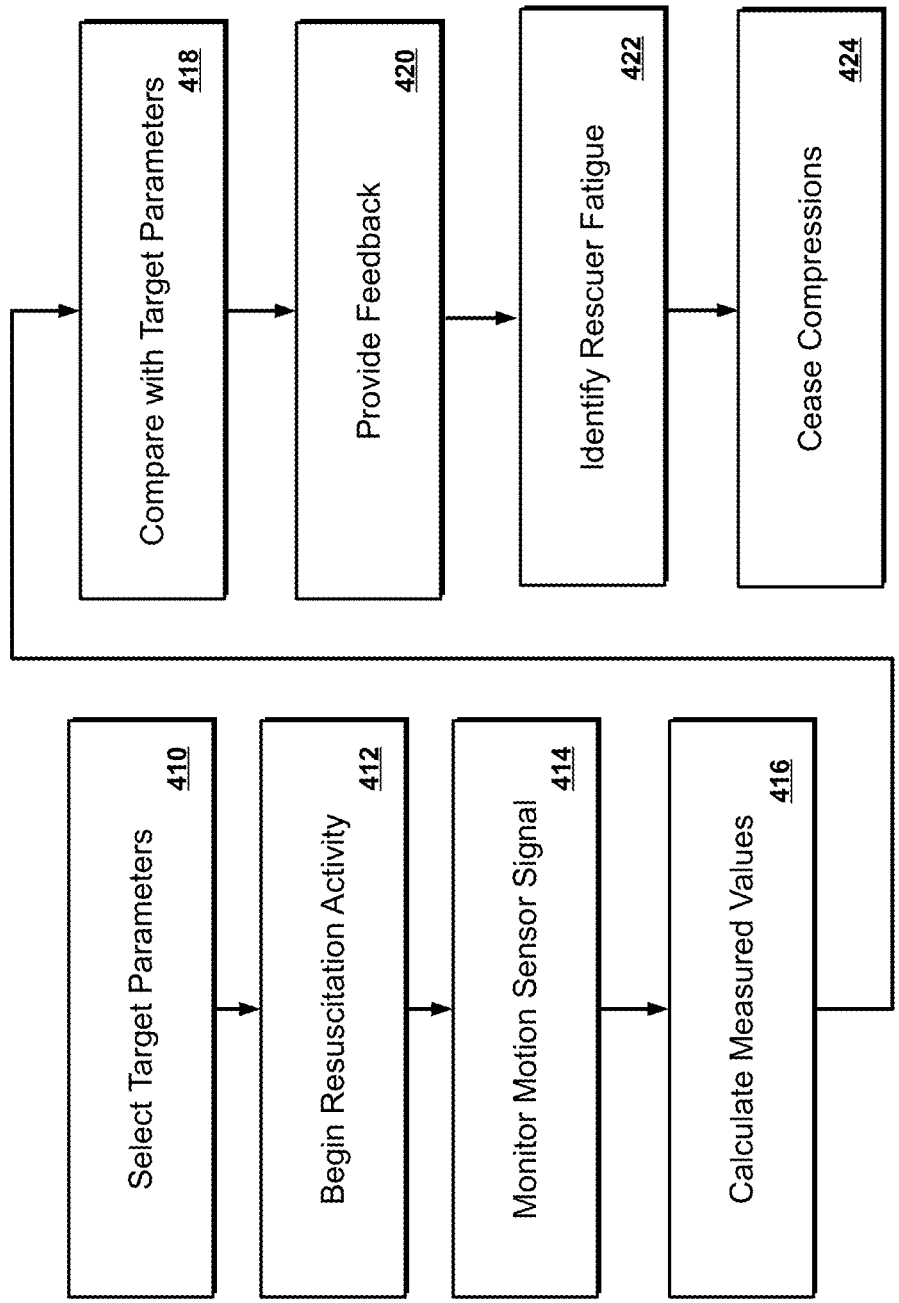
FIG. 4 is a flowchart of an exemplary process for providing feedback about performance of resuscitation activities to an individual wearing a wrist-worn device.

With reference to FIG. 4, a flowchart for an exemplary process for providing feedback to a user (e.g., an acute care provider at an emergency scene) of the wrist-worn device 120 (shown in FIGS. 1-3A) is illustrated. The feedback can be provided by one or more of the output components of the device 120 including, for example, the visual display 123, audio feedback component, such as the speaker 214, and/or haptic feedback component 228.

As shown at box 410, target parameters for a resuscitation activity being performed are selected. For chest compressions, target parameters can include compression rate, depth, and compression cycle duration. In some examples, a preferred chest compression depth is about 2.0 inches, and an appropriate range for chest compression depths is between about 2.0 inches and 2.4 inches, according to the 2015 Guidelines by the American Heart Association (AHA) for Cardiopulmonary Resuscitation (CPR) and Emergency Cardiovascular Care (ECC). Target chest compression rate according to the AHA Guidelines can be between about 100 compressions per minute (cpm) and 120 cpm, and preferably about 105 cpm. These targets and ranges can be varied depending upon a selected protocol. For ventilation, target parameters can include ventilation rate and volume. Target ventilation rate may be about 10 ventilation breaths per minute (e.g., approximately 30 compressions for every 2 ventilation breaths) for adults and about 20 ventilation breaths per minute (e.g., approximately 15 compressions for every 2 ventilation breaths) for infants. Target parameters can also relate to synchronization or sequences of chest compressions and ventilations. For example, as noted, the device 120 can be configured to direct acute care providers to provide a number of compressions (e.g., about 30 compressions, or another suitable number) and then to pause compressions while delivering a specified number of ventilations (e.g., 2 ventilations). Target parameters can be predetermined and stored in memory located on the device 120, entered manually by the user prior to beginning the resuscitation activity, or automatically calculated by the device 120 based, for example, on characteristics of the patient or acute care provider. For example, target compression depth can be based on a size or weight of the patient. In other examples, target compression rate and depth can be selected based on skill of the acute care provider. In other examples, target parameters can be received from an external source, such as an external computer or another medical device. For example, the target parameters can be based on a treatment protocol received from another medical device, such as a defibrillator, wearable defibrillator (e.g., LifeVest Wearable Defibrillator provided by ZOLL Medical) or ventilator, or from a remote computer, computer network, or from a central server.

As shown at box 412, the device can provide a notification or indicator instructing the acute care provider to begin performing the resuscitation activity. As described herein, the resuscitation activity can be preselected (e.g., the resuscitation activity to be performed is stored on the device and/or known to the acute care provider). Alternatively, the resuscitation activity to be performed by a respective acute care provider can be assigned to the acute care provider at the emergency site either manually (e.g., by another acute care provider or team leader) or based on a determination by a computing device, such as the rescue management apparatus. In various embodiments, the acute care provider may need to perform multiple resuscitation activities (e.g., compressions, ventilations, drug infusion, administrative activities, etc.) in succession. Hence, the device may provide notifications based on the sensed and/or input progress of the resuscitation, or based on a timer that keeps the acute care provider(s) on schedule with respect to the sequence of events and/or interventions that are desired. Such a schedule of notifications may be based on a particular mode or role to which the device may be set. For example, each rescue role may have a schedule of timed events corresponding to that particular role.

In some examples, the notification or indicator can be in the form of haptic feedback according to a preselected haptic pattern. As discussed above, the wrist-worn device is capable of providing haptic feedback according to a variety of patterns and intensities (e.g., a saw tooth pattern, a series of haptic pulses in quick succession followed by a pause, and/or haptic feedback in association with another type of feedback, etc.). In some instances, the acute care provider may know that a notification with a first haptic pattern is an instruction to begin performing a first resuscitation activity and haptic feedback with another haptic pattern is an instruction to perform another resuscitation activity. In a similar manner, an acute care provider may know that a notification from a first output component (e.g., audio output) is an instruction to perform one type of resuscitation activity, while a notification from another output component (e.g., haptic feedback) corresponds to an instruction to perform a second type of resuscitation activity.

As shown at box 414, performance of the resuscitation activity can be monitored based on motion-based signals received from the motion sensor 236 (shown in FIG. 3A). For example, the received signal can be monitored and processed to identify motion and/or acceleration of the device 120. Based on the processed signal, as shown at box 416, the device can be configured to determine measured values for the resuscitation activity being performed. As shown at box 418, the measured values are compared to the target parameters.

As shown at box 420, based on the comparison of the measured values and target parameters, feedback is provided to the acute care provider with an output component of the device. The feedback related to the comparison between the measured values and target parameter is, desirably, easily distinguishable from other types of notifications emitted by the device 120 (e.g., the notification informing the acute care provider to begin the resuscitation activity). In some examples, feedback can be provided by the visual display and/or speakers of the device. For example, for chest compressions various visual displays can show the acute care provider information about chest compression depth and, in particular, whether chest compressions being performed are within the target range. As further discussed herein, feedback can also be provided in the form of haptic feedback with varying haptic patterns.

In some examples, a haptic pattern, such as intensity of the haptic feedback, can vary based on information received from motion sensors associated with the wearable device 120. For example, haptic patterns emitted from the device 120 can vary based on relative correspondence between the measured values and the target parameter values. Accordingly, in the case of chest compression rate, the haptic feedback component can vibrate with a noticeably high or higher level of intensity if the rate of compressions being performed is far from the target rate. However, the intensity of the vibration can decrease if the rate of chest compressions being performed is closer to the target rate. If the measured chest compression depth/rate is within the target range, the device may emit another haptic pattern to encourage the acute care provider to continue chest compressions at the present depth and rate. In other examples, a particular vibration pattern can be selected to correspond to a particular aspect of the resuscitation activity. For example, the device 120 could vibrate according to a first pattern to inform the acute care provider to initiate a chest compression and, once a target depth is reached, vibrate in another pattern to signal that the acute care provider should release the compression. For example, the wearable device 120 can be configured to provide a low intensity vibration to encourage the acute care provider to begin a chest compression and a higher intensity vibration to encourage the acute care provider to release the chest compression.

In other examples, feedback can be based on trends in quality of resuscitation activities being performed and/or about quality of recently performed resuscitation activities (e.g., feedback regarding a number of preceding chest compressions) to provide the acute care provider with information related to quality of care being provided to the patient over time. For example, the device 120 can be configured to emit haptic feedback according to a first feedback pattern if an average depth for a predetermined number of preceding compressions was within a suitable target range. The device 120 can be configured to emit haptic feedback according to a second haptic pattern if the average compression depth for the predetermined number of preceding compressions did not fall within the target range. As discussed above, various haptic vibration patterns, intensities and/or algorithms for producing the patterns/intensities may be stored with memory of the device 120, and the device 120 may be pre-configured for a particular pattern to correspond to a particular activity.

In some instances, audio feedback may be provided along with haptic feedback to provide additional information to the acute care provider. For example, the device 120 may be configured to emit multiple tones forming a major chord to encourage the acute care provider in performance of the resuscitation activity, such as if the measured values are within a predetermined range of the measured values. Similarly, the device 120 can be configured to emit multiple tones forming a minor or descending chord to signify to the acute care provider to modify performance of the resuscitation activity, if it is determined that the measured values are more than a predetermined amount from the target values.

As shown at box 422, acute care provider fatigue can be identified by monitoring changes in the comparison between the measured values and target parameter values over time. For example, if the comparison between measured values for the resuscitation activity being performed and the target parameter values demonstrates a decrease in quality of chest compressions (e.g., a difference between measured values for the resuscitation activities being performed and the target values increases over time), it can indicate that the acute care provider is becoming fatigued. If it is identified that the acute care provider is becoming fatigued, the device can provide a notification to inform the acute care provider that he or she should switch places with another acute care provider.

As shown at box 424, the device can determine an appropriate time to cease performance of the resuscitation activity, and provide a notification (e.g., via visual, audio, haptic and/or other type of sensory feedback) to the acute care provider to that effect. For example, chest compressions could be stopped when measured physiological information indicates that the patient is sufficiently stable, and that the resuscitation activity is no longer required. In other examples, the device can instruct the user to cease a resuscitation activity if another type of therapy should be provided to the patient. For example, the notification can instruct the acute care provider to "Stop Compressions" and "Stand Back" if a defibrillation shock is to be provided to the patient. In some examples, the notification to cease the resuscitation activity can be provided with a different haptic pattern than the haptic pattern signaling the acute care provider to begin compressions and/or the haptic pattern(s) related to the comparison of the measured values and target values. In other examples, feedback to cease the resuscitation activity can be provided as a different type of feedback from the feedback that guides performance of the resuscitation activity. For example, if feedback guiding performance of chest compressions is haptic feedback, the notification to cease compressions and stand back can be provided by an audible alarm.

Generation of Metric or Score of Resuscitation Activity Quality

Figure 5:
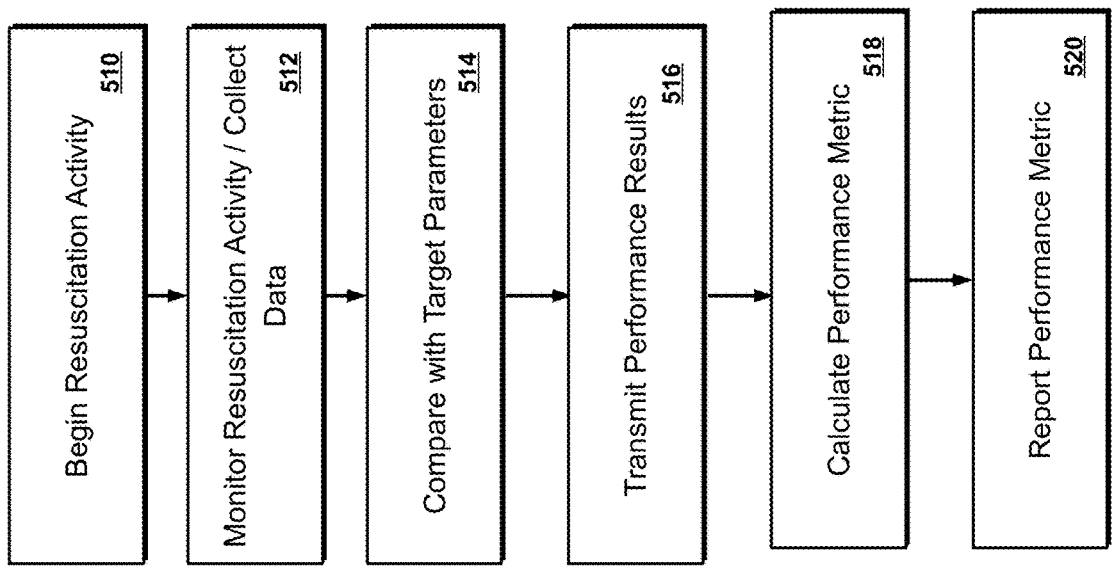
FIG. 5 is a flowchart, of an exemplary process for providing a performance metric to an acute care provider of resuscitation activities.

With reference to FIG. 5, a flowchart showing a process for generating a metric or score for performance of one or more resuscitation activities by one or more acute care providers is illustrated. In particular, signals received by sensors associated with the device(s) 120 (shown in FIGS. 1-3A) can be used for generating an overall metric or score for performance of resuscitation activity by a user over a predetermined time interval or over the entire duration of the emergency event. In some examples, a score or metric can be generated for each acute care provider at a rescue scene based on signals received from each acute care provider's respective device 120. In that case, the process can include steps for receiving motion-based signals from a plurality of devices, and for associating each received signal with a respective acute care provider to distinguish which resuscitation activities are performed by which acute care provider and to tailor the metric or score for actions performed by each acute care provider. The metric or score can be in the form of a numeric or letter score representative of quality of treatment provided to the patient. Since an acute care provider may perform a variety of different types of resuscitation activities over the course of an emergency event, the score or metric can be inclusive of quality of different types of resuscitation activities.

As shown at box 510, one or more acute care providers are instructed to begin performing a resuscitation activity. As shown at box 512, the device(s) 120 monitor performance of the resuscitation activities. For example, the device 120 may identify the type of resuscitation activity being performed by each acute care provider. In some examples, identification of the type of activity being performed can be based on signals received from sensors associated with the device 120. For example, the signals received from the motion sensors can be analyzed to identify whether chest compressions or manual ventilations are being performed. In other examples, the resuscitation activity being performed may be predetermined or received from an external source and, accordingly, analysis of motion sensor signals is not required to identify the resuscitation activity.

In some examples, an acute care provider switches between a number of different resuscitation activities during an emergency event. Accordingly, the data recorded from the motion sensors can include portions in which the acute care provider is performing a first resuscitation activity, portions in which the acute care provider is performing a second resuscitation activity, and portions in which the acute care provider is not performing a resuscitation activity. Monitoring performance of the resuscitation activity can include identifying when an acute care provider changes resuscitation activities based on the signals received from the motion sensors. Monitoring the performance of resuscitation activities can also include annotating or identifying which portions of the received signals correspond to which resuscitation activities.

As shown at box 514, the signals received from the motion sensors on the device(s) can be analyzed to assess correspondence between measured values for the resuscitation activities performed and target parameter values. The signals received from the motion sensors can be processed locally on each user's device, and results of comparisons to target parameter values can be stored locally on transitory computer readable memory of the device. Alternatively, as shown at box 516, the results can be wirelessly transmitted from the device to an external computing device or computer network. For example, information related to performance of resuscitation activities can be processed and stored on portable computing devices located at an emergency scene. In other examples, information about performance of resuscitation activities can be transmitted to a remote computing device, central server, or computer network for further analysis and storage.

Following cessation of the resuscitation activities and/or after treatment of the patient is completed, as shown at box 518, an overall score or metric based on the information collected from the one or more devices can be calculated. In some examples, a time interval can be selected to limit when performance of the resuscitation activity performance is considered. For example, a pre-selected interval can be used (e.g., an interval of 30 seconds). In other examples, the interval can be based on the duration of a normal CPR cycle (e.g., a cycle including 30 compressions followed by two ventilations). In that case, a score or metric for each time interval can be calculated. In some examples, a separate score or metric can be calculated for each resuscitation activity performed based on motion signals received from a single wrist-worn device. In addition, a final total or overall score for all resuscitation activities performed by each acute care provider during the entire duration of treatment can be calculated. Exemplary algorithms for calculating a score or metric representative of overall quality of CPR based on signals received from motion sensors are described in United States Patent Publication No. 2013/0296719, entitled "Rescue Performance Metric," which is incorporated by reference in its entirety.

In some examples, calculation of a score or metric can be adjusted based on environmental factors. For example, it is recognized that performing resuscitation activities while a patient is being transported in an ambulance can be more difficult than performing resuscitation activities prior to transport of the patient. Therefore, if it is determined that the patient is being transported, the metrics for evaluating the acute care provider may be adjusted. For instance, since performing manual chest compressions while traveling in an ambulance may be more difficult than when not located in a traveling vehicle, an acute care provider's score or metric can be adjusted to reflect such conditions. That is, to account for the acute care provider being subject to conditions where it is more challenging to administer CPR or when CPR quality is likely to be compromised, such as during vehicular motion or transport, the manner in which an acute care provider is evaluated may be relaxed and the overall performance evaluation may be higher. Or, for purposes of evaluating acute care provider performance, CPR measurements during transport may be discounted from the overall score. Thus, the scoring rubric for assessing the acute care provider may account for whether chest compressions are being administered during transport.

As shown at box 520, the calculated score or metric can be provided to the one or more acute care providers. For example, the score or metric can be shown on the visual display screen of the device. In other examples, a score or metric can be given to the acute care provider in the form of a report card provided to each acute care provider at a follow-up meeting or briefing after treatment of the patient is completed. In some examples, the report card can include a score or metric for each resuscitation activity performed by the acute care provider. In addition, the report card can include an individual score for each time interval which demonstrates changes in treatment quality over time. In addition, the report card can include a combined or total care metric determined by combining scores for each of the acute care providers that treated the patient. Further, the total care metric can be considered in connection with outcome information related to the physical condition of the patient to provide a correlation between acute care providers, resuscitation activities performed, and effects of the treatment for the patient.

Generation of Time-stamped Record of Patient Treatment

Figure 6:
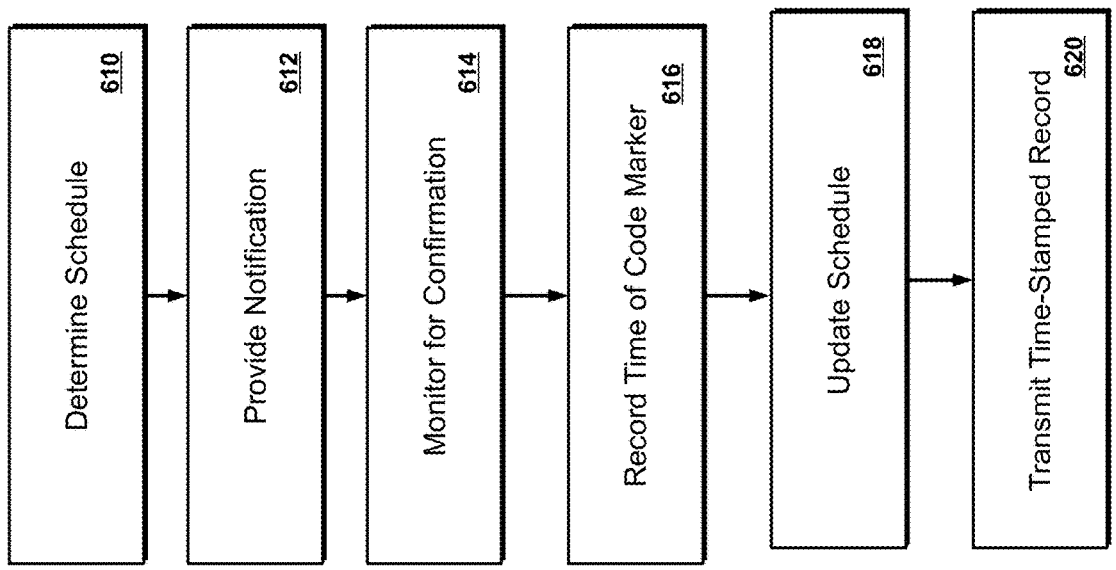
FIG. 6 is a flowchart of an exemplary process for creating a time-stamped record of a resuscitation activity performed during treatment of a patient.

With reference to FIG. 6, a flowchart showing a process for generating a time stamped record of resuscitation activities performed for a patient at an emergency scene by one or more acute care providers is illustrated. As described herein, the process can include receiving motion-based information from devices worn by multiple acute care providers and associating the received signals with respective acute care providers or devices. In that way, the generated time-stamped record may include information about which of the acute care providers performed particular activities. As shown at box 610, a schedule or checklist for when acute care provider(s) wearing wrist-worn device(s) should perform certain resuscitation activities for a patient is determined. The determination of when certain resuscitation activities should be performed can be based on treatment schedules stored on the computer memory of the device. Alternatively, the determination of when certain resuscitation activities should be performed can be based on information received from an external source, such as a central server or computing device remote from the emergency scene. In other examples, a treatment protocol can be determined for a particular patient by a medical device (e.g., a defibrillator or patient monitoring device) or rescue management apparatus located at the emergency scene. Further, the rescue management apparatus can determine which activity or activities of the treatment protocol should be performed by a particular acute care provider. The rescue management apparatus can then transmit information to a respective acute care provider's wrist-worn device detailing which activities the acute care provider wearing the device should perform.

As shown at box 612, at a scheduled time, the device is configured to provide a notification to the user to perform a scheduled resuscitation activity. The notification can include one or more of a visual notification (e.g., text, images, or animations shown on the device display), an audio notification emitted from the device speakers, and/or a tactile or haptic notification, such as causing the device to vibrate according to a predetermined haptic pattern. As discussed herein, in some instances, the haptic pattern or intensity can be varied to indicate to the acute care provider what type of resuscitation activity should be performed. In some examples, the device may also be configured to generate alert notifications based on information collected by the user's device and/or from devices worn by other acute care providers. The alert notifications can inform the user to begin performing a higher priority activity. For example, a device worn by a leader at a rescue scene may emit an alert notification informing the user to check on one of the other acute care providers. Notifications may also instruct the wearer to perform other actions such as checking patient vitals or to stand back if a defibrillator is preparing to provide a shock to the patient.

As shown at box 614, the device 120 can be configured to monitor for confirmation that the scheduled activity has been and/or is being performed. In some examples, the confirmation can be a DTA Marker for annotating a patient record with information about when certain resuscitation activities or other diagnostic or therapeutic were performed. In some examples, the confirmation can include analyzing a signal from one of the device sensors representative of performance of the scheduled activity. For example, if the scheduled activity is performing chest compressions to the patient, the confirmation can comprise receiving a motion-based signal from the motion sensor of the device representative of the cyclical up and down movement indicative of performance of chest compressions. In other examples, the user may be required to perform a confirmation action that is not directly derived from performance of the scheduled resuscitation activity. For example, the acute care provider can speak a phrase, such as "Starting Chest Compressions," "Starting Ventilations," "Administering Drug," "Alert acknowledged" or "Task completed" to document that he or she has heard the notification or alert and performed or is performing the required activity. The microphone of the device can record the acute care provider's speech and process the recorded signal to confirm that the spoken phrase matches an expected confirmation activity. Similarly, the user can acknowledge the alert with other input components of the device, such as pressing a virtual acknowledgement button on the device screen and/or performing a predetermined gesture that can be recognized by the optical sensor or camera of the device. Also, the user can request that an instruction be repeated, or ask for further information regarding a task, for example, drug dosage information for a specified patient weight.

The alert acknowledgment can include entering a DTA Marker for an activity being performed. In some instances, the DTA Marker can refer to an entry of a predetermined checklist of clinical actions or resuscitation activities that can be provided to the patient either by the acute care provider or by a medical device at the emergency scene and which can be recorded on a summary report illustrating the sequence of patient treatment events. DTA Markers may be useful for post-rescue review to evaluate the overall course of a resuscitation after the fact, particularly in determining the timing of therapeutic interventions administered to the patient. DTA Markers may be input into the device via any suitable manner provided by the device, for example, via the microphone, scrolling functionality (e.g., digital crown, scroll bar), touch screen, etc.

Exemplary DTA Markers can include, for example, CPR, Intubate, Airway (clear airway), CPAP (apply continuous positive airway pressure), IV (intravenous medication), IO (intraosseous infusion), Nebulize, Cooling, Sedate, Event, Epi (e.g., administration of epinephrine), Atrop (administration of atropine), Dopa (administration of dopamine), Valium (administration of valium), Phen, Bicarb (administration of sodium bicarbonate), Analges (administration of an analgesic), RSI (rapid sequence intubation), Aspirin, Oxygen, Morphine, B-block (administration of a beta blocker), Lido (administration of lidocaine), Mag Sulf (administration of magnesium sulfate), Thrombo (administration of a thrombolytic), Sedation (administration of a sedative), Heparin (administration of heparin), Procain (administration of procaine), Amio (administration of amiodarone), Amiodar, Gluca (administration of glucagon), Thiamine, Dilantin, Narcan, Atrovent, Adenosine, Fentanyl, Digoxin, Vasopr (administration of vasopressin), Dextrose, Paralytic, Nitro (administration of nitroglycerin), Ca Block, Etomidate, Ativan, Glucose, Albuterol, Amrinon (administration of amrinone), Benadryl, Demerol, Oral Glu (administration of oral glucose), Lasix (administration of furosemide), Calcium, Versed (administration of midazolam), Steroid, Bolus, amongst others.

Each of the DTA Markers may have one or more associated treatment protocols associated therewith, for example, administrating the drug or activity multiple times according to a suitable time sequence. For instance, it may be required for epinephrine to be administered a number of times. Accordingly, when the Epi DTA Marker is input, the device 120 may provide an automatic timer that signals the user each time the epinephrine should be administered. Certain DTA Markers may be more appropriate for certain patient conditions. For example, DTA Markers appropriate for cardiac arrest may include CPR, intubate, Epi, Atrop, Dopa, Phen, Bicarb, Lido, Narcan, B-block, Atrovent, Mag Sulf, Procain, Adenosin, Fentanyl, Digoxin, Vasopr, and/or others. In another example, DTA Markers relevant for respiratory distress and/or traumatic brain injury may include Oxygen, Intubate, Morphine, Valium, Sedation, Atrovent, Paralytic, Albuterol, Lasix, Versed, and/or others.

In order to enter or identify the DTA Marker, the acute care provider can speak into the microphone the name of the resuscitation activity being performed while performing or immediately following performance of the activity. For example, the user can speak the phrase "Give Epi" while providing an epinephrine injection to the patient. Or, the user may be able to enter the DTA Marker through another action input, such as gestural recognition and/or via the touch screen. The built-in motion sensor (e.g., accelerometer) may be able to recognize the gestures of the user and, hence, identify the type of DTA Marker to be input into the system. The touch screen may employ the force touch feature to input DTA Markers, for instance, using a soft touch to scroll and select from amongst a number of DTA Markers, and a more forceful touch to preview and/or actually select a DTA Marker.

As shown at box 616, the device records the time that the DTA Marker is received so that the DTA Marker can be coordinated with a patient physiological signal (e.g., ECG) and shown on the treatment summary report. It can be appreciated that DTA Markers may be entered by any suitable method. For example, the device may include a scrolling functionality (e.g., digital crown, rotary dial, touch screen, etc.) that allows the user to scroll through a list of applicable DTA Markers and make an appropriate selection therefrom. The selection may be made by any suitable manner, for example, via a button, speaking into a microphone, through a touch screen, etc.

As shown at box 618, determining or recognizing that the acute care provider has provided a DTA Marker can cause the device to update or modify the treatment protocol or checklist of scheduled resuscitation activities to be performed. For example, when the device identifies a DTA Marker signifying that an epinephrine injection has been provided to the patient, it may automatically schedule additional epinephrine injections based on when the first DTA Marker for epinephrine is identified. Accordingly, when the Epi DTA Marker is identified, the device can automatically initiate a timer or stopwatch to count down until the next injection or administration should be given to the patient. When the countdown elapses, the device can be configured to provide a notification that another epinephrine injection should be provided to the patient. In this way, providing a DTA Marker both provides a time-stamped record of when a resuscitation activity is performed and updates the treatment protocol or schedule to include additional resuscitation activities. Additionally, identification of a DTA Marker can cause the device to automatically update the treatment protocol or checklist of scheduled resuscitation activities to include related activities to be performed by the acute care provider. For example, when a DTA Marker for administering epinephrine is received, the device can automatically schedule other activities such as checking patient vital signs (e.g., heart rate, oxygen perfusion, etc.) to confirm that the injection is effective.

As shown at box 620, the device can be configured to transmit a time-stamped record of DTA Markers and/or resuscitation activities identified during treatment of a patient. The time-stamped record can include, for example, data representative of when notifications were provided, when confirmation that the resuscitation activity was performed was received, and when and what DTA Markers were identified. The time stamped record can be used to generate a summary or report of treatments provided to the patient. The summary report can include a timeline of DTA Markers for particular resuscitation activities shown in a coordinated manner along with sensed physiological signals for the patient, such as patient ECG. The time-stamped record and/or summary report can be sent, for example, to a central patient monitoring facility or data storage facility, where it can be added to a patient's electronic health record. In other examples, the time-stamped record and/or summary report can be forwarded to other medical personnel, such as to a physician responsible for treating the patient once he or she arrives at a hospital or other medical facility. The time-stamped record can be sent to the external source once treatment is completed or, for example, when the patient is transferred from the acute care providers to a hospital or medical facility. In other examples, the time-stamped record can be sent from the device to the external source at predetermined intervals, as treatment is being provided to the patient. For example, a time-stamped record can be uploaded to the external device once every 5 or 10 minutes. In other examples, the device can be configured to upload information when the device is not performing other processor-intensive functions such as, for example, times when the acute care provider is resting or switching roles and when the device is not providing feedback about resuscitation activities being performed.

Generation and Receipt of Information from Victim Devices

Figure 7:
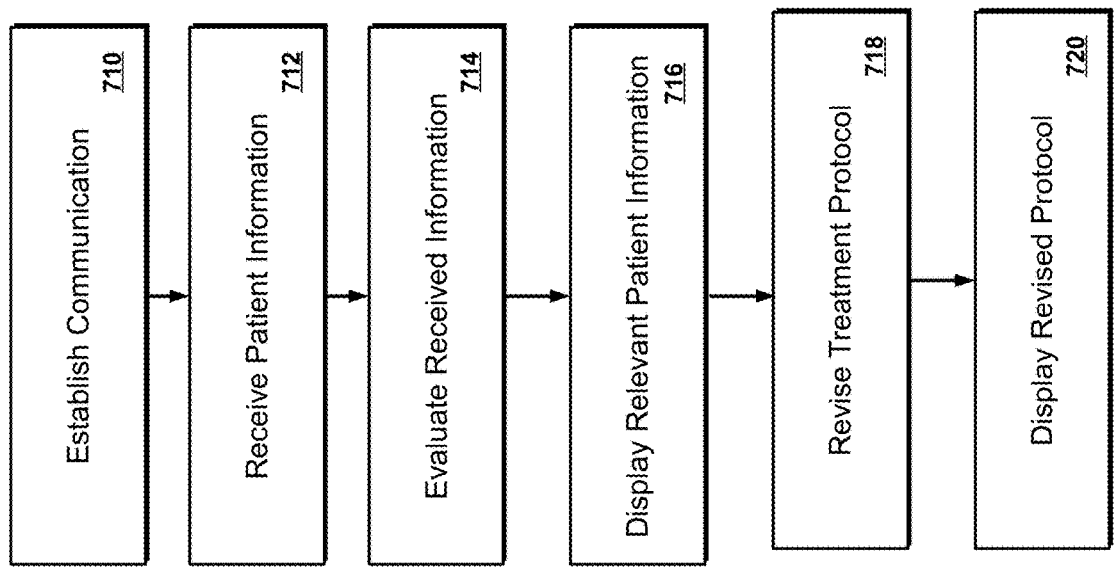
FIG. 7 is a flowchart of an exemplary process for revising a treatment protocol for a patient in response to received information.

With reference to FIG. 7, an exemplary process performed by a wearable electronic device worn by an acute care provider for receiving information about a victim to assist in treatment of the victim is illustrated. As shown at box 710, in some examples, the device can be configured to establish a wireless connection with an external computing unit having computer readable memory including information about a patient or victim to be treated. The external computing unit can be located at the emergency scene and associated with the patient or victim. In that case, the acute care provider's wearable device may be configured, upon arrival at an emergency scene, to attempt to identify and communicate with the victim's external computing unit. For example, the external computing device can be a wearable medical device, such as a medical monitoring device or a wearable therapeutic medical device (e.g., a wearable defibrillator) or a multifunction electronic device, such as a patient or victim's smartphone, wrist-worn electronic device (e.g., a smartwatch), or PDA. The patient or victim's device can include software (e.g., an App) including instructions for accumulating patient information and, upon receiving a request from a device worn by an acute care provider, transmit the accumulated patient information to the acute care provider's wrist-worn device. In other examples, the external computing unit can be an external computer database located at a remote location from the emergency scene. For example, the external computing unit can be a hospital database including electronic medical records for the patient.

As shown at box 712, the device can be configured to wirelessly communicate with the external computing device to receive patient information that can be used to assist in treatment of the patient. The patient information can include, for example, personal identification information of the patient, an estimated or exact location of the patient (e.g., as determined by location identifying circuitry on the patient's electronic device), recent motion related activities of the patient, patient downtime (e.g., an amount of time that the patient has been immobile, such as due to being unconscious, as sensed by an accelerometer), an estimated amount of time that the patient has been incapacitated, medical history information of the patient, and physiological event information of the patient (e.g., whether sensors or monitoring devices associated with the patient identified a physiological event). A patient physiological event can be a temporary physiological problem or abnormality, which can be representative of an underlying patient condition (e.g., a heart attack or stroke). A physiological event can also include injuries and other non-reoccurring problems that are not representative of underlying physiological condition of the patient. A non-exhaustive list of cardiac patient events that can be detected by an external medical device (e.g., via ECG electrodes and an appropriate analysis algorithm) include, for example: bradycardia, ventricular tachycardia (VT) or ventricular fibrillation (VF), atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm.

As shown at box 714, the received patient information can be processed and analyzed by the device to determine whether the information is relevant for the treatment activities being performed by the acute care provider. For example, if the acute care provider is responsible for providing ventilation to the patient or victim, medical information related to the patient's breathing ability, lung capacity, lung function, and other physiological characteristics can be relevant for optimizing treatment parameters. If information is determined to be relevant for the resuscitation activity being performed, the information can be presented to the acute care provider in the form of a notification by one of the output components of the device, as shown at box 716. For example, the notification can be displayed on the display screen or provided as an audible notification emitted from device speakers. The device can also provide haptic feedback to the acute care provider related to the received information about the victim. As discussed herein, different haptic patterns and/or types of feedback can be emitted from the device based, for example, on the type and/or urgency of the identified victim condition. For example, the acute care provider's device may emit a high intensity vibration if the received information is relevant for the resuscitation activities being performed. The device may emit a low intensity vibration if the received information about the victim condition is immaterial for the resuscitation activities being performed. The determination of whether the received victim information is relevant can be made by external computing devices and/or by other acute care providers at the acute care provider scene (e.g., by a team leader). In some examples, as shown at box 718, the received patient information can be used to determine, revise, update, or adjust the treatment protocol for the patient. As shown at box 720, feedback for performing resuscitation activities in accordance with the revised treatment protocol can be provided to the acute care provider by the output components of the acute care provider's device. In addition, processes for providing feedback to an acute care provider for performing resuscitation activities in accordance with a treatment protocol are described hereinabove, in connection with FIG. 4.

Figure 8:
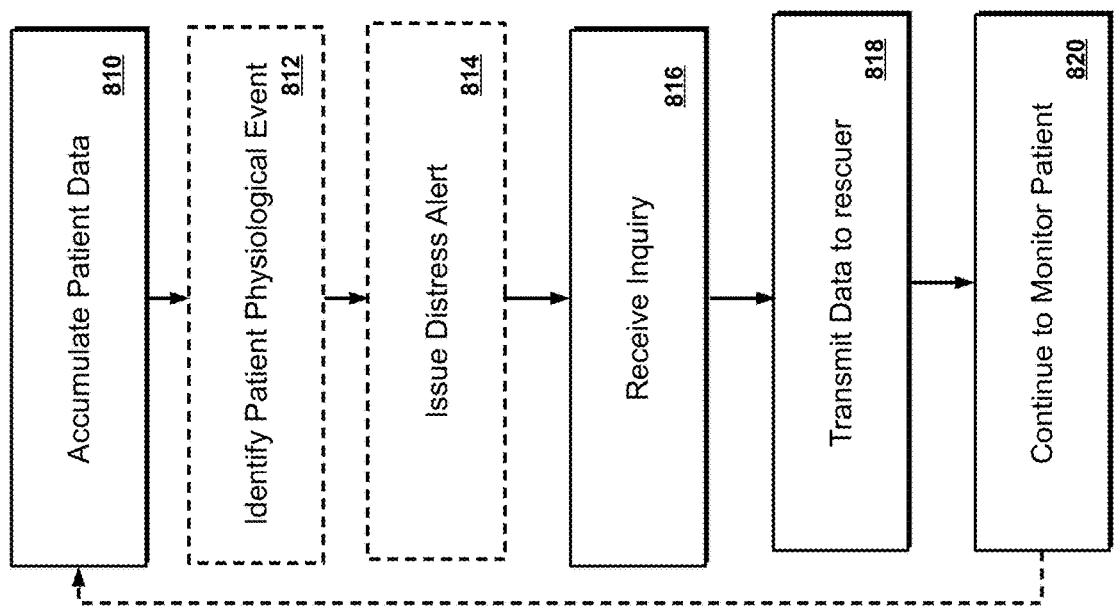
FIG. 8 is a flowchart of an exemplary process for providing patient information from a wrist-worn device worn by the patient to another computerized device.

In some examples, the wrist-worn device described herein can be configured to be worn by an individual experiencing a medical emergency (e.g., a victim). With reference to FIG. 8, a flow chart is provided, which illustrates processes executed by a device worn by the victim at a rescue scene for collecting information about the victim to assist acute care provider(s) in providing treatment for the victim. For example, information about victim downtime (e.g., how long a patient has been immobile and/or a length of time since the patient fell to the ground) can be determined based on motion-based signals collected by the device. Information from other sensors (e.g., heart rate sensors, blood pressure sensors, etc.) associated with the device and/or victim can also be collected to provide additional about victim status and/or condition.

As shown at box 810, the victim's wrist-worn device can be configured to accumulate motion-based signals from one or more motion sensors associated with the victim's wrist-worn device and/or signals from other physiological sensors associated with the device and/or victim.

As shown at box 812, optionally, signals from the sensors can be used by the victim's wrist-worn device to identify an occurrence of events. For example, motion-based signals received from the motion sensors can indicate victim downtime. Information received from physiological sensors can also be received and processed for identifying physiological distress. In some examples, the device can record a time when the event occurs so that a record of events experienced by the patient can be provided to the acute care provider.

In some examples, if a physiological event is identified, the device can be configured to automatically issue a distress alert, as shown at box 814. For example, the distress alert can be sent from the device to an emergency response system (e.g., a 911 operator). Upon detection of a physiological event, the device can also emit various notifications or messages to alert bystanders that the user is in physiological distress and requires assistance. For example, the device could play a distress signal or message, such as "Medical emergency. Please seek help."

In some implementations, once acute care providers arrive at an emergency scene, information recorded on the victim's wrist-worn device can be transmitted to other electronic devices, such as wrist-worn devices worn by the acute care providers. Transmission of data can be in response to a request manually or automatically issued by the acute care provider's device. For example, as shown at box 816, the device can receive an inquiry from an external computing device (e.g., rescue management apparatus, tablet, laptop, computer, mobile device, phone, wrist-worn device). Upon receiving the inquiry, information including the victim downtime can be transmitted from an output component (e.g., a wireless transmitter) of the victim's device to the external computing device, as shown at box 818. The external computing device can use the received downtime information to establish or update a treatment protocol for the victim. In some examples, the victim's wrist-worn device can be configured to transmit patient information to the external computing device along with physiological event data. The victim information can be stored on computer-readable memory on the victim's device. The victim information can include, for example, personal identification information, victim age, height, weight, medical history, allergies to medications, and a list of medications that the patient is currently taking.

As shown at box 820, after the data transmission is completed, the victim's wrist-worn device can be configured to continue to monitor physiological condition of the victim, or monitor signs indicative of a physiological condition. If another physiological event is identified by physiological sensors associated with the device, the device can be configured to emit a notification or alert in the manner discussed above. For example, the notification or alert can be an audible notification so that it can be heard by acute care providers treating the victim.

Emergency Response Management Systems

Having described the structure and electrical components of a wrist-worn device 120, rescue management systems that coordinate or direct activities of multiple acute care providers wearing respective wrist-worn devices 120 will now be discussed in connection with FIG. 9. A rescue management system can be used at an emergency scene to treat a patient. For example, the system can be configured to receive information from different wrist-worn devices 120 to determine a status of the acute care providers at the emergency scene and to provide information to the users of the respective devices related to the activities being performed by each acute care provider. The system can be configured to coordinate care for the patient both at the emergency scene and during transport of the patient from the emergency scene to a hospital or medical facility. In other examples, as described in connection with FIG. 11, a system including one or more wrist-worn devices 120 can be used in a hospital environment to, for example, receive information, notifications, and alerts from monitoring devices associated with one or more patients being treated at the facility. In still other examples, as described in connection with FIG. 12, a system including one or more of the wrist-worn devices 120 can be used to monitor or evaluate status of medical devices, such as wall mounted automated external defibrillation devices (AEDs).

The systems described herein can include numerous computerized electronic devices configured to communicate with one another for providing therapy to a patient. In some examples, the computerize devices, such as smartphones, tabletPC, and wrist-worn electronic devices can be dedicated electronic devices including non-transitory memory with instructions for performing functions of the system. In other examples, the devices can be multipurpose computerized devices running downloadable software (e.g., an app) for interacting and/or communicating with other devices of the system. The app can include instructions that when executed by one or more processors of the computerized devices cause the devices to perform functions of the system.

Rescue Management System for Use at Emergency Scene

Figure 9:
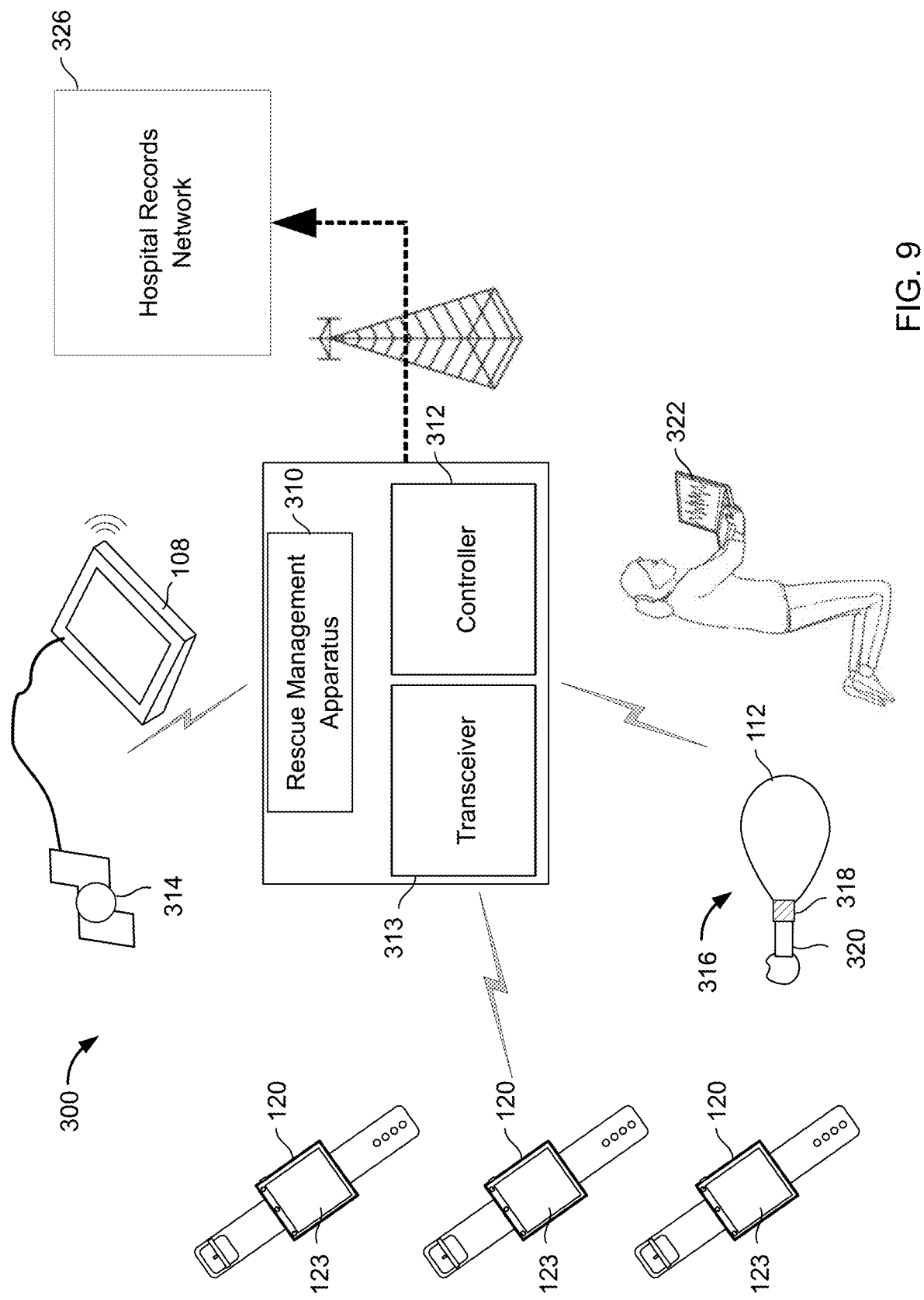
FIG. 9 is a schematic drawing of an exemplary rescue management system including wrist-worn devices configured to be worn by acute care providers at an emergency scene.

With reference to FIG. 9, an exemplary rescue management system 300 is illustrated comprising one or more wrist-worn devices 120, each of which is configured to be worn by an acute care provider at an emergency scene. As described above in connection with FIG. 3A, each wrist-worn device 120 can include a motion sensor, such as an accelerometer or gyroscope, to provide information for assisting an acute care provider wearing the device 120 in performing resuscitation activities. The system 300 also includes a rescue management apparatus 310 in wireless communication with each of the wrist-worn devices 120. The rescue management apparatus 310 can be a computer device, such as a desktop computer, laptop computer, tabletPC, wrist-worn device, smartphone, or PDA having a processor or controller 312 in communication with a wireless transceiver 313 configured for bidirectional communication with the wrist-worn devices 120. In other examples, the rescue management apparatus 310 can be integrated with and/or physically connected to other medical devices at an emergency scene including, for example, a defibrillator 108 or mechanical ventilator. In other examples, the rescue management apparatus 310 can be remote from the emergency scene. In that case, the rescue management apparatus 310 can include circuitry for long-range data communication to interact with the wrist-worn devices 120 and/or other computerized devices and medical devices located at the emergency scene. In particular, the wrist-worn devices 120 can be configured to directly transmit signals to and receive signals from the remote rescue management apparatus 310. In other examples, data transmission from the wrist-worn devices 120 to remote computerized devices can be performed through one or more intermediate devices, such as smartphones, tabletPCs, computers, wireless routers, and other communications gateways.

In some examples, the controller 312 of the rescue management apparatus 310 is configured to execute software for managing aspects of an emergency scene. For example, the controller 312 can be configured to associate each of the wrist-worn devices 320 with a respective acute care provider role. For example, the controller 312 may be configured to provide an output that assigns each wrist-worn device 120 at the emergency scene with a respective resuscitation role, such that each wrist-worn device 120 outputs resuscitation information related to a treatment protocol corresponding to the assigned resuscitation role. In some examples, associating a wrist-worn device 120 with a respective role comprises identifying a resuscitation activity being performed or selected by a respective acute care provider (e.g., an acute care provider performs a gesture indicating the role he or she intends to perform). The resuscitation activity being performed or to be performed by an acute care provider may be identified by a number of suitable methods. For example, the system may assess the location of each acute care provider around the patient, and infer the acute care provider role based on the location of the acute care provider. Or, the system may infer the acute care provider role via certain movements of the acute care provider that are indicative of specific resuscitation activities. In other examples, associating a wrist-worn device 120 with a respective role comprises assigning a role to a respective acute care provider. An acute care provider role can refer to the resuscitation activity that a particular acute care provider is responsible for providing to the patient. Accordingly, in some examples, one acute care provider can select or be assigned the role of providing chest compressions to the patient (e.g., inferred by up and down motion and/or location of the device over the patient's sternum) and, in some cases, the device 120 may provide information to the acute care provider specific to that role (e.g., show display indicating perfusion performance due to chest compressions). A second acute care provider can select or be assigned the role of providing ventilations to the patient (e.g., inferred by the orientation of the device and/or location of the device proximate to the patient's mouth/airway), and the acute care provider may be provided with information relevant to that role only (e.g., indication of ventilation performance). A third acute care provider can be responsible for setting up a therapeutic medical device, such as a defibrillator or mechanical ventilator, and/or administering medicinal or therapeutic agents to the patient at predetermined intervals, and this acute care provider may be provided with relevant information (e.g., checklist of interventions, protocol, treatments; and equipment to be set up). In other examples, a third acute care provider can be responsible for monitoring patient vital signs as the first two acute care providers provide CPR. In other examples, a third acute care provider can be instructed to rest for a predetermined period of time. After the predetermined period of time elapses, the acute care provider management apparatus 310 can instruct the acute care providers to switch roles. In some examples, another role that could be performed by one of the acute care providers is a team leader or emergency site coordinator role. The leader or coordinator can be responsible, for example, for monitoring the patient condition, communicating with medical facilities or others about transportation of the patient, and other activities needed for treatment of the patient in an emergency situation. The team leader may also be responsible for monitoring or reviewing performance of resuscitation activities by the other acute care providers. For example, if the team leader identifies that a team member is becoming fatigued, the team leader may instruct the acute care providers to switch roles or take other action to assist the fatigued acute care provider.

The controller 312 can also be configured to transmit information related to performance of the assigned or selected role to the wrist-worn device 120 for each acute care provider. For example, a signal transmitted from the rescue management apparatus controller 312 can cause each respective wrist-worn device to provide a notification to the user representative of the role to be performed. For example, the notification could include text or images on the device display 123 (shown in FIGS. 1-3A) instructing the user to begin an assigned role, such as "Begin Chest Compressions" or "Set up the Defibrillator."

Defibrillator and Treatment Electrodes

In some examples, the system 300 can also include one or more therapeutic medical devices for treating the patient, such as the defibrillator 108. As described above in connection with FIG. 1A, the defibrillator 108 comprises sensing electrodes attached to the patient for monitoring cardiac function of the patient. For example, the sensing electrodes can monitor patient ECG, heart rate, and other cardiac parameters. The defibrillator 108 can comprise wireless communications circuitry for transmitting the sensed information the rescue management apparatus 310 and/or to individual wrist-worn devices 120. In some examples, the defibrillator 108 can monitor patient ECG to identify a shockable cardiac rhythm that can be treated by the defibrillator 108. When a shockable rhythm is identified, the defibrillator 108 can transmit signals to the rescue management apparatus 310 and/or wrist-worn devices 120 instructing the acute care providers to stop performing resuscitation activities and to step away from the patient. In other examples, information from the defibrillator 108 can be transmitted to the wrist-worn devices 120 and displayed on the visual 123 of the device 120. In this case, the wrist-worn device 120 can be a remote display or remote alarm for the defibrillator 108. Beneficially, the user can receive information about operation of the defibrillator 108 without being required to divert his or her attention from the resuscitation activity being performed.

CPR Assistance Device

In some examples, the system 300 can comprise a CPR assistance device for measuring and/or providing guidance regarding rate and depth of chest compressions configured to be placed on and/or held against a patient's chest. The assistance device, which can be for example a CPR or accelerometer puck 314, can be configured to be placed adjacent to the sternum of the patient and to identify downward and upward movement of the patient's chest representative of chest compressions. The acute care provider is instructed to grasp and press the puck 314 against the patient while performing chest compressions. Vertical movement of the puck 314 can be monitored to assess chest compression depth. Acceleration of the puck 314 representative of initiation of chest compression can be monitored to assess chest compression rate. In some examples, the puck 314 is stand-alone device including electronic circuitry enclosed within a substantially rigid housing. The device can be wired or wirelessly connected to the defibrillator 108 for receiving signals from motion sensors of the puck 314. In other examples, as shown by electrode package 110 in FIG. 1A, the puck 314 can be integrated with sensing and/or treatment electrodes that are also configured to rest against the patient's chest.

In some examples, the rescue management apparatus 310 and/or the wrist-worn devices 120 individually can be configured to synchronize with or become associated with the accelerometer puck 314 or other device by a process referred to as "tapping." In some cases, tapping two accelerometer-based devices together causes identifiable motion that can be independently identified by the accelerometer on each device. Or, tapping can also be accomplished using a device that contains Near Field Communication (NFC) hardware; NFC hardware employs a short communication distance (e.g., approximately 4-10 cm). Using NFC communication data or another near field communications protocol, a secure communications link can be established between devices, providing for a longer range network, e.g. via Bluetooth®, Wi-Fi, etc.

A secure wireless communication channel can be established between devices responsive to a proximity-based interaction between the devices. The secure wireless communication channel enables devices involved in the care of a patient to exchange information about the health status of the patient, information about treatment delivered to the patient, patient physiological information, and/or more. The devices or acute care providers using the devices can make use of the secure, exchanged information to efficiently and accurately provide treatment to the patient. For instance, spatial localization (and/or temporal localization) may be determined between devices through a near field wireless communications channel based on appropriate criteria for sensed features of the immediate environment. Based on the spatial localization, and sensed feature(s) that determine the spatial localization, mutual authentication and a secure (e.g., encrypted) communications channel may be established between the devices. Once the secure channel is established, the devices may move away from one another, transitioning to data exchange via a far-field wireless communications channel, yet still maintaining the mutual authentication and secure communications channel, based on the original spatial localization and sensed feature(s). Upon detection of a request for disconnection via another sensed feature (which may be according to the same or different criteria for determining spatial localization), the devices may exit out of the secure communications channel. Hence, the network may be secure and dynamically reconfigurable.

Accordingly, a user of a wrist-worn device 120 can "tap" the wrist-worn device 120 against another accelerometer based device such as the CPR puck 314 to associate the device 120 with the puck 314. The controller 312 of the rescue management apparatus 310 can be configured to recognize the tap (e.g., based on simultaneous motion recorded by accelerometers on each device). Once the association is established, the rescue management apparatus 310 can, for example, associate the acute care provider wearing the identified wrist-worn device with the role of performing chest compressions. Additionally, the rescue management apparatus 310 can cause the identified wrist-worn device 120 to display information related to use of the associated CPR puck 314. For example, the associated wrist-worn device 120 can provide feedback based on compression rate and depth measurements, as measured by the puck 314. Similarly, rate and depth information from the device 120 and puck 314 can be compared to assess accuracy of measurements received from accelerometers on the respective devices.

In some examples, tapping can also be employed to associate the wrist-worn device 120 with other devices at an emergency scene. For example, in cases in which the rescue management apparatus 310 is a smart phone or tabletPC, a user could tap his or her wrist-worn device 120 to the smartphone or tabletPC to form an association with the rescue management apparatus 310. Such an association could be used, for example, to determine which acute care providers are present at an emergency scene. An association could also be established between wrist-worn devices 120 worn by respective acute care providers who want to work together. Once the association is established, the rescue management apparatus 310 can be configured to assign the same role to each of the associated acute care providers. In still other examples, an association between a wrist-worn device 120 and a ventilation device such as a ventilation bag 112 could be established to, for example, identify which acute care provider is using the ventilation bag 112 and to compare motion recorded by the wrist-worn device 120 and with an accelerometer associated with the bag 112.

Patient Ventilation Monitoring

With continued reference to FIG. 9, the system 300 can also include one or more mechanical and/or electronic devices 316 for providing ventilation to the patient and/or for monitoring ventilation status of the patient. A ventilation device 316 can be a manually operated ventilation device, an automatic ventilator, or a mechanical compression device, such as a cuirass. The ventilation device 316 can include one or more sensors for measuring ventilation parameters comprising, for example, ventilation rate, ventilation volume, inhaled oxygen concentration, and exhaled $CO_2$ concentration ($ETCO_2$) of the patient. The ventilation device 316 and/or sensors can be in wireless communication with the wrist-worn devices 120 and/or rescue management apparatus 310 for informing acute care providers about ventilation status.

In some examples, the ventilation device can be a ventilation bag 112. The ventilation bag 112 can include a flow sensor 318 positioned, for example, on a breathing tube 320 extending from the bag 112 to the patient. The flow sensor 318 can be a pneumatic flow sensor comprising a tube having an airway restriction and pressure sensors for measuring changes in airway pressure caused by the airway restriction. The flow sensor 318 can comprise communications circuitry for wired or wireless communication with other electronic devices such as an associated wrist-worn devices 120 and the rescue management apparatus 310. Measurements obtained from the flow sensor 318 can be used to guide administration of mechanical ventilation to the patient by, for example, helping acute care provider to control ventilation volume and/or rate. In particular, if either ventilation volume or rate exceeds predetermined threshold values the system 300 can cause an alert to be provided to the acute care provider. For example, the alert can be wirelessly transmitted from the rescue management apparatus 310 and/or flow sensor 318 to the wrist-worn device 120 worn by the acute care provider performing the ventilation activity. The alert can be provided on the display 123 of the device 120 and/or by haptic and/or audio feedback components of the device 120. The alert can, for example, instruct the acute care provider to modify ventilation volume and/or compression force to adjust output of the ventilation bag 112 for the purpose of modifying a flow rate.

Controlling ventilation parameters can be especially important when traumatic brain injury (TBI) is suspected or diagnosed. For example TBI can be diagnosed based on patient physiological data and/or by a clinical analysis process. In particular, trends or changes in systolic blood pressure, end tidal carbon dioxide ($ETCO_2$), and blood oxygen saturation ($SPO_2$) should be closely monitored to identify hyper- or hypo-oxygenation in TBI or suspected TBI patients. Hypo-oxygenation can be correlated to increased cranial blood flow; hyper-oxygenation can reduce cranial blood flow. Accordingly, if a patient has cerebral herniation or impending cerebral herniation, the $ETCO_2$ and/or ventilation rate targets can be changed in order to hyperventilate the patient so as to reduce intracranial pressure. The system 300 and/or acute care provider management apparatus 310 can be configured to adjust treatment protocols and, in particular, to adjust ventilation parameters to address suspected instances of TBI. Additional examples of processes for modifying resuscitation activities to address TBI are described in United States Patent Publication No. 2014/0201627, entitled "EMS Decision Support Interface, Event History, and Related Tools," and United States Patent Publication No. 2014/0365175, entitled "Rescue Performance Metrics for CPR and Traumatic Brain Injury," each of which is incorporated herein in its entirety.

Tablet/Smartphone

With continued reference to FIG. 9, in some examples, the system 300 can include a portable computing device 322, such as a smartphone, tablet, or laptop computer for managing and/or for accumulating data collected from other electronic devices at an emergency scene. As described above, the smartphone, tablet, and/or laptop computer can be used as the recuse management apparatus 310 that associates and/or assigns roles for acute care providers at the emergency scene. In other examples, the portable computing device 322 can be an intermediate device that is paired or used in conjunction with a particular wrist-worn device 120 for transmitting or receiving data from external sources. For example, an acute care provider may carry a smartphone and wear the wrist-worn device 120. Data obtained from the wrist-worn device 120 can be transmitted directly to the smartphone by a short-range wireless data transceiver for additional processing and/or to be transmitted to an external computer or network by long-range data transmission circuitry on the portable computer or smartphone 322. In other examples, the display 123 of the wrist-worn device 120 can be configured to display information or notifications received from the smartphone (e.g., portable computing device 322). Accordingly, the wrist-worn device 120 can serve as a remote alarm or supplemental screen for the smartphone 322. For example, the display 123 can include icons indicating that a message is received by the smartphone 322 and that the acute care provider should review information being displayed by the smartphone 322. In other examples, the portable computing device 322 can be used to provide more detailed information about the patient and/or emergency scene than can be shown by the wrist-worn device 120. For example, the portable computing device 322 can be configured to display physiological information about the patient received from the defibrillator 108, ventilation device 316, and/or wrist-worn devices 120. In some examples, the portable computing device 322 can display information related to ongoing treatment of the patient. For example, a list of roles or resuscitation activities being performed by each of the acute care providers at the emergency scene can be displayed. Similarly, a treatment protocol for the patient and/or a schedule of how and when acute care providers will switch roles could be displayed. The portable computing device 322 could be used, for example, by a team leader or emergency scene coordinator to assist in coordinating activities of the multiple acute care providers. In particular, the team leader or site coordinator could review the more detailed information displayed on the portable computing device 322 to assist in making decisions about the overall condition of the patient and about whether treatment protocols should be updated.

External Computer Networks

In some examples, the system 300 can comprise one or more external computer networks and databases remote from the emergency scene. One exemplary external computer network that can be accessed by the wrist-worn device 120 and/or rescue management apparatus 310 is a hospital records network 324 including electronic medical records for individual patients. Information about a physiological condition of a patient and/or for medications being taken by the patient can be received from the hospital network 324 and displayed to acute care providers on portable computing devices 322, wrist-worn devices 120, and other electronic devices at the emergency scene. In other examples, medical information about a patient recorded during treatment at the emergency scene can be uploaded to the hospital network 324 as the patient is being transported to the hospital. The uploaded information can be used by doctors at the hospital during treatment once the patient arrives. Uploaded information, such as medications administered and treatments provided, can also be used for electronic billing purposes and for inventory purposes for the emergency responders.

Rescue Management Processes

Having described the wrist-worn device 120 and system 300, processes for coordinating activities of multiple acute care providers will now be discussed in detail. The processes and routines discussed herein are exemplary processes for directing activities of acute care providers and/or for coordinating treatment for a patient using elements of the system 300. It is noted, however, that the elements of system 300 are merely exemplary and that the processes discussed herein can be carried out by many different types of electronic and/or computerized devices.

In some examples, the system 300 can be configured to provide instructions and/or feedback to multiple acute care providers to coordinate treatment of one or more patients by a team of acute care providers. In some examples, each acute care provider wears one of the wrist-worn devices for monitoring and providing feedback about the acute care provider's actions. The rescue management apparatus can be configured to assign a respective role to each acute care provider to coordinate actions of multiple acute care providers.

Figure 10A:
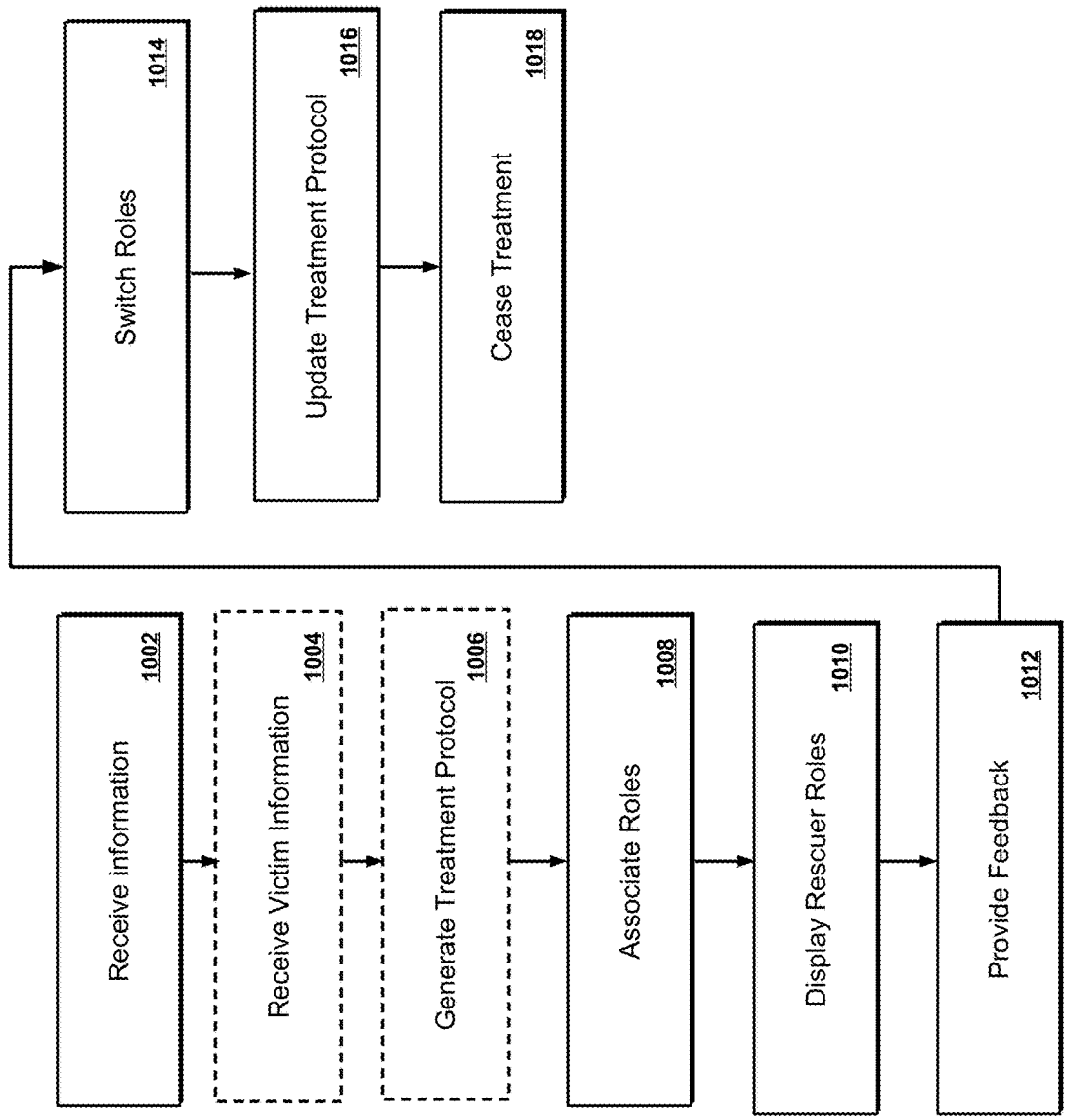
FIG. 10A is a flowchart of an exemplary process for coordinating resuscitation activities performed by multiple acute care providers during treatment of a patient.
Figure 10B:
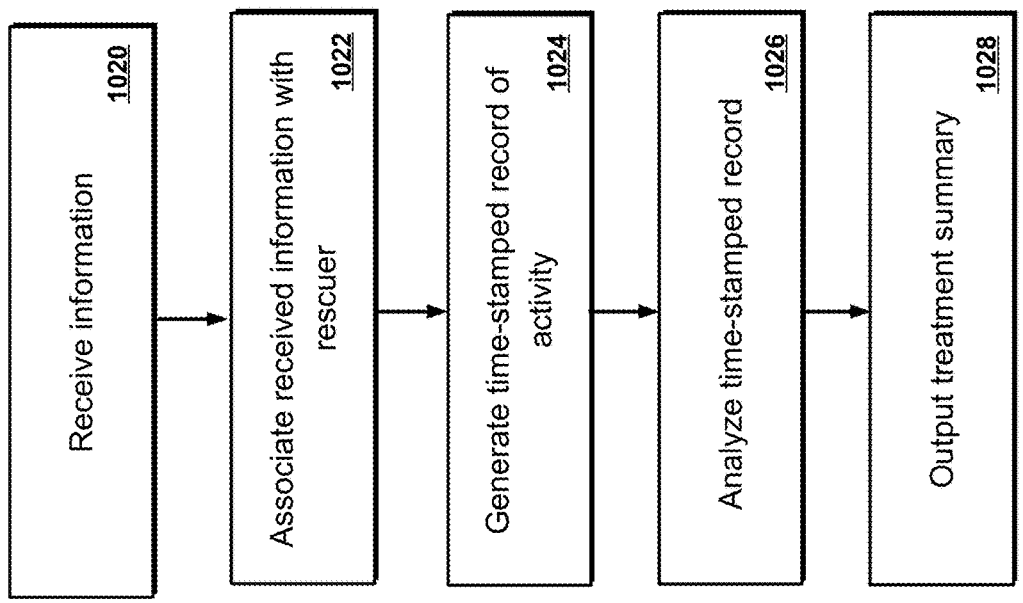
FIG. 10B is a flowchart of an exemplary process for providing a treatment summary for resuscitation activities performed by multiple acute care providers at a rescue scene.

FIGS. 10A and 10B are flowcharts illustrating exemplary processes for coordinating acute care provider resuscitation activities performed by acute care providers at an emergency site. With reference to FIG. 10A, upon arrival at an emergency site, a rescue management apparatus is configured to receive information from wrist-worn devices worn by acute care providers, as shown at box 1002. For example, the information can be motion information obtained from motion sensors associated with the wrist-worn devices. In some examples, the acute care provider management apparatus can be configured to process the received information to identify a number of acute care providers present at the emergency scene (e.g., a number of acute care providers within a predetermined distance from the rescue management apparatus). In some examples, each acute care provider can associate his or her wrist-worn device with the rescue management apparatus by "tapping" in the manner described above. Optionally, as shown at box 1004, the rescue management apparatus can also receive information about the victim from the victim's wrist-worn device. For example, victim information can include the victim's age, height, weight, medical history, and present physical condition. As shown at box 1006, the received information about the number of acute care providers and/or the victim can be used to generate a treatment protocol for the victim. The treatment protocol can include, for example, a list of resuscitation activities to be performed on a patient and a determination of when such treatment activities should be performed. For example, generating the treatment protocol can include dividing tasks to be performed between available acute care providers. The treatment protocol can comprise scheduling when acute care providers should switch roles or, in some cases, when one or more of the acute care providers can rest.

As shown at box 1008, once the treatment protocol is determined, the rescue management apparatus can be configured to associate each of the identified wrist-worn devices with a respective role to be performed. In some examples, the rescue management apparatus automatically assigns particular tasks or roles to particular acute care providers either randomly or according to a predetermined criteria. For example, the assignment of a role to an acute care provider can be based on characteristics of the acute care provider such as physical strength, experience, or skill with particular types of resuscitation activity, as well as on an acute care provider's size, height, or weight. In other examples, the rescue management apparatus can consider elements of the emergency scene when associating a particular role to an acute care provider. For example, as noted above, the assignment of roles can be based on the location of a particular acute care provider (e.g., an acute care provider that is still in the ambulance can be assigned to take out and set up the defibrillator, an acute care provider sitting near the patient's torso can be instructed to begin chest compressions). Similarly, if space or access to the patient is a concern, such as is the case in a vehicle accident, smaller acute care providers can be assigned to provide treatment to the patient while larger acute care providers are assigned other tasks.

In other examples, the acute care provider can select a role and/or a resuscitation activity to perform based, for example, on experience and/or personal preference. For example, the acute care provider can select a role by performing a gesture recognizable by the wrist-worn device representative of the selected role. If the acute care provider will perform chest compressions, he or she can place his or her hands next to one another and move them in a downward direction to mimic a compression action. For performance of a ventilation activity, the acute care provider can place his or her palms in an upward position and close the hands towards the thumbs to mimic compressing a ventilation bag. The wrist-worn device can identify the gesture with a motion sensor or optical sensor of the device and, following identification of the gesture, automatically associate the acute care provider with the identified role. Similarly, the acute care provider's wrist-worn device can be configured to automatically identify if an acute care provider is already performing one of the activities of the treatment protocol. If this is the case, the device can automatically associate the acute care provider with the role or resuscitation activity that he or she is already performing.

As shown at box 1010, the system can provide a notification, such as a message on the visual display, to each acute care provider to inform the acute care provider which role he/she has been assigned. For example, the rescue management apparatus may provide an output to each wrist-worn device including information related to the portion of the treatment protocol that the respective acute care provider is responsible for performing. In a similar manner, as shown at box 1012, once the rescue management apparatus associates each wrist-worn device and acute care provider with a particular role to be performed, the rescue management apparatus can be configured to cause the wrist-worn devices to provide each respective acute care provider with feedback or guidance for performing his or her assigned role. The feedback from the wrist-worn devices can be based on a treatment protocol corresponding to the assigned resuscitation role.

For example, a wrist-worn device for one of the acute care providers can be configured to provide feedback for performing chest compressions in accordance with identified target parameters. As discussed above, the chest compression feedback can be in the form of haptic feedback instructing the acute care provider when to initiate each compression and when to release each compression. Other forms of feedback, such as visual feedback on the device display and audio feedback emitted from the device speakers can also be provided.

As shown at box 1014, after a period of time, the acute care providers can be instructed to switch roles. Determinations of when acute care providers should switch roles can be based, for example, on portions of the treatment protocol determined in box 1006. In some examples, the rescue management apparatus can be configured to cause each acute care provider's wrist-worn device to provide a notification informing him or her to switch to another role. In some cases, the acute care provider can be instructed which new role to perform. In other examples, the acute care provider can select the new role by, for example, beginning to perform a different type of resuscitation activity. In that case, signals received from the motion and/or optical sensors of the acute care provider's wrist-worn device can be used to determine which new role the acute care provider has selected. In some examples, the instruction to switch roles is provided after a predetermined period of time (e.g., about two minute). In other examples, the determination of when to instruct acute care providers to switch roles can be based on analysis of signals received from motion sensors of the wrist-worn devices. In particular, as described above, the motion sensor signals can be analyzed to identify deterioration of CPR quality, which can indicate acute care provider fatigue. If information recorded by a wrist-worn device indicates that an acute care provider is not providing resuscitation activities of an expected quality (e.g., in the case of a chest compression, it could be determined that the compression rate and/or depth is substantially different than a target value), the acute care provider can be instructed to switch to another role. Similarly, if information collected by a wrist-worn device indicates that the acute care provider is becoming fatigued (e.g., a decreasing trend in CPR quality is identified) the acute care provider management apparatus and/or wrist-worn device can instruct the acute care provider to change roles.

As shown at box 1016, in some implementations, the treatment protocol can be modified or updated during treatment of a patient to account for factors that can occur at an emergency scene. For example, the treatment protocol can be updated if additional acute care providers arrive increasing the number of acute care providers available to provide treatment. For example, if initially one acute care provider is present, the single acute care provider can be responsible for providing both chest compressions and manual ventilation to the patient. If a second acute care provider arrives, the treatment protocol and respective roles can be updated so that one acute care provider provides compressions while, in a coordinated manner, the second acute care provider provides ventilation. Similarly, the treatment protocol can be undated as additional medical devices are set up and/or become available. For example, the rescue management apparatus can be configured to identify when a medical device, such as a defibrillator, is set up and ready for use. At that point, the treatment protocol can be undated to include instructing the acute care providers to step away from the patient and providing treatment, in the form of a defibrillating shock to the patient, provided that a shockable rhythm can be identified.

The acute care providers can continue to provide treatment to the patient in accordance with the treatment protocol for as long as necessary or appropriate for the emergency situation. However, after a period of time, as shown at box 1018, the acute care providers are instructed to cease providing treatment to the patient. The instruction to cease treatment could occur, for example, because the acute care providers and patient have arrived at a hospital or medical facility and others have taken over responsibility for treating the patient.

With reference now to FIG. 10B, an exemplary process for code review for multiple acute care providers having wearable devices will be described. As shown at box 1020, a rescue management apparatus receives information from one or more wearable electronic devices at an emergency scene. As in other examples described herein, the information can be motion information representative of movements of acute care providers wearing the electronic devices. The information can also be representative of a DTA Marker (e.g., confirmation that resuscitation activities were performed) identified by the acute care providers wearable device.

As shown at box 1022, the rescue management apparatus is configured to process the received information and to associate the received information with a respective device and acute care provider. In addition to processing the information and associating certain information with a respective acute care provider, the rescue management apparatus may further be configured to provide a time-stamped record for each acute care provider based on analysis of the received information, as shown at box 1024. For example, the rescue management apparatus may be configured to identify and record a time that each resuscitation activity was performed and/or that each DTA Marker was identified. The recorded times can be combined to produce a time-stamped record of resuscitation activities performed for a victim at an emergency scene.

As shown at box 1026, the rescue management apparatus can be configured to analyze the time-stamped records for resuscitation activities performed by the acute care providers to determine information about a quality of care provided by the acute care providers at the emergency scene. As shown at box 1028, the rescue management apparatus can also be configured to output a summary for quality of care based on the analyzed time-stamped record of activity of each acute care provider received from each acute care provider's wrist-worn device. For example, the summary can comprise a calculated score or metric for individual acute care providers or for the team of acute care providers. As discussed above, the metric can be a number or letter score based on movement and/or physiological information recorded by the wrist-worn devices worn by the respective acute care providers and/or by patient monitoring devices. Once calculated, the metric or score can be displayed to the acute care providers on their respective wrist-worn devices. Alternatively or in addition, metrics or scores for treatment quality can be sent to external sources for storage and further analysis. For example, a report card file including acute care provider score information and/or physiological outcome information can be uploaded to a data repository, remote computer database, website, or cloud storage environment. In some examples, the summary can DTA Marker include physiological information for the victim to show how certain resuscitation activities affected the victim. For example, the rescue management apparatus can be configured to coordinate the received time-stamped reports with physiological information for the victim received from other therapeutic and/or monitoring devices. In some examples, the rescue management apparatus can be configured to automatically annotate the received physiological signals (e.g., ECG, blood pressure, breathing rate, pulse oximetry levels) with DTA Markers identified by the acute care providers to produce a correlated report of patient treatment and physiological status.

In some examples, the summary or report can be sent from the rescue management apparatus to each acute care provider's wearable device. In other examples, the report can be sent from the rescue management apparatus to one or more external computing devices or computer networks. For example, reports listing treatments provided to the victim can be provided to other caregivers responsible for the victim, such as physicians and nurses at a hospital or medical facility that admits the victim for further treatment. In some instances, summaries or reports generated by the rescue management apparatus can also be included in the patient's electronic health record.

Systems for Hospital Environments

Figure 11:
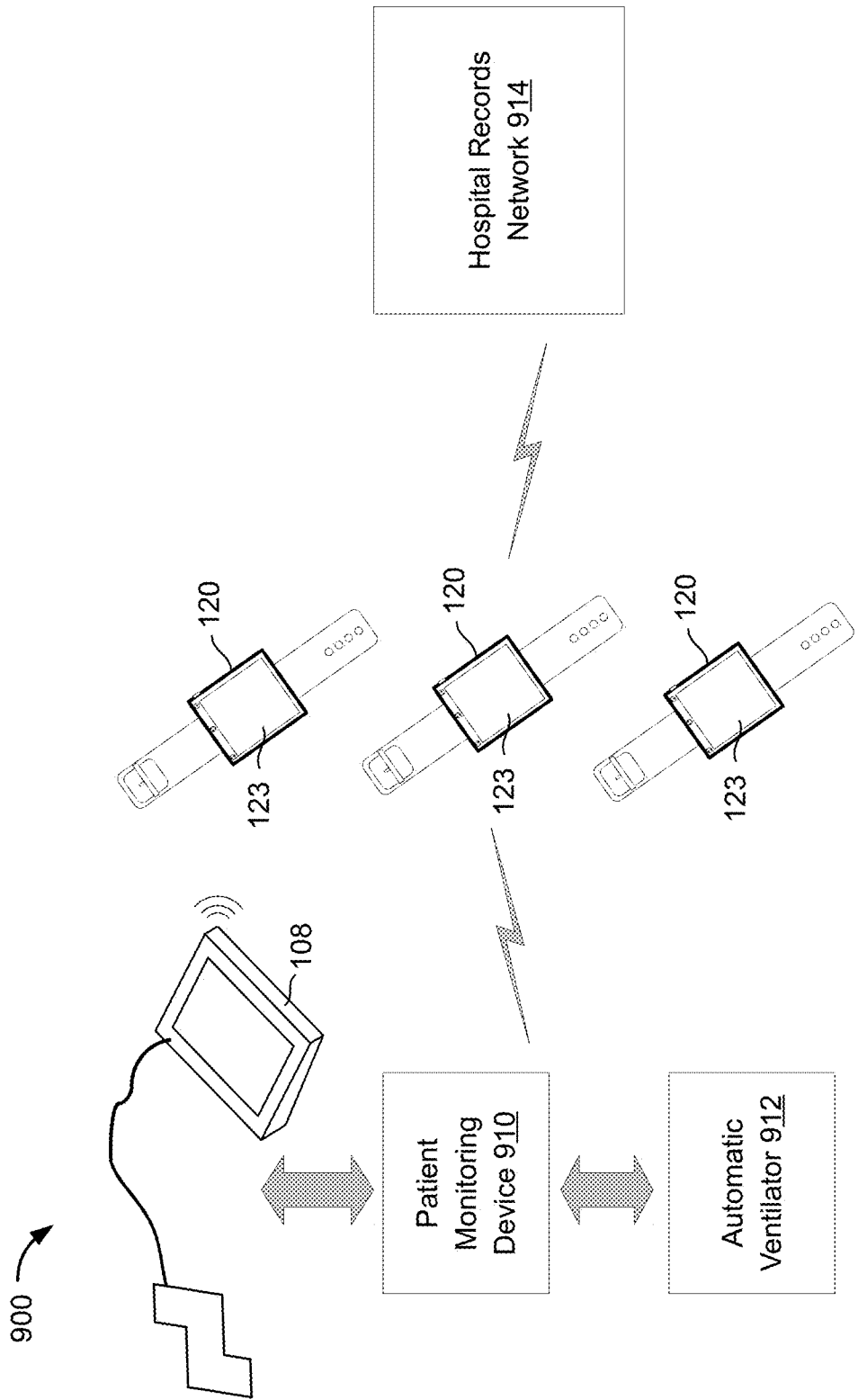
FIG. 11 is a schematic drawing of an exemplary patient management system including wrist-worn devices configured to be worn by medical personnel in a hospital environment.

With reference to FIG. 11, a system 900 comprising wrist-worn devices 120 worn by caregivers, such as doctors and nurses, at a medical facility is illustrated. As in previously described examples, the wrist-worn devices 120 are configured to be in wireless communication with other electronic devices, including medical devices, external computers, and computer databases located throughout the facility. For example, the wrist-worn devices 120 can comprise a WiFi transceiver for wirelessly receiving information and notifications from a hospital network and/or directly from medical devices located throughout the facility.

In some examples, the system 900 can comprise one or more defibrillators 108, such as a portable defibrillator or a defibrillator used with a hospital crash cart, such as the R Series manufactured by ZOLL Medical Corp. In some examples, the defibrillator 108 can be used as a patient monitoring device 910. The defibrillator 108 and/or patient monitoring device 910 can comprise sensors and electrodes configured for attachment to the patient to monitor heart rate and/or to generate ECG signals for the patient. The patient monitoring device 910 can comprise sensors to detect and monitor other physiological parameters of a patient including blood pressure, internal body temperature, skin temperature, respiration rate, blood oxygen level, end-tidal carbon dioxide level, pulmonary function, and/or blood glucose level. The system 900 can comprise additional medical devices, such as an automatic or mechanical ventilator 912 for providing ventilation to the patient.

In some examples, the medical devices 108, 912 can be configured to wirelessly transmit measured physiological information to wrist-worn devices 120 for caregivers responsible for a specific patient. The respective wrist-worn device 120 can be configured to receive the transmitted physiological information and determine whether to display the received information to the user. In other examples, the medical devices 108, 912 can be configured to process the received physiological signals to identify occurrence of patient physiological events. If an event is identified, the medical device 108, 912 can wirelessly transmit a notification to caregivers responsible for the patient.

The wrist-worn devices 120 can be in wireless communications with external computer databases, such as a hospital records network 914, including patient electronic medical records (ERMs), The wrist-worn devices 120 can be configured to receive patient information, including medical history information, patient identification information, height, weight, medications currently taking, and known allergies from the external database(s). The received patient information can be displayed on the visual displays 123 for wrist-worn devices 120 of caregivers responsible for the patient. In some cases, the wrist-worn device 120 can be configured to request the patient information from the database. For example, if a wrist-worn device 120 receives a notification related to a specific patient, the device 120 can be configured to automatically transmit a request to external database(s) for information about the patient. In some example, the wrist-worn device 120 can track location of the user and can request patient information for nearby patients. Similarly, the wrist-worn device 120 can be configured to request patient information for a patient as the user of the wrist-worn device 120 enters a particular patient's room or begins to interact with the patient. In other examples, the wrist-worn device 120 can comprise an appointment list or schedule for the user. The device 120 can be configured to request patient information for patients listed on the schedule so that the user can review the patient information prior to the scheduled appointment time.

In some examples, the wrist-worn device 120 can be a remote alarm for medical devices 108, 912 or patient monitoring devices 910 located at the medical facility. For example, when a device monitoring condition of a patient identifies a physiological event, the device can be configured to wirelessly transmit an alert to the wrist-worn device 120 of a respective user. In some examples, the system 900 can be configured to transmit the alert to all caregivers at a medical facility or within a particular department or floor of the facility. In other examples, the system 900 can be configured to transmit the alert to ad caregivers within a predetermined distance from the patient regardless of whether the caregiver is responsible for the particular patient. In other examples, the system 900 can be configured to transmit the notification to specific individuals (such as an attending physician or nurse) that is responsible for care of the particular patient experiencing the physiological event. In some examples, rather that transmitting notifications for physiological events that have occurred, the system 900 can be configured to monitor physiological data for patients to identify or estimate which patients are likely to experience a physiological event, such as cardiac arrest (e.g., event prediction). In that case, the caregiver can begin treatment for the patient to avoid or reduce the likelihood of occurrence of the physiological event. Algorithms for predicting an occurrence of a cardiac event based on measured physiological signals are disclosed, for example, in U.S. Pat. No. 7,650,181, entitled "Synchronization of Repetitive Therapeutic Interventions", and which is incorporated by reference in its entirety.

Wall-Mounted AED Monitoring

Figure 12:
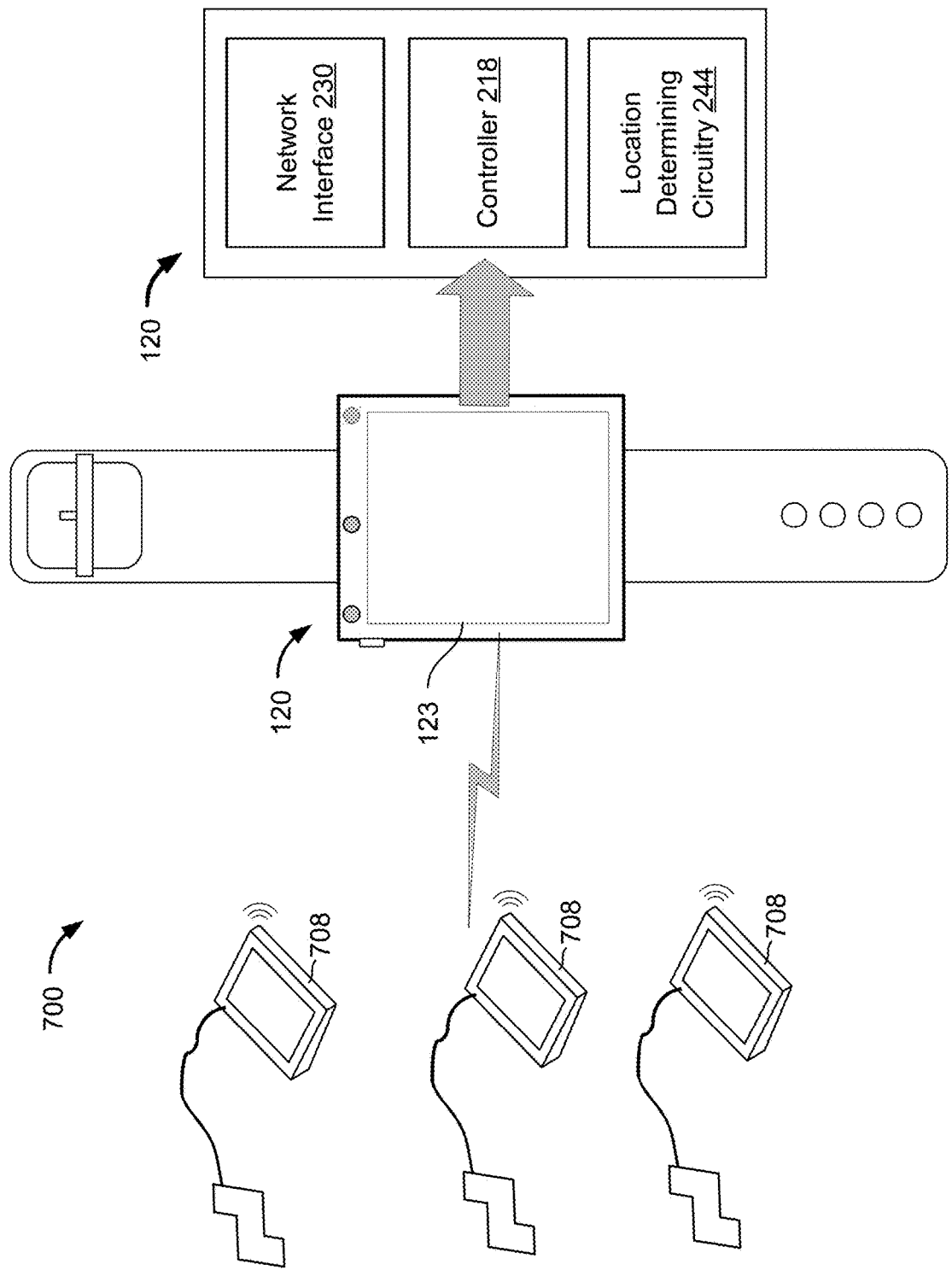
FIG. 12 is a schematic drawing of an exemplary system for locating and monitoring remote defibrillator devices with a wrist-worn device.

With reference to FIG. 12, a system 700 for monitoring status of portable electronic devices for emergency use, such as wall-mounted automatic external defibrillators (AEDs 708), using one or more wrist-worn devices 120 is illustrated. Wall-mounted AEDs 708 can be located in public areas such as shopping centers, malls, museums, airports, and lobbies of commercial buildings. As in previously described examples, the wrist-worn device 120 comprises a transceiver (e.g., network interface 230) for wireless communication with external electronic devices, such as the AEDs 708, and an output component, such as a visual display 123. The network interface 230 can be configured to receive information from one or more remote AEDs 708. The device 120 can further comprise a processor or controller 218 in communication with the network interface 230 and visual display 123 for processing information received from the AEDs 708 and generating a summary of status information for the AEDs 708. The summary of status information can be displayed to the wearer on the visual display 123.

In some examples, the device 120 further comprises location determining circuitry 244 for identifying a present location of the device 120. Location information can be used, for example, to determine a distance between the wrist-worn device 120 and the AEDs 708. Location information can also be used to provide the wearer with directions to one or more of the AEDs 708. For example, the summary generated by the controller 218 can include information about relative distance and/or travel time to each identified AED 708. The summary can also include a map or step by step instructions for the wearer to follow to the AED 708.

Since AEDs 708 are often stored for an indeterminate duration before being used to treat a patient in an emergency situation, it is important to periodically verify that the AED 708 is in operating condition. In some examples, the AED 708 can perform periodic or aperiodic self-tests for the purpose of assessing operational status of the AED 708. Based on the self-test results, an AED 708 can be configured to determine whether it is in a condition to provide treatment to a patient. In some examples, the self-test results can be automatically uploaded to an external source, such as an external computing device. In other examples, the results of the self-test can be stored in computer readable memory on the AED 708 and provided to another computing device if a request for device status is received. For example, the self-test results can be wirelessly transmitted to the wrist-worn device 120. In that case, the summary provided to the wearer of the device 120 can include self-test results for each AED 708 and, in particular, an indication of whether each AED 708 is in condition to provide treatment to a patient and/or victim.

In operation, if an emergency event occurs, a user of the wrist-worn device 120 may need to identify a nearest AED 708 to provide treatment to an incapacitated individual. In that case, the user's wrist-worn device 120 can be configured to receive status and location information for one or more AED 708 devices located nearby. In some examples, AED location information can be determined by location determining circuitry associated with the AED 708. In other examples, location information (e.g., latitude and longitude information) for the AED 708 may be known (e.g., for stationary devices) and stored on computer readable memory associated with the AED 708. More specifically, the wrist-worn device 120 can output a request signal requesting information from any AED 708 located within a predetermined distance from the current location of the user and device 120. In response to the request signal from the wrist-worn device 120, nearby AEDs 708 can be configured to transmit information including device status information and location to the wrist-worn device 120. Responses from nearby AEDs 708 received by the wrist-worn device 120 can be shown to the user on the device display 123 so that the user can evaluate available options. In some cases, the user may be able to scroll through the various AEDs using one or more functionalities of the device 120, for example, via the touch screen, scroll dial (e.g., digital crown), voice command, etc. In particular, the visual display 123 can comprise information about which nearby AEDs are operating normally, based on self-test results. The displayed information can comprise information about the nearby AEDs, such as model numbers, device features, age, and other factors that could impact an acute care provider's determination about which AED 708 to use. In some examples, the wrist-worn device 120 can display relative distance and/or directions from the user's current location to the AED 708. Location information can be determined, for example, by location determining circuitry 244 associated with the user's wrist-worn device 120. In other examples, the user's wrist-worn device 120 can be configured to analyze a quality and/or intensity of signals received from the AEDs 708 to estimate relative distance to the AED. Based on the displayed information, the user can make a determination about which AED 708 is most easily accessible and well-suited for the treatment to be performed.

Although wrist-worn devices and rescue management systems have been described in detail for the purpose of illustration based on what is currently considered to be the most practical examples, it is to be understood that such detail is solely for that purpose and that the disclosure is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

What is claimed is:

1. A system for guiding a plurality of acute care providers in providing treatment to a patient at a rescue scene, the system comprising:
    a chest compression assistance device comprising a housing configured to be positioned between a chest of the patient and hands of an acute care provider during chest compressions and at least one chest compression sensor enclosed in the housing, wherein the housing is configured to move along with the chest as chest compressions are provided to the patient;
    a plurality of wrist-worn feedback devices each comprising at least one movement sensor configured to detect movement of hands and/or wrists of a wearer, wherein each of the plurality of wrist-worn feedback devices is configured to be worn by a different respective acute care provider of the plurality of acute care providers at the rescue scene; and
    at least one controller in communication with the at least one chest compression sensor and with the plurality of wrist-worn feedback devices, the at least one controller configured to:
        receive and process signals from the at least one chest compression sensor representative of movement of the patient's chest during the chest compressions;
        determine at least one compression parameter value for the chest compressions based on the received and processed signals from the at least one chest compression sensor;
        receive and process signals from the movement sensors of the plurality of wrist-worn feedback devices;
        associate the chest compression assistance device with a particular wrist-worn feedback device of the plurality of wrist-worn feedback devices based on identified simultaneous movement detected in the signals from the at least one movement sensor of the particular wrist-worn feedback device and the signals from the at least one chest compression sensor to identify the
        particular wrist-worn feedback device of the plurality of wrist-worn feedback devices worn by the respective acute care provider that provides the chest compressions to the patient; and
        cause the particular wrist-worn feedback device worn by the respective acute care provider that provides the chest compressions to the patient to provide feedback based, at least in part, on the determined at least one compression parameter value, to the respective acute care provider for performance of the chest compressions.

2. The system of claim 1, wherein the at least one chest compression sensor comprises a single axis or a multi-axis accelerometer.

3. The system of claim 1, wherein the at least one movement sensor of the plurality of feedback devices comprises at least one of a single-axis accelerometer, a multi-axis accelerometer, or a gyroscope.

4. The system of claim 1, wherein the at least one controller is configured to cause the particular wrist-worn feedback device worn by the respective acute care provider to provide feedback for performance of the chest compressions by:
    comparing the determined at least one compression parameter value to a range of target compression parameter values for the chest compressions; and
    causing an indicator of the particular wrist-worn feedback device to emit visual, audio, and/or haptic indications at intervals and/or intensities determined based, at least in part, on the comparison.

5. The system of claim 4, wherein the at least one compression parameter value comprises a depth of the chest compressions and the range of target parameter values for the chest compressions is a depth of between about 2.0 inches and about 2.4 inches, and/or
    wherein the at least one compression parameter value comprises a rate of the chest compressions and the range of target parameter values for the chest compressions comprises a rate of between about 100 and about 120 compressions per minute.

6. The system of claim 4, wherein the indicator comprises a vibrator for providing vibration pulses to the respective acute care provider wearing the particular wrist-worn feedback device.

7. The system of claim 6, wherein the controller is configured to cause the vibrator of the particular wrist-worn feedback device to provide vibration pulses of a first frequency or shape during a chest compression downstroke until a target chest compression depth is reached and provide vibration pulses of a second frequency or shape to encourage the acute care provider to release the chest compression.

8. The system of claim 6, wherein the at least one controller is configured to cause the indicator of the particular wrist-worn feedback device to provide the indications for the acute care provider by:
    causing the vibrator to provide a pattern of vibration pulses to guide the acute care provider to perform chest compressions that are within the range of target compression parameter values;
    adjusting an intensity of the vibration pulses based, at least in part, on the comparison between the determined at least one compression parameter value and the range of target compression parameter values; and
    causing the vibrator to provide vibration pulses at the adjusted intensity while the at least one compression parameter value is not within the range of target compression values.

9. The system of claim 4, wherein the particular wrist-worn feedback device further comprises at least one visual display, and wherein the indications provided to the respective acute care provider comprise visual indications that appear on the at least one visual display providing feedback to the acute care provider for performing the chest compressions.

10. The system of claim 1, wherein the at least one controller comprises at least one of a defibrillator, patient monitor, computer tablet, laptop computer, or smartphone.

11. The system of claim 1, wherein the at least one controller comprises a computer tablet, and wherein the system further comprises a defibrillator in communication with the computer tablet configured to provide physiological information for the patient to the computer tablet.

12. The system of claim 1, wherein the at least one controller is further configured to analyze the received and processed signals from the movement sensors of the plurality of wrist-worn feedback devices to identify a particular wrist-worn feedback device of the plurality of feedback devices worn by another respective acute care provider that provides manual ventilations to the patient.

13. The system of claim 12, further comprising a manual ventilation unit comprising (i) a manual ventilation bag coupled to an airway of the patient for providing the manual ventilations to the patient, and (ii) at least one airflow sensor coupled between the manual ventilation bag and the patient's airway for detecting the manual ventilations provided to the patient.

14. The system of claim 13, wherein the at least one controller is further configured to:
receive and process signals from the at least one airflow sensor representative of the manual ventilations provided to the patient;
determine at least one ventilation parameter value for the manual ventilations based on the received and processed signals from the at least one airflow sensor;
compare the determined at least one ventilation parameter value to a range of target ventilation parameter values for the manual ventilations; and
cause the particular wrist-worn feedback device worn by the another respective acute care provider of the plurality of acute care providers that provides the manual ventilations to the patient to provide feedback to the another respective acute care provider for performance of the manual ventilations based, at least in part, on the comparison.

15. The system of claim 14, wherein the particular wrist-worn feedback device worn by the another respective acute care provider of the plurality of acute care providers that provides the manual ventilations to the patient comprises a vibrator for providing vibration pulses to the acute care provider wearing the device, and
wherein the at least one controller is configured to provide vibration pulses of a first frequency or shape during compression of the manual ventilation bag until a target ventilation volume is reached, and provide a different second frequency or shape of vibration pulses to encourage the acute care provider to release the manual ventilation bag.

16. The system of claim 14, wherein the particular wrist-worn feedback device worn by the another respective acute care provider of the plurality of acute care providers that provides the manual ventilations to the patient comprises a vibrator for providing vibration pulses to the acute care provider wearing the device, and
wherein the at least one controller causes the particular wrist-worn feedback device worn by the another respective acute care provider of the plurality of acute care providers that provides the manual ventilations to provide the feedback by: causing the vibrator to provide vibration pulses to guide the acute care provider to compress the manual ventilation bag to provide ventilations that are within the range of target ventilation parameter values; adjusting an intensity of the vibration pulses based, at least in part, on the comparison between the determined at least one ventilation parameter value and the range of target ventilation parameter values; and causing the vibrator to provide vibration pulses at the adjusted intensity when the determined at least one ventilation parameter value is not within the range of target ventilation parameter values.

17. The system of claim 14, wherein the range of target ventilation parameter values comprises a ventilation rate of about 10 ventilations per minute for an adult to about 20 ventilations per minute for an infant.

18. The system of claim 1, wherein the at least one controller is further configured to confirm that full release of the chest of the patient is occurring during the chest compressions based on a comparison between the signals from the at least one movement sensor of the particular wrist-worn feedback device worn by the respective acute care provider that provides the chest compressions and the signals from the at least one chest compression sensor.

19. The system of claim 1, wherein the at least one controller is further configured to assess accuracy of the at least one chest compression sensor and/or the at least one movement sensor of the particular wrist worn feedback device based on a comparison of determined at least one chest compression parameter value and the signals from the at least one movement sensor of the particular wrist-worn feedback device.

20. The system of claim 1, wherein the chest compression assistance device comprises a CPR puck, and wherein the housing is substantially rigid.

21. The system of claim 1, wherein the chest compression assistance device is integrated with an electrode package comprising one or more defibrillation electrodes configured to be connected to a defibrillator.

* * * * *